(«12») United States Patent
Gomez et al.

(10) Patent No.: US 10,526,315 B2
(45) Date of Patent: Jan. 7, 2020

(54) CARBOCYCLIC PROLINAMIDE DERIVATIVES

(71) Applicant: ORION OPHTHALMOLOGY LLC, New York, NY (US)

(72) Inventors: Robert Gomez, North Vancouver (CA); Jinyue Ding, Burnaby (CA); Renata Marcella Oballa, Coquitlam (CA); David Andrew Powell, Vancouver (CA)

(73) Assignee: ORION OPHTHALMOLOGY LLC, New York, NY (US)

( * ) Notice: Subject to any disclaimer, the term of this patent is extended or adjusted under 35 U.S.C. 154(b) by 0 days.

(21) Appl. No.: 16/312,211

(22) PCT Filed: Jun. 15, 2017

(86) PCT No.: PCT/US2017/037766
§ 371 (c)(1),
(2) Date: Dec. 20, 2018

(87) PCT Pub. No.: WO2017/222914
PCT Pub. Date: Dec. 28, 2017

(65) Prior Publication Data
US 2019/0202810 A1  Jul. 4, 2019

Related U.S. Application Data

(60) Provisional application No. 62/352,959, filed on Jun. 21, 2016.

(51) Int. Cl.
*C07D 403/04* (2006.01)
*C07D 207/50* (2006.01)
*C07D 405/14* (2006.01)
*C07D 471/04* (2006.01)
*C07D 401/14* (2006.01)
*C07D 401/04* (2006.01)
*C07D 403/14* (2006.01)

(52) U.S. Cl.
CPC ......... *C07D 403/04* (2013.01); *C07D 207/50* (2013.01); *C07D 401/04* (2013.01); *C07D 401/14* (2013.01); *C07D 403/14* (2013.01); *C07D 405/14* (2013.01); *C07D 471/04* (2013.01)

(58) Field of Classification Search
CPC .. C07D 403/04; C07D 207/50; C07D 405/14; C07D 471/04; C07D 401/14
USPC ........................................................ 548/530
See application file for complete search history.

(56) References Cited

U.S. PATENT DOCUMENTS 4,562,197 A * 12/1985 Snarey ................ C07K 5/0825
514/21.9
2003/0216325 A1  11/2003 Saksena et al.

FOREIGN PATENT DOCUMENTS

WO   WO 2004-113365 A2   12/2004
WO   WO 2011-075607 A1    6/2011
WO   WO 2012-078540 A1    6/2012

OTHER PUBLICATIONS

Bachovchin, D. A. et al., "A high-throughput, multiplexed assay for superfamily-wide profiling of enzyme activity", Nature Chemical Biology, 2014, vol. 10, No. 8, pp. 656-663.

(Continued)

*Primary Examiner* — Niloofar Rahmani
(74) *Attorney, Agent, or Firm* — Haug Partners LLP

(57) ABSTRACT

This invention is directed to novel carbocyclic prolinamide derivatives of Formula (I), and pharmaceutically acceptable salts, solvates, solvates of the salt and prodrugs thereof, useful in the prevention (e.g., delaying the onset of or reducing the risk of developing) and treatment (e.g., controlling, alleviating, or slowing the progression of) of age-related macular degeneration (AMD) and related diseases of the eye. These diseases include dry-AMD, wet-AMD, geographic atrophy, diabetic retinopathy, retinopathy of prematurity, polypoidal choroidal vasculopathy, and degeneration of retinal or photoreceptor cells. The invention disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, and degeneration of retinal or photoreceptor cells, comprising: administration of a therapeutically effective amount of compound of the invention. The compounds of the invention are inhibitors of HTRA1. Thus, the compounds of the invention are useful in the prevention and treatment of a wide range of diseases mediated (in whole or in part) by HTRA1. The compounds of the invention are also useful for inhibiting HTRA1 protease activity in an eye or locus of an arthritis or related condition.

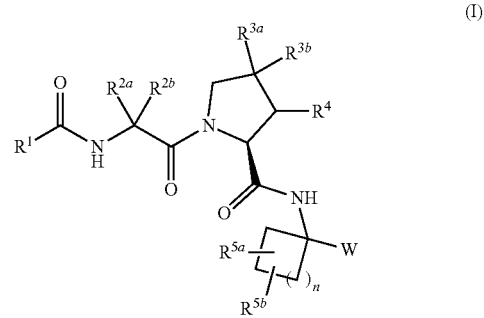

12 Claims, No Drawings

(56) References Cited

OTHER PUBLICATIONS

International Search Report and Written Opinion dated Sep. 25, 2017 in corresponding International Application No. PCT/US2017/037766.

* cited by examiner

CARBOCYCLIC PROLINAMIDE DERIVATIVES

CROSS-REFERENCE TO RELATED APPLICATIONS

This application is the National Stage entry under 35 U.S.C. § 371 of International Application No. PCT/US2017/037766 filed on Jun. 15, 2017, published on Dec. 28, 2017 under Publication Number WO 2017/222914, which claims the benefit of U.S. Provisional Application No. 62/352,959 filed Jun. 21, 2016, the entireties of which are herein incorporated by reference.

BACKGROUND OF THE INVENTION

Field of the Invention

The present disclosure is directed to novel carbocyclic prolinamide derivatives, pharmaceutical compositions containing such novel compounds, as well as methods for preventing and treating age-related macular degeneration (AMD) and related diseases of the eye.

Description of the Related Art

Age-related macular degeneration (AMD) is the leading cause of severe loss of vision in people over the age of 60. Age is the major risk factor for the onset of AMD: the likelihood of developing AMD triples after age 55. Many factors, however, contribute to the likelihood that an individual will develop AMD.

As summarized in WO2001/006262, "environmental" conditions may modulate the rate at which an individual develops AMD or the severity of the disease. Light exposure has been proposed as a possible risk factor, since AMD most severely affects the macula, where light exposure is high. (See Young, R. W. (1988), Surv. Ophthalmol. 32(4), 252-69; Taylor, H. R. et al., (1990), Trans. Amer. Ophthalmol. Soc. 88, 163-73; Schalch W. (1992), Exs, 62, 280-98). The amount of time spent outdoors is associated with increased risk of choroidal neovascularization in men, and wearing hats and/or sunglasses is associated with a decreased incidence of soft drusen (Cruickshanks, K. et al., (1993), Arch. Ophthalmol., 111, 514-518). Accidental exposure to microwave irradiation has also been shown to be associated with the development of numerous drusen (Lim, J. et al., (1993), Retina. 13, 230-3). Cataract removal and light iris pigmentation has also been reported as a risk factor in some studies (Sandberg, M. et al., (1994), Invest. Ophthalmol. Vis. Sci. 35(6), 2734-40). This suggests that: 1) eyes prone to cataracts may be more likely to develop AMD; 2) the surgical stress of cataract removal may result in increased risk of AMD, due to inflammation or other surgically-induced factors; or 3) cataracts prevent excessive light exposure from falling on the macula, and are in some way prophylactic for AMD. While it is possible that dark iris pigmentation may protect the macula from light damage, it is difficult to distinguish between iris pigmentation alone and other, co-segregating genetic factors which may be actual risk factors.

Smoking, gender (women are at greater risk), obesity, and repeated exposure to UV radiation also increase the risk of AMD.

More recently, a number of HTRA1 single nucleotide polymorphs (SNP) have been found to be associated with an increased risk of AMD. See, for example, WO2008/013893A2, WO2008/067040A2 and WO2008/094370A2. These SNP's include rs11200638, rs10490924, rs3750848, rs3793917 and rs932275. In particular, the risk allele rs11200638, was found to be associated with increased HTRA1 mRNA and protein expression, and HTRA1 is present in drusen in patients with AMD. (See Dewan et al., (2006), Science 314:989-992; Yang et al., (2006), Science 314:992-993). These disclosures provide evidence that HTRA1 is an important factor in AMD and the progression thereof.

In broad terms, there are two forms of AMD: dry AMD and wet AMD. The dry form is the more common, and accounts for 85-90% of the patients with AMD, and does not typically result in blindness. In dry AMD, (also called non-neovascular AMD or non-exudative AMD) drusen appear in the macula of the eye, the cells in the macula die, and vision becomes blurry. Dry AMD can progress in three stages: 1) early, 2) intermediate, and 3) advanced dry AMD. Dry AMD can also progress into wet AMD during any of these stages.

Wet AMD (also called neovascular or exudative AMD), is associated with pathologic posterior segment neovascularization. The posterior segment neovascularization (PSNV) found in exudative AMD is characterized as pathologic choroidal neovascularization. Leakage from abnormal blood vessels forming in this process damages the macula and impairs vision, eventually leading to blindness.

The end stage of AMD is characterized by a complete degeneration of the neurosensory retina and of the underlying retinal pigment epithelium in the macular area. Advanced stages of AMD can be subdivided into geographic atrophy (GA) and exudative AMD. Geographic atrophy is characterized by progressive atrophy of the retinal pigment epithelium (RPE). While GA is typically considered less severe than the exudative AMD because its onset is less sudden, to date no treatment has been effective at halting or slowing its progression.

Currently, treatment of dry AMD includes the administration of antioxidant vitamins and/or zinc. For example, one study at the National Eye Institute assessed a composition comprising vitamin C, β-carotene, zinc oxide and cupric oxide.

Treatment of wet AMD is also wanting. Available drug therapies include: bevacizumab (Avastin®, Genentech, CA), ranibizumab (Lucentis®, Genentech, CA), pegaptanib (Macugen® Bausch & Lomb, NJ), and aflibercept (Eylea®, Regeneron, NY). In each instance, the medication is injected into the eye. Injections may be repeated every four to eight weeks to maintain the beneficial effect of the medication. Those with a positive result may partially recover vision as the blood vessels shrink and the fluid under the retina is absorbed, allowing retinal cells to regain some function.

Pharmacologic therapy for the treatment of macular edema associated with AMD is lacking. The current standard of care is laser photocoagulation, which is used to stabilize or resolve macular edema and retard the progression to later stage disease. Laser photocoagulation may reduce retinal ischemia by destroying healthy tissue and thereby decreasing metabolic demand; it also may modulate the expression and production of various cytokine and trophic factors. There are no current treatments for preventing loss of vision after dry AMD enters an advanced stage. There are also no definitive methods for preventing progression of dry AMD to an advanced stage, other than by avoiding and/or reducing risk factors and using dietary supplements, which cannot guarantee or be relied on to stop AMD progression. Thus, there is a need for therapeutics that can treat dry AMD and prevent progression of dry to wet AMD.

The compound (1-{3-cyclohexyl-2-[naphthalene-2-carbonyl)-amino]-propionyl}-pyrrolidine-2-carboxylic acid [5-(3-cyclohexyl-ureido)-1-dihydroxyboranyl-pentyl]-amide is disclosed in Grau, S. et. al., (2006), J. Biol. Chem., 281(10): 6124-6129 and in WO2012/078540 (identified therein as NVP-LB976) as an inhibitor of HTRA1.

In addition to AMD, a number of publications have described a potential role of HTRA1 and disease, including retinal angiomatous proliferation (Ohkuma, Y., et al., (2014) Clin. Ophthalmol., 8:143-8), foveomacular proliferation (Chowers, I., et al., (2015) Progress in Retinal and Eye Research, 47:64-85), musculoskeletal diseases, including osteoarthritis, spinal disk degeneration rheumatoid arthritis, muscular dystrophy and osteoporosis (Taiden, A. N. and Richards, P. J. (2013) Am. J. Pathology, 182(5):1482-8), and treatment of autologous chondrocytes prior to intraarticular implantation (Ollitrault, D. et al., (2015) Tissue Engineering, Part C Methods, 21(2):133-47). An HTRA1 inhibitor thus may demonstrate a therapeutic benefit in these additional indications.

SUMMARY OF THE INVENTION

The present disclosure is directed to novel carbocyclic prolinamide derivatives of Formula I, and pharmaceutically acceptable salts, solvates, solvates of the salts and prodrugs thereof, pharmaceutical compositions comprising a compound of Formula I, as well as methods for preventing and treating age-related macular degeneration (AMD) and related diseases of the eye comprising administering to a patient in need thereof a therapeutically effective amount of a compound of Formula I. These diseases include, but are not limited to, dry-AMD, wet-AMD, geographic atrophy, diabetic retinopathy, retinopathy of prematurity, polypoidal choroidal vasculopathy, and degeneration of retinal or photoreceptor cells. The compounds of the present disclosure are inhibitors of HTRA1, and are useful in the prevention and treatment of diseases mediated (in whole or in part) by HTRA1. The compounds of the present disclosure are also useful for inhibiting HTRA1 protease activity in an eye or locus of an arthritis or related condition.

DETAILED DESCRIPTION OF THE PREFERRED EMBODIMENT

In a first embodiment the present disclosure provides compounds of Formula

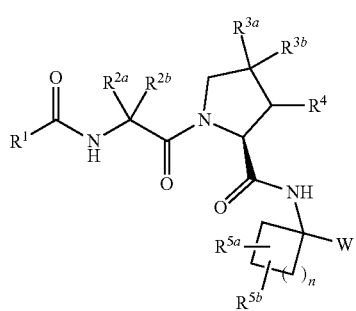

(I)

or a pharmaceutically acceptable salt, solvate, solvate of the salt or prodrug thereof wherein:
W is selected from the group consisting of: —B(OH)$_2$ and —C(O)C(O)NR$^7$R$^8$;

R$^1$ is selected from the group consisting of:
(a) —(CH$_2$)$_{0-6}$-aryl, and
(b) —(CH$_2$)$_{0-6}$-heteroaryl,
wherein the aryl and heteroaryl of choices (a) and (b) are each optionally substituted with 1 to 3 substituents independently selected from the group consisting of:
(i) -halogen,
(ii) —CN,
(iii) —C$_{1-6}$alkyl,
(iv) —C$_{0-6}$alkyl-R$^6$,
(v) —C$_{2-6}$alkenyl,
(vi) —C$_{2-6}$alkynyl,
(vii) —C(O)R,
(viii) —CO$_2$R$^7$,
(ix) —CONR$^7$R$^8$,
(x) —OH,
(xi) —O—C$_{1-6}$alkyl,
(xii) —O—C$_{0-6}$alkyl-R$^6$,
(xiii) —SH,
(xiv) —S(O)$_p$—C$_{1-6}$alkyl,
(xv) —S(O)$_p$—C$_{0-6}$alkyl-R$^6$,
(xvi) —S(O)$_2$NR$^7$R$^8$,
(xvii) —NO$_2$,
(xviii) —NR$^7$R$^8$,
(xix) —NHC(O)R$^7$,
(xx) —NHC(O)OR$^7$,
(xxi) —NHC(O)NR$^7$R$^8$,
(xxii) —NHSO$_2$C$_{1-6}$alkyl, and
(xxiii) —NHSO$_2$C$_{0-6}$alkyl-R$^6$,
(xxiv) —CONH(CH$_2$)$_{2-4}$—[O(CH$_2$)$_{2-4}$]$_m$OC$_{1-4}$alkyl,
wherein each of the alkyl group of choices (iii), (iv), (xi), (xii), (xiv), (xv), (xxii), (xxiii) and (xxiv) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl; R$^{2a}$ and R$^{2b}$ are independently selected from the group consisting of:
(a) —H,
(b) —C$_{1-8}$alkyl, and
(c) —C$_{0-6}$alkyl-R$^6$,
wherein each of the alkyl group of choices (b) and (c) is optionally substituted with 1 to 5 substituents independently selected from:
(i) -halogen,
(ii) -haloC$_{1-4}$alkyl,
(iii) —NR$^7$R$^8$,
(iv) —OH,
(v) —O—C$_{1-4}$alkyl,
(vi) —SH,
(vii) —S—C$_{1-4}$alkyl,
(viii) —NR$^7$SO$_2$C$_{1-4}$alkyl,
(ix) —NR$^7$C(O)R$^7$, and
(x) —NR$^7$C(O)OR$^7$,
with the proviso that R$^{2a}$ and R$^{2b}$ are not both H;
R$^{3a}$ is H, and R$^{3b}$ is selected from the group consisting of:
(a) —H,
(b) —OH,
(c) -heteroaryl,
(d) —O-heteroaryl,
(e) -heterocycle,
(f) -aryl, and
(g) —O-aryl;
wherein each of the heteroaryl of choices (c) and (d), the heterocycle of choice (e) and the aryl of choices (f) and (g) is optionally substituted with 1 to 3 groups independently selected from the group consisting of:

(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl,
(v) —(CH$_2$)$_{0-3}$—NHSO$_2$—C$_{3-12}$cycloalkyl,
(vi) —(CH$_2$)$_{0-3}$—SO$_2$—C$_{1-4}$alkyl,
(vii) —(CH$_2$)$_{0-3}$—C(O)O—R$^7$, and
(viii) —CN; and
wherein the heterocycle of choice (e) is additionally optionally substituted with 1 to 2 oxo groups; or
R$^{3a}$ and R$^{3b}$ together represent oxo;
R$^4$ is selected from a group consisting of
(a) —H,
(b) —C$_{1-4}$alkyl,
(c) -haloC$_{1-4}$alkyl,
(d) —O—C$_{1-4}$alkyl, and
(e) —O-haloC$_{1-4}$alkyl;
R$^{5a}$ and R$^{5b}$ are independently selected from a group consisting of
(a) —H,
(b) —C$_{1-4}$alkyl,
(c) -halogen,
(d) —OH,
(e) —O—C$_{1-4}$alkyl,
(f) —SH, and
(g) —S—C$_{1-4}$alkyl, or
R$^{5a}$, R$^{5b}$ and the atom(s) to which they are attached together form a 3- to 6-membered cycloalkyl or a 4- to 6-membered heterocycle having a heteroatom selected from O and S(O)$_p$, and wherein said cycloalkyl or heterocycle is optionally substituted with 1 to 2 groups independently selected from halogen, —C$_{1-4}$alkyl, —OH, —O—C$_{1-4}$alkyl, —SH, —S—C$_{1-4}$alkyl;
R$^6$ is selected from the group consisting of:
(a) —C$_{3-12}$cycloalkyl,
(b) -aryl,
(c) -heteroaryl, and
(d) -heterocyclyl,
wherein each of choices (a) to (d) is optionally substituted with 1 to 3 substituents independently selected from the group consisting of:
(i) —C$_{1-4}$alkyl,
(ii) -halogen,
(iii) —NR$^7$R$^8$,
(iv) —OH,
(v) —O—C$_{1-4}$alkyl,
(vi) —SH, and
(vii) —S—C$_{1-4}$alkyl;
wherein each of the alkyl group of choices (i), (v) and (vii) is optionally substituted with 1 to 5 substituents independently selected from -halogen, -haloC$_{1-4}$alkyl, —OH, —O—C$_{1-4}$alkyl, —SH and —S—C$_{1-4}$alkyl;
each R$^7$ and each R$^8$ are independently selected from the group consisting of:
(a) —H,
(b) —C$_{1-6}$alkyl,
(c) —C$_{0-6}$alkyl-C$_{3-12}$cycloalkyl,
(d) —C$_{0-6}$alkyl-heterocyclyl,
(e) —C$_{0-6}$alkyl-heteroaryl,
(f) —C$_{0-6}$alkyl-aryl,
(g) —C$_{2-6}$alkenyl, and
(h) —C$_{2-6}$alkynyl,
wherein the alkyl group of choices (b)-(f), the alkenyl group of choice (g) and the alkynyl group of (h) are each optionally substituted with 1 to 3 groups independently selected from:
(i) -halogen,
(ii) —C(O)C$_{1-4}$alkyl,
(iii) —C(O)NH$_2$,
(iv) —C(O)NH(C$_{1-4}$alkyl),
(v) —C(O)N(C$_{1-4}$alkyl)(C$_{1-4}$alkyl),
(vi) —OH,
(vii) —OC$_{1-4}$alkyl,
(viii) —SH,
(ix) —S(O)$_p$C$_{1-4}$alkyl,
(x) —NH$_2$,
(xi) —NH(C$_{1-4}$alkyl), and
(xii) —N(C$_{1-4}$alkyl)(C$_{1-4}$alkyl); or
R$^7$, R$^8$ and the nitrogen atom to which they are attached together form a 3- to 7-membered monocyclic or 6- to 11-membered bicyclic heterocycle optionally having an additional heteroatom selected from O, S(O)$_p$, and NR$^9$, and wherein said heterocycle is optionally substituted with 1 to 2 halogen;
R$^9$ is selected from the group consisting of:
(a) —H,
(b) —C$_{1-4}$alkyl,
(c) —C(O)—C$_{1-4}$alkyl,
(d) —C(O)NH$_2$,
(e) —C(O)—NH(C$_{1-4}$alkyl),
(f) —C(O)—N(C$_{1-4}$alkyl)$_2$,
(g) —C(O)O—C$_{1-4}$alkyl; and
(h) —C(O)O—C$_{1-4}$alkyl-aryl;
R$^{10}$, R$^{11}$, and R$^{12}$ are independently selected from the group consisting of: H, halogen, —OH and —C$_{1-6}$ alkyl; or
R$^{10}$, R$^{11}$ and the atom to which they are attached together form a C$_{3-12}$cycloalkyl or a heterocyclyl group;
n is 0, 1, 2, 3, 4 or 5;
m is 1-25; and
p is 0, 1 or 2.

In a second embodiment, for a compound of the first embodiment, R$^1$ is selected from the group consisting of:
(a) -aryl, and
(b) -heteroaryl,
wherein aryl and heteroaryl of choices (a) and (b) are each optionally substituted with 1 to 3 substituents independently selected from the group consisting of:
(i) -halogen,
(ii) —CN,
(iii) —C$_{1-6}$alkyl,
(iv) —C$_{0-6}$alkyl-R$^6$,
(v) —C$_{2-6}$alkenyl,
(vi) —C$_{2-6}$alkynyl,
(vii) —C(O)R$^7$,
(viii) —CO$_2$R$^7$,
(ix) —CONR$^7$R$^8$,
(x) —OH,
(xi) —O—C$_{1-6}$alkyl,
(xii) —O—C$_{0-6}$alkyl-R$^6$,
(xiii) —SH,
(xiv) —S(O)$_p$—C$_{1-6}$alkyl,
(xv) —S(O)$_p$—C$_{0-6}$alkyl-R$^6$,
(xvi) —S(O)$_2$NR$^7$R$^8$,
(xvii) —NO$_2$,
(xviii) —NR$^7$R$^8$,
(xix) —NHC(O)R$^7$,
(xx) —NHC(O)OR$^7$,
(xxi) —NHC(O)NR$^7$R$^8$,
(xxii) —NHSO$_2$C$_{1-6}$alkyl, and
(xxiii) —NHSO$_2$C$_{0-6}$alkyl-R$^6$,
(xxiv) —CONHC$_{2-4}$alkyl-(OC$_{2-4}$alkylene)$_m$OC$_{1-4}$alkyl,
wherein each of the alkyl group of choices (iii), (iv), (xi), (xii), (xiv), (xv), (xxii) and (xxiii) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl.

In a third embodiment, for a compound of any of the preceding embodiments, R$^1$ is selected from the group consisting of:
(a) -aryl, and
(b) -heteroaryl,
wherein the aryl and heteroaryl of choices (a) and (b) are each optionally substituted with 1 to 3 substituents independently selected from the group consisting of:
(i) -halogen,
(ii) —CN,
(iii) —C(O)R$^7$,
(iv) —CONR$^7$R$^8$,
(v) —OH,
(vi) —O—C$_{1-6}$alkyl,
(vii) —S(O)$_p$—C$_{1-6}$alkyl,
(viii) —S(O)$_p$—C$_{0-6}$alkyl-R$^6$,
(ix) —S(O)$_2$NR$^7$R$^8$,
(x) —NHSO$_2$C$_{1-6}$alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl.

In a fourth embodiment, for a compound of any of the preceding embodiments, R$^{2a}$ is H, and R$^{2b}$ is —C$_{1-6}$alkyl-R$^6$, where the alkyl portion of R$^{2b}$ is optionally substituted with 1 to 5 substituents independently selected from:
(i) -halogen,
(ii) -haloC$_{1-4}$alkyl,
(iii) —NR$^7$R$^8$,
(iv) —OH,
(v) —O—C$_{1-4}$alkyl,
(vi) —SH, and
(vii) —S—C$_{1-4}$alkyl.

In a fifth embodiment, for a compound of any of the preceding embodiments, R$^{2a}$ is H, and R$^{2b}$ is —C$_{1-6}$alkyl-R$^6$, and
R$^6$ is —C$_{3-12}$cycloalkyl, optionally substituted with 1 to 3 substituents independently selected from the group consisting of:
(i) —C$_{1-4}$alkyl,
(ii) -halogen,
(iii) —NR$^7$R$^8$,
(iv) —OH,
(v) —O—C$_{1-4}$alkyl,
(vi) —SH, and
(vii) —S—C$_{1-4}$alkyl.

In a sixth embodiment, for a compound of any of the preceding embodiments, R$^{3a}$ is H, and R$^{3b}$ is selected from the group consisting of:

(a) HAr—N⟩—

(b) Hcyl—N⟩—, wherein HAr is heteroaryl and Hcyl is heterocycle, wherein HAr and Hcyl are optionally substituted with 1 to 3 groups independently selected from the group consisting of:
(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl,
(v) —(CH$_2$)$_{0-3}$—NHSO$_2$—C$_{3-12}$cycloalkyl,
(vi) —(CH$_2$)$_{0-3}$—SO$_2$—C$_{1-4}$alkyl,
(vii) —(CH$_2$)$_{0-3}$—C(O)O—R$^7$, and
(viii) —CN; and
wherein Hcyl is additionally optionally substituted with 1 to 2 oxo groups.

In a seventh embodiment, for a compound of the first embodiment is a compound having formula Ia:

Ia or a pharmaceutically acceptable salt, solvate, solvate of the salt or prodrug thereof wherein:
W is —C(O)C(O)NR$^7$R$^8$,
X is selected from the group consisting of:
(a) —CR$^{10}$R$^{11}$R$^{12}$,
(b) —(CH$_2$)$_{0-3}$—SO$_2$—C$_{1-4}$alkyl,
(c) —(CH$_2$)$_{0-3}$—C(O)O—R$^7$,
(d) —(CH$_2$)$_{0-3}$—NHSO$_2$—C$_{1-4}$alkyl, and
(e) —(CH$_2$)$_{0-3}$—NHSO$_2$—C$_{3-12}$cycloalkyl;
R$^1$ is selected from the group consisting of:
(a) -aryl and
(b) -heteroaryl,
wherein the aryl and heteroaryl of choices (a) and (b) are each optionally substituted with 1 to 3 substituents independently selected from the group consisting of:
(i) -halogen,
(ii) —CN,
(iii) —C(O)R$^7$,
(iv) —CONR$^7$R$^8$,
(v) —OH,
(vi) —O—C$_{1-6}$alkyl,
(vii) —S(O)$_p$—C$_{1-6}$alkyl,
(viii) —S(O)$_p$—C$_{0-6}$alkyl-R$^6$,
(ix) —S(O)$_2$NR$^7$R$^8$,
(x) —NHSO$_2$C$_{1-6}$alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl;
R$^{5a}$ and R$^{5b}$ are independently selected from a group consisting of
(a) —H,
(b) —C$_{1-4}$alkyl, (c) -halogen,
(d) —OH,
(e) —O—$C_{1-4}$alkyl,
(f) —SH, and
(g) —S—$C_{1-4}$alkyl, or $R^{5a}$, $R^{5b}$ and the atom(s) to which they are attached together form a 3- to 6-membered cycloalkyl or a 4- to 6-membered heterocycle having a heteroatom selected from O and $S(O)_p$, and wherein said cycloalkyl or heterocycle is optionally substituted with 1 to 2 groups independently selected from halogen, —$C_{1-4}$alkyl, —OH, —O—$C_{1-4}$alkyl, —SH, —S—$C_{1-4}$alkyl;

$R^6$ is —$C_{3-12}$cycloalkyl, optionally substituted with 1 to 3 substituents independently selected from the group consisting of:
  (i) —$C_{1-4}$alkyl,
  (ii) -halogen,
  (iii) —$NR^7R^8$,
  (iv) —OH,
  (v) —O—$C_{1-4}$alkyl,
  (vi) —SH, and
  (vii) —S—$C_{1-4}$alkyl;

each $R^7$ and each $R^8$ are independently selected from the group consisting of:
  (a) —H,
  (b) —$C_{1-6}$alkyl,
  (c) —$C_{0-6}$alkyl-$C_{3-12}$cycloalkyl, and
  (d) —$C_{0-6}$alkyl-heterocyclyl,
wherein the alkyl group of choices (b)-(d) are each optionally substituted with 1 to 3 groups independently selected from:
  (i) -halogen,
  (ii) —$C(O)C_{1-4}$alkyl,
  (iii) —$C(O)NH_2$,
  (iv) —$C(O)NH(C_{1-4}$alkyl),
  (v) —$C(O)N(C_{1-4}$alkyl)($C_{1-4}$alkyl)
  (vi) —$S(O)_pC_{1-4}$alkyl, or $R^7$, $R^8$ and the nitrogen atom to which they are attached together form a 3- to 7-membered monocyclic or 6- to 11-membered bicyclic heterocycle optionally having an additional heteroatom selected from O, $S(O)_p$, and $NR^9$, and wherein said heterocycle is optionally substituted with 1 to 2 halogen;

$R^9$ is selected from the group consisting of:
  (a) —H,
  (b) —$C_{1-4}$alkyl,
  (c) —C(O)—$C_{1-4}$alkyl,
  (d) —$C(O)NH_2$,
  (e) —C(O)—$NH(C_{1-4}$alkyl),
  (f) —C(O)—$N(C_{1-4}$alkyl)$_2$,
  (g) —C(O)O—$C_{1-4}$alkyl; and
  (h) —C(O)O—$C_{1-4}$alkyl-aryl;

$R^{10}$, $R^{11}$, and $R^{12}$ are independently selected from the group consisting of: H, halogen, —OH and —$C_{1-6}$ alkyl; or $R^{10}$, $R^{11}$ and the atom to which they are attached together form a $C_{3-12}$cycloalkyl or a heterocyclyl group;

n is 0, 1, 2, 3, 4 or 5;
m is 1-25; and
p is 0, 1 or 2.

In an eighth embodiment, for a compound of any of the preceding embodiments having the formula Ia, W is —C(O)C(O)$NH_2$.

In a ninth embodiment, for a compound of any of the preceding embodiments having the formula Ia,
X is —$CR^{10}R^{11}R^{12}$,
$R^{10}$ and $R^{11}$ are each —$C_{1-4}$alkyl, or $R^{10}$, $R^{11}$ and the atom to which they are attached together form a $C_{3-6}$cycloalkyl or a 4- to 6-membered heterocycle, and
$R^{12}$ is —OH.

In a tenth embodiment, for a compound of any of the preceding embodiments having the formula Ia,
$R^{5a}$ and $R^{5b}$ are independently selected from a group consisting of
  (a) —H, and
  (b) —$C_{1-4}$alkyl, or
$R^{5a}$, $R^{5b}$ and the atom(s) to which they are attached together form a 3- to 6-membered cycloalkyl.

In an eleventh embodiment, the compound of the first embodiment is a compound selected from the group consisting of:

(2S,4S)-1-((R)-2-(2-naphthamido)-3-cyclohexylpropanoyl)-N-(1-(2-amino-2-oxoacetyl)-cyclobutyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclopropyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclopentyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cycloheptyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclooctyl)-4-(5-(2-hydroxypropan-2-yl)-1H-1,2,3-triazol-1-yl)pyrrolidine-2-carboxamide;

(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid;

(2S,4R)-1-((R)-2-(2-naphthamido)-3-cyclohexylpropanoyl)-N-(1-(2-amino-2-oxoacetyl)-cyclohexyl)-4-(piperidin-1-yl)pyrrolidine-2-carboxamide;

(2S,3R,4R)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)-3-methoxypyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-((methylsulfonyl)methyl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(5-(3-hydroxyoxetan-3-yl)-1H-1,2,3-triazol-1-yl)pyrrolidine-2-carboxamide;

2-(1-((3S,5S)-1-((R)-2-(2-naphthamido)-3-cyclohexylpropanoyl)-5-((1-(2-amino-2-oxoacetyl)cyclohexyl)carbamoyl)pyrrolidin-3-yl)-1H-1,2,3-triazol-5-yl)acetic acid;

(2S,4S)-1-((R)-2-(2-naphthamido)-3-cyclohexylpropanoyl)-N-(1-(2-amino-2-oxoacetyl)-cyclohexyl)-4-(5-(cyclopropanesulfonamidomethyl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(5-((methylsulfonyl)methyl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(5-(3-hydroxyoxetan-3-yl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(4-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-cyclohexyl)-4-(4-(3-hydroxyoxetan-3-yl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(4-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(4-(3-hydroxyoxetan-3-yl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-(methylsulfonyl)benzamido)propanoyl)-4-(4-((methylsulfonyl)methyl)-1H-1,2,3-triazol-1-yl)pyrrolidine-2-carboxamide;

N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide;

(2S,4S)—N-(1-(2-amino-2-oxoacetyl)cyclohexyl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide;

N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide;

N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide;

(2S,4S)—N-(1-(2-amino-2-oxoacetyl)cyclohexyl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-1-((R)-2-(4-((2-amino-2-oxoethyl)-sulfonyl)benzamido)-3-cyclohexylpropanoyl)-4-(5-(2-hydroxypropan-2-yl)-1H-1,2,3-triazol-1-yl)pyrrolidine-2-carboxamide;

$N^2$—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide;

$N^2$—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(tetracosaoxatriheptacontan-73-yl)naphthalene-2,6-dicarboxamide;

(2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(((methylsulfonyl)methyl)amino)-2-oxoacetyl)-cyclohexyl)pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-oxo-2-((2,2,2-trifluoroethyl)amino)acetyl)cyclohexyl)-pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(oxetan-3-ylamino)-2-oxoacetyl)cyclohexyl)pyrrolidine-2-carboxamide;

(2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(spiro[3.3]heptan-2-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-1-(3-cyclohexyl-2-methyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-4-(5-(2-hydroxypropan-2-yl)-1H-1,2,3-triazol-1-yl)-1-(2-(4-(methylsulfonyl)benzamido)-3-(spiro[3.3]heptan-2-yl)propanoyl)pyrrolidine-2-carboxamide;

(2S,4S)—N-(1-(2-amino-2-oxoacetyl)cyclohexyl)-1-(3-(bicyclo[2.2.1]heptan-1-yl)-2-(4-(methylsulfonyl)benzamido)propanoyl)-4-(5-(2-hydroxypropan-2-yl)-1H-1,2,3-triazol-1-yl)pyrrolidine-2-carboxamide;

benzyl ((R)-2-(2-naphthamido)-3-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-oxopropyl)carbamate;

(2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-acetamidopropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(2-(2-amino-2-oxoacetyl)-spiro[3.3]heptan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-4,4-dimethylcyclohexyl)-4-(5-(2-hydroxypropan-2-yl)-1H-1,2,3-triazol-1-yl)pyrrolidine-2-carboxamide;

(2S,4S)—N-(2-(2-amino-2-oxoacetyl)spiro[3.3]heptan-2-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)-4,4-dimethylcyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide; and (2S,4S)-1-((R)-2-(2-naphthamido)-3-cyclohexylpropanoyl)-N-(6-(2-amino-2-oxoacetyl)-spiro[2.5]octan-6-yl)-4-(5-(2-hydroxypropan-2-yl)-1H-1,2,3-triazol-1-yl)pyrrolidine-2-carboxamide; or a pharmaceutically acceptable salt, solvate, salt of the solvate, or prodrug thereof.

In a twelfth embodiment, the present disclosure provides a pharmaceutical composition comprising a compound of any of the first through the eleventh embodiments, and a pharmaceutically acceptable carrier.

In a thirteenth embodiment, the present disclosure provides a method of preventing, or treating a disease of the eye selected from dry-AMD, wet-AMD, geographic atrophy, diabetic retinopathy, retinopathy of prematurity, polypoidal choroidal vasculopathy, and degeneration of retinal or photoreceptor cells, comprising: administering to a subject in need thereof a therapeutically effective amount of a compound according to any of the first through the eleventh embodiments, or a pharmaceutically acceptable salt, solvate, solvate of the salt or prodrug thereof, or the pharmaceutical composition of the twelfth embodiment.

In a fourteenth embodiment, for the method of the thirteenth embodiment, the method of prevention is selected from delaying the onset of disease and reducing the risk of developing a disease of the eye, wherein the disease of the eye is selected from dry-AMD, wet-AMD, and geographic atrophy, diabetic retinopathy, retinopathy of prematurity, polypoidal choroidal vasculopathy, and degeneration of retinal or photoreceptor cells.

In a fifteenth embodiment, for the method of the thirteenth embodiment the method of treating a disease of the eye is selected from controlling, alleviating, and slowing the progression of, wherein the disease is selected from dry-AMD, wet-AMD, and geographic atrophy, diabetic retinopathy, retinopathy of prematurity, polypoidal choroidal vasculopathy, and degeneration of retinal or photoreceptor cells.

In a sixteenth embodiment, for the method of any one of the thirteenth through the fifteenth embodiments, the disease is geographic atrophy.

In a seventeenth embodiment, the present disclosure provides a method of inhibiting HtrA1 protease activity in an eye, comprising administering to a subject in need thereof a therapeutically effective amount of any one of the compounds of the first through the eleventh embodiments or a pharmaceutically acceptable salt, solvate, solvate of the salt or prodrug thereof, or a pharmaceutical composition of the twelfth embodiment.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

The term "patient" includes mammals such as mice, rats, cows, sheep, pigs, rabbits, goats, horses, monkeys, dogs, cats, and humans.

The term "halo" or "halogen" refers to any radical of fluorine, chlorine, bromine or iodine.

The term "alkyl" refers to a saturated hydrocarbon chain that may be a straight chain or branched chain, containing the indicated number of carbon atoms. For example, $C_{1-6}$alkyl indicates that the group may have from 1 to 6 (inclusive) carbon atoms in it. In some embodiments, an alkyl is a $C_{1-6}$alkyl which represents a straight-chain or branched saturated hydrocarbon radical having 1 to 6 carbon atoms. Examples of alkyl include without limitation methyl, ethyl, n-propyl, isopropyl, n-butyl, isobutyl, sec-butyl, and tert-butyl. The notation "$C_{0-n}$alkyl" indicates the absence of an alkyl moiety, or the presence of an alkyl moiety having 1 to n carbon atoms. Thus, for example, the term "$C_{0-6}$alkyl-$R^5$" indicates that the $R^5$ group is attached directly to the parent moiety, or that there is an intervening alkyl group of 1 to 6 carbon atoms between $R^5$ and the parent moiety; such an intervening group may be, for example, —$CH_2$—, —$CH_2CH_2$—, —$CH(CH_3)$— and —$C(CH_3)_2$—.

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl).

As referred to herein, the term "alkoxy" refers to a group of formula —O-(alkyl). Alkoxy can be, for example, methoxy, ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S-(alkyl). The terms "haloalkoxy" and "thiohaloalkoxy" refer to —O-(haloalkyl) and —S-(haloalkyl), respectively. The term "sulfhydryl" refers to —SH.

The term "aralkyl" refers to an alkyl moiety in which an alkyl hydrogen atom is replaced by an aryl group. One of the carbons of the alkyl moiety serves as the point of attachment of the aralkyl group to another moiety. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Alkenyl groups can include, e.g., vinyl, allyl, 1-butenyl, and 2-hexenyl. In some embodiments, an alkenyl is a $C_{2-6}$alkenyl.

The term "alkynyl" refers to a straight or branched hydrocarbon chain containing the indicated number of carbon atoms and having one or more carbon-carbon triple bonds. Alkynyl groups can include, e.g., ethynyl, propargyl, 1-butynyl, and 2-hexynyl. In some embodiments, an alkynyl is a $C_{2-6}$alkynyl.

The term "heterocycle", "heterocyclyl" or "heterocyclic" as used herein except where noted, represents a stable 4-, 5-, 6- or 7-membered monocyclic- or a stable 6-, 7-, 8-, 9-, 10-, 11-, or 12-membered bicyclic heterocyclic ring system which comprises at least one non-aromatic (i.e. saturated or partially unsaturated) ring which consists of carbon atoms and from one to four, preferably up to three, heteroatoms selected from the group consisting of N, O and S, wherein the nitrogen and sulfur atoms may optionally be oxidized as N-oxide, sulfoxide or sulfone, and wherein the nitrogen atom may optionally be quaternized. A heterocycle can be bonded via a ring carbon atom or, if available, via a ring nitrogen atom. Bicyclic heterocyclic ring systems may be fused, bridged, or spiro bicyclic heterocyclic ring system(s). In some embodiments, heterocyclyl is monocyclic having 4 to 7, preferably 4 to 6, ring atoms, of which 1 or 2 are heteroatoms independently selected from the group consisting of N, O and S. In some embodiments, a heterocyclyl group is bicyclic, and in which case, the second ring may be an aromatic or a non-aromatic ring which consists of carbon atoms and from one to four, preferably up to three, heteroatoms independently selected from the group consisting of N, O and S, or the second ring may be a benzene ring, or a "cycloalkyl", or a "cycloalkenyl", as defined herein. Examples of such heterocyclic groups include, but are not limited to azetidine, chroman, dihydrofuran, dihydropyran, dioxane, dioxolane, hexahydroazepine, imidazolidine, imidazoline, indoline, isochroman, isoindoline, isothiazoline, isothiazolidine, isoxazoline, isoxazolidine, morpholine, oxazoline, oxazolidine, oxetane, piperazine, piperidine, dihydropyridine, tetrahydropyridine, dihydropyridazine, pyran, pyrazolidine, pyrazoline, pyrrolidine, pyrroline, tetrahydrofuran, tetrahydropyran, thiamorpholine, tetrahydrothiophene, thiazoline, thiazolidine, thiomorpholine, thietane, thiolane, sulfolane, 1,3-dioxolane, 1,3-oxazolidine, 1,3-thiazolidine, tetrahydrothiopyran, tetrahydrotriazine, 1,3-dioxane, 1,4-dioxane, hexahydrotriazine, tetrahydro-oxazine, tetrahydropyrimidine, perhydroazepine, perhydro-1,4-diazepine, perhydro-1,4-oxazepine, 7-azabicyclo[2.2.1]heptane, 3-azabicyclo[3.2.0]heptane, 7-azabicyclo[4.1.0]heptane, 2,5-diazabicyclo[2.2.1]heptane, 2-oxa-5-azabicyclo[2.2.1]heptane, tropane, 2-oxa-6-azaspiro[3.3]heptane, dihydrobenzofuran, diydrobenzimidazolyl, dihydrobenzoxazole, and dihydrobenzothiazolyl, and N-oxides or sulfones or sulfoxides thereof.

The term "cycloalkyl" refers to a fully saturated monocyclic, bicyclic, tricyclic or other polycyclic hydrocarbon group having the indicated number of ring carbon atoms. Multicyclic cycloalkyl may be fused, bridged or spiro ring systems. Cycloalkyl groups include, but are not limited to, cyclopropyl, cyclobutyl, cyclopentyl, cyclohexyl, cycloheptyl, cyclooctyl, norbornyl (bicyclo[2.2.1]heptyl), decalinyl, adamantyl, spiropentyl, bicyclo[2.1.0]pentyl, bicyclo[3.1.0]hexyl, spiro[2.4]heptyl, spiro[2.5]octyl, bicyclo[5.1.0]octyl, spiro[2.6]nonyl, bicyclo[2.2.0]hexyl, spiro[3.3]heptyl, bicyclo[4.2.0]octyl, bicyclo[2.2.2]octyl, and spiro[3.5]nonyl. In some embodiments, cycloalkyl is a monocyclic $C_{3-8}$cycloalkyl. In other embodiments, cycloalkyl is a bi- or tricyclic $C_{5-12}$cycloalkyl. In other embodiments, cycloalkyl is a spirocyclic $C_{5-12}$cycloalkyl.

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Cycloalkenyl moieties can include, e.g., cyclopentenyl, cyclohexenyl, cyclohexadienyl, or norbornenyl. In some embodiments, a cycloalkenyl is a $C_{4-10}$cycloalkenyl. In other embodiments, a cycloalkenyl is a $C_{4-6}$cycloalkenyl. In some embodiments, a cycloalkenyl is monocyclic. In some embodiments, a cycloalkenyl is bicyclic.

The term "aryl" as used herein, is intended to mean any stable monocyclic or bicyclic carbon ring of up to 6 members in each ring, wherein at least one ring is aromatic. Examples of aryl include phenyl, naphthyl, tetrahydronaphthyl, indanyl, or biphenyl.

The term "heteroaryl", as used herein except where noted, represents a stable 5-, 6- or 7-membered monocyclic- or stable 9- or 10-membered fused bicyclic ring system which comprises at least one aromatic ring, which consists of carbon atoms and from one to four, preferably up to three, heteroatoms selected from the group consisting of N, O and S wherein the nitrogen and sulfur heteroatoms may optionally be oxidized, and the nitrogen heteroatom may optionally be quaternized. In the case of a "heteroaryl" which is a bicyclic group, the second ring need not be aromatic and need not comprise a heteroatom. Accordingly, bicyclic "heteroaryl" includes, for example, a stable 5- or 6-membered monocyclic aromatic ring consisting of carbon atoms and from one to four, preferably up to three, heteroatoms, as defined immediately above, fused to a benzene ring, or a second monocyclic "heteroaryl", or a "heterocyclyl", a "cycloalkyl", or a "cycloalkenyl", as defined above. Examples of heteroaryl groups include, but are not limited to, benzimidazole, benzopyrazole, benzisothiazole, benzisoxazole, benzofuran, isobenzofuran, benzothiazole, benzothiophene, benzotriazole, benzoxazole, cinnoline, furan, furazan, imidazole, indazole, indole, indolizine, isoquinoline, isothiazole, isoxazole, naphthyridine, oxadiazole, oxazole, phthalazine, pteridine, purine, pyrazine, pyrazole, pyridazine, pyridine, pyrimidine, pyrrole, quinazoline, quinoline, quinoxaline, tetrazole, thiadiazole, thiazole, thiophene, triazine, triazole, benzimidazole, benzothiadiazole, isoindole, pyrrolopyridines, imidazopyridines such as imidazo[1,2-a]pyridine, pyrazolopyridine, pyrrolopyrimidine and N-oxides thereof.

The term "acyl", as used herein, refers to those groups derived from an organic acid by removal of the hydroxy portion of the acid. Accordingly, acyl is meant to include, for example, acetyl, propionyl, butyryl, decanoyl, pivaloyl, benzoyl and the like.

As used herein, the term "fused" refers to a connectivity between two rings in which two adjacent atoms sharing at least one bond (saturated or unsaturated) are common to the rings. For example, in the following structure, rings A and B are fused

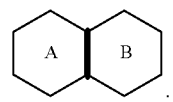

Examples of fused ring structures include, but are not limited to, decahydronaphthalene, 1H-indole, quinolone, chromane, bicyclo[2.1.0]pentane and 6,7,8,9-tetrahydro-5H-benzo[7]annulene.

As used herein, the term "bridged" refers to a connectivity wherein three or more atoms are shared between two rings. The following structures

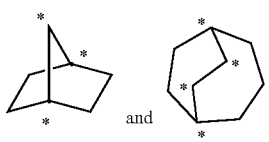

are examples of "bridged" rings because the indicated atoms are shared between at least two rings. Examples of bridged ring structures include, but are not limited to, bicyclo[1.1.1]pentane, 2-oxabicyclo[1.1.1]pentane, 5-azabicyclo[2.1.1]hexane, 6-azabicyclo[3.1.1]heptane, adamantane and norbornane.

As used herein, the term "spiro" refers to a connectivity between two rings wherein the rings have only one atom in common. For example, in the structure

rings C and D are joined by a spiro connection. Examples of spiro connected ring structures include, but are not limited to, spiro[3.3]heptane, 2,6-diazaspiro[3.3]heptane, 2-oxa-6-azaspiro[3.3]heptane, spiro[4.5]decane and 2,6-dioxaspiro[3.3]heptane.

For each of the organic radicals defined above, any atom can be optionally substituted, e.g., by one or more substituents.

Unless otherwise specified, when a bond is depicted in a chemical structure with ～～, it is meant that the bond is located at a stereocenter in which the structure may have either the S or R configuration as understood under the Cahn-Ingold System for naming enantiomers. For example, the ～～ notation can indicate that the bond at the given position can be either a ⫲⫲⫲ or a ／. The presence of the ～～ does not limit the exemplified compound to only a racemate, but can include all possible stereoconfigurations.

The term "treating", "treat", or "treatment" refers generally to controlling, alleviating, ameliorating, slowing the progress of or eliminating a named condition once the condition has been established. In addition to its customary meaning, the term "preventing", "prevent", or "prevention" also refers to delaying the onset of, or reducing the risk of developing a named condition or of a process that can lead to the condition, or the recurrence of symptoms of a condition.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

Compound Forms and Salts

The compounds of this disclosure may contain one or more asymmetric centers and thus occur as racemates and racemic mixtures, enantiomerically enriched mixtures, single enantiomers, individual diastereomers and diastereomeric mixtures. The compounds of the present disclosure may, either by nature of asymmetric centers or by restricted rotation, be present in the form of isomers (e.g., enantiomers, diastereomers).

It will also be appreciated that when two or more asymmetric centers are present in the compounds of the disclosure, several diastereomers and enantiomers of the exemplified structures will often be possible, and that pure diastereomers and pure enantiomers represent preferred embodiments. It is intended that pure stereoisomers, pure diastereomers, pure enantiomers, and mixtures thereof, are within the scope of the disclosure.

All isomers, whether separated, pure, partially pure, or in racemic mixture, of the compounds of this disclosure are encompassed within the scope of this disclosure. The purification of said isomers and the separation of said isomeric mixtures may be accomplished by standard techniques known in the art. For example, diastereomeric mixtures can be separated into the individual isomers by chromatographic processes or crystallization, and racemates can be separated into the respective enantiomers either by chromatographic processes on chiral phases or by resolution.

The compounds of the present disclosure include all cis, trans, syn, anti, entgegen (E), and zusammen (Z) isomers as well as mixtures thereof. The compounds of the present disclosure may also be represented in multiple tautomeric forms, in such instances, the present disclosure expressly includes all tautomeric forms of the compounds described herein, even though only a single tautomeric form may be represented. In addition, where a term used in the present disclosure encompasses a group that may tautomerize, all tautomeric forms are expressly included thereunder. For example, hydroxy substituted heteroaryl includes 2-hydroxypyridine as well as 2-pyridone, 1-hydroxyisoquinoline as well as 1-oxo-1,2-dihyroisoquinoline, 4-hydroxyquinazoline as well as 4-oxo-3,4-dihydroquinazoline, and the like. All such isomeric forms of such compounds are expressly included in the present disclosure.

The compounds of the present disclosure include the compounds themselves, as well as their salts, solvate, solvate of the salt and their prodrugs, if applicable. Salts for the purposes of the present disclosure are preferably pharmaceutically acceptable salts of the compounds according to the present disclosure. Salts which are not themselves suitable for pharmaceutical uses but can be used, for example, for isolation or purification of the compounds according to the disclosure are also included. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion.

As used herein, "pharmaceutically acceptable salts" refer to derivatives wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. When the compound of the present disclosure is basic, pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfonic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, benzenesulfonic, toluenesulfonic, naphthalenedisulfonic, methanesulfonic, ethanesulfonic, ethanedisulfonic, camphorsulfonic, gluconic, mandelic, mucic, pantothenic, oxalic, isethionic, and the like.

When the compound of the present disclosure is acidic, salts may be prepared from pharmaceutically acceptable non-toxic bases, including inorganic and organic bases. Such salts that may be prepared include lithium salt, sodium salt, potassium salt, magnesium salt, calcium salt, dicyclohexylamine salt, N-methyl-D-glucamine salt, tris(hydroxymethyl)methylamine salt, arginine salt, lysine salt, and the like.

Lists of suitable salts may be found in Remington's Pharmaceutical Sciences, 17th ed., Mack Publishing Company, Easton, Pa., 1985, p. 1418; S. M. Berge et al., "Pharmaceutical Salts", J. Pharm. Sci. 1977, 66, 1-19; and "Pharmaceutical Salts: Properties, Selection, and Use. A Handbook"; Wermuth, C. G. and Stahl, P. H. (eds.) Verlag Helvetica Chimica Acta, Zurich, 2002 [ISBN 3-906390-26-8]; each of which is incorporated herein by reference in its entirety.

Solvates in the context of the present disclosure are designated as those forms of the compounds according to the present disclosure which form a complex in the solid or liquid state by stoichiometric coordination with solvent molecules. Hydrates are a specific form of solvates, in which the coordination takes place with water. Hydrates are preferred solvates in the context of the present disclosure. The formation of solvates is described in greater detail in "Solvents and Solvent Effects in Organic Chemistry"; Reichardt, C. and Welton T.; John Wiley & Sons, 2011 [ISBN: 978-3-527-32473-6], the contents of which is incorporated herein by reference in its entirety. A person of ordinary skill in the art would recognize the solvates of the present disclosure.

The present disclosure also encompasses all suitable isotopic variants of the compounds according to the present disclosure, whether radioactive or not. An isotopic variant of a compound according to the present disclosure is understood to mean a compound in which at least one atom within the compound according to the present disclosure has been exchanged for another atom of the same atomic number, but with a different atomic mass than the atomic mass which usually or predominantly occurs in nature. Examples of isotopes which can be incorporated into a compound according to the present disclosure are those of hydrogen, carbon, nitrogen, oxygen, fluorine, chlorine, bromine and iodine, such as $^2$H (deuterium), $^3$H (tritium), $^{13}$C, $^{14}$C, $^{15}$N, $^{17}$O, $^{18}$O, $^{18}$F, $^{36}$Cl, $^{82}$Br, $^{123}$I, $^{124}$I, $^{125}$I, $^{129}$I and $^{131}$I. Particular isotopic variants of a compound according to the present disclosure, especially those in which one or more radioactive isotopes have been incorporated, may be beneficial, for example, for the examination of the mechanism of action or of the active compound distribution in the body. Due to comparatively easy preparability and detectability, especially compounds labelled with $^3$H, $^{14}$C and/or $^{18}$F isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required. Such modifications of the compounds according to the present disclosure may therefore in some cases also constitute a preferred embodiment of the present disclosure. In some embodiments, hydrogen atoms of the compounds described herein may be replaced with deuterium atoms. Isotopic variants of the compounds according to the present disclosure can be prepared by processes known to those skilled in the art, for example by the methods described below and the methods described in the working examples, by using corresponding isotopic modifications of the particular reagents and/or starting compounds therein.

The present disclosure includes within its scope prodrugs of the compounds of Formula I. Prodrugs are generally drug precursors that, following administration to a subject are converted to an active, or a more active species via some process, such as conversion by chemical hydrolysis or a metabolic pathway. Thus, in the methods of treatment of the present disclosure, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985 (Amsterdam, NL). Examples of prodrugs include $C_{1-6}$ alkyl esters of carboxylic acid groups and esters of boronic acids, which, upon administration to a subject, are capable of providing active compounds.

Esters of boronic acids are illustrated by Formula II:

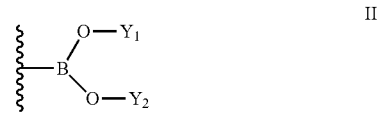

wherein:

$Y_1$ and $Y_2$ are each independently selected from hydrogen, optionally substituted $C_{1-6}$alkyl, $C_{3-10}$cycloalkyl, $C_{1-6}$heterocycle, aryl and heteroaryl, or $Y_1$ and $Y_2$ are joined together to form the group

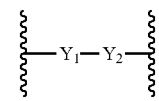

which represents an optionally substituted $C_{2-6}$alkyl in which a carbon atom may be replaced by O, S or —(NCH$_3$)—, optionally substituted $C_{5-12}$cycloalkyl, optionally substituted heterocycle, optionally substituted aryl or optionally substituted heteroaryl. The optional substituents include, for example, hydroxyl, halogen and $C_{1-3}$alkoxy. As will be appreciated by one of skill in the art, for each of the moieties shown herein, a squiggly line describes the point at which the moiety shown is attached to the parent molecule. Illustrating the boronic acid esters are:

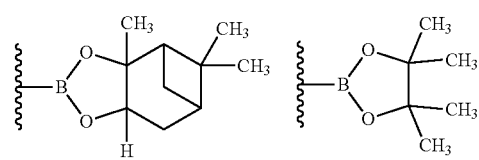

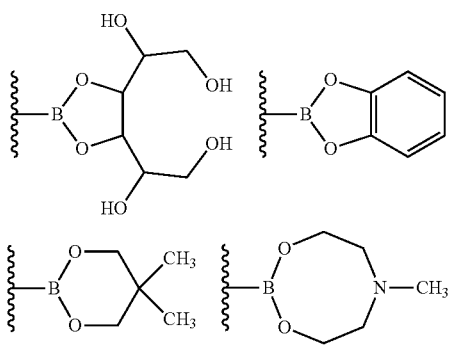

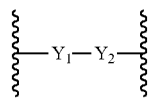

wherein $Y_1$ and $Y_2$ forms an optionally substituted $C_{2-6}$alkyl, or an optionally substituted heterocycle. The optional substituents include, for example, hydroxyl, halogen and $C_{1-3}$alkoxy;

$Y_3$ is H, $C_{1-4}$alkyl, OH or O—$C_{1-4}$alkyl.

Illustrating the ketone prodrugs are:

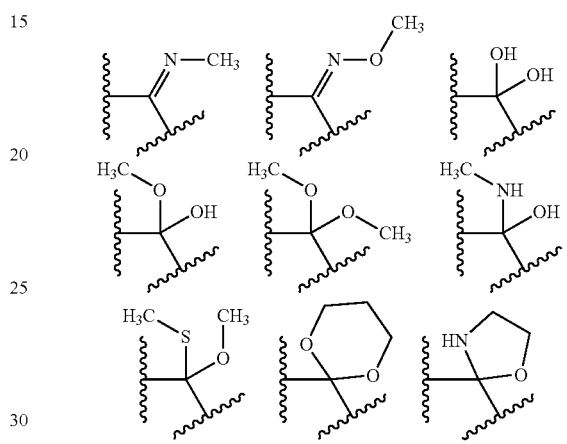

$Y_1$ and $Y_2$ can also represent —B—O—B— to form a 6-membered trioxatriborinane or —B— to form a 4-membered dioxadiboretane.

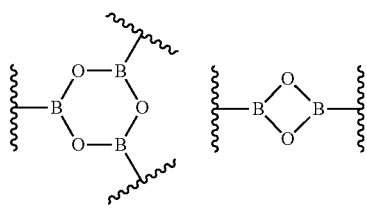 [SMILES: *B1OB(*)OB(*)O1 ; *B1OB(*)O1]

In some embodiments, where W of Formula I is —C(O)C(O)NR$^7$R$^8$ (ketoamides), compounds of Formula I may be prepared as prodrugs. Examples of ketone prodrugs include but are not limited to ketimine, oxime, aminal, ketal, hemiaminal, hemiketal, thioketal, hydrated ketone which, upon administration to a subject, are capable of providing active compounds. Carbonyl derivatives of ketoamides are illustrated by Formula IIIa and IIIb:

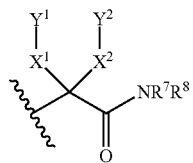
IIIa

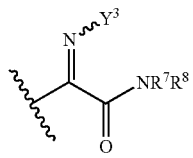
IIIb wherein:

$X_1$ and $X_2$ are each independently selected from O, N and S;

$Y_1$ and $Y_2$ are each independently selected from hydrogen, optionally substituted $C_{1-6}$alkyl, $C_{3-10}$cycloalkyl, $C_{1-6}$heterocycle, or $Y_1$ and $Y_2$ are joined together to form the group:

Pharmaceutical Compositions

The term "pharmaceutical composition" as used herein is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure, or a pharmaceutically acceptable salt, or solvate or solvate of the salt thereof, and a pharmaceutically acceptable carrier.

The term "pharmaceutically acceptable carrier" refers to a carrier or an adjuvant that may be administered to a patient, together with a compound of the present disclosure, or a pharmaceutically acceptable salt, solvate, salt of the solvate or prodrug thereof, and which does not destroy the pharmacological activity thereof and is nontoxic when administered in doses sufficient to deliver a therapeutic amount of the compound.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. For convenience, the total daily dosage may be divided and administered in portions during the day if desired.

Pharmaceutical compositions of the present disclosure for injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and non-aqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These pharmaceutical compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin. If desired, and for more effective distribution, the compounds can be incorporated into slow release or targeted delivery systems such as polymer matrices, liposomes, and microspheres.

The pharmaceutical compositions that are injectable formulations can be sterilised, for example, by filtration through a bacterial-retaining filter, or by incorporating sterilising agents in the form of sterile solid pharmaceutical compositions that can be dissolved or dispersed in sterile water or other sterile injectable medium just prior to use.

Solid dosage forms of the instant pharmaceutical compositions for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of the instant pharmaceutical compositions of tablets, dragees, capsules, pills, and granules can be prepared with coatings and shells such as enteric coatings and other coatings well known in the pharmaceutical formulating art. They may optionally contain opacifying agents and can also be of a formulation that they release the active ingredient(s) only, or preferentially, in a certain part of the intestinal tract, optionally, in a delayed manner. Examples of embedding pharmaceutical compositions which can be used include polymeric substances and waxes.

The active compounds can also be in microencapsulated form, if appropriate, with one or more of the above-mentioned excipients.

Liquid dosage forms of the instant pharmaceutical compositions for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral pharmaceutical compositions can also include adjuvants such as wetting agents, emulsifying and suspending agents, sweetening, flavouring, and perfuming agents.

Suspensions of the instant compounds, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Pharmaceutical compositions for rectal or vaginal administration are preferably suppositories which can be prepared by mixing the compounds with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound or pharmaceutical composition of the present disclosure include powders, patches, sprays, ointments and inhalants. The active compound is mixed under sterile conditions with a pharmaceutically acceptable carrier and any needed preservatives, buffers, or propellants which may be required.

Dosage forms for application to the eye include solutions, suspensions, ointments, gels, emulsions, strips, inserts such as contact lenses, and implants, which may be administered topically, intravitreally, perioccularly, and the like.

Uses

The present disclosure is directed to novel carbocyclic prolinamide derivatives of Formula I, and pharmaceutically acceptable salts, solvates, salts of solvates and prodrugs thereof, useful in the prevention (e.g., delaying the onset of or reducing the risk of developing) and treatment (e.g., controlling, alleviating, or slowing the progression of) of age-related macular degeneration (AMD) and related diseases of the eye. These diseases include dry-AMD, wet-AMD, geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells.

The present disclosure disclosed herein is further directed to methods of prevention, slowing the progress of, and treatment of dry-AMD, wet-AMD, and geographic atrophy, diabetic retinopathy, retinopathy of prematurity, polypoidal choroidal vasculopathy, diabetic macula edema (DME), other retinopathies such as choroidal neovascularisation (CNV), choroidal neovascular membrane (CNVM), cystoid macular edema (CME), epi-retinal membrane (ERM) and macular hole, hypertrophic changes of the retinal pigment epithelium (RPE), atrophic changes of the retinal pigment epithelium, retinal detachment, choroidal vein occlusion, retinal vein occlusion, corneal angiogenesis following, for example, keratitis, cornea transplantation or keratoplasty, corneal angiogenesis due to hypoxia (e.g., induced by extensive contact lens wearing), pterygium conjunctivae, subretinal edema, intraretinal edema, Stargardt disease and degeneration of retinal or photoreceptor cells, comprising: administration of a therapeutically effective amount of compound of the present disclosure. The compounds of the present disclosure are inhibitors of HTRA1. Thus, the compounds of the present disclosure are useful in the prevention and treatment of a wide range diseases mediated (in whole or in part) by HTRA1. The compounds of the present disclosure are also useful for inhibiting HTRA1 protease activity in an eye and elsewhere. By virtue of their activity profile, the compounds of the present disclosure are particularly suitable for the treatment and/or prevention of ocular disorders, such as age-related macular degeneration (AMD) like wet-AMD or dry-AMD, geographic atrophy, diabetic retinopathy, Stargardt disease, choroidal neovascularisation (CNV), and diabetic macula edema (DME).

Additionally, compounds of the present disclosure may be useful in the treatment of other diseases in which HTRA1 may be involved, including retinal angiomatous proliferation, foveomacular proliferation, musculoskeletal diseases, including osteoarthritis, spinal disk degeneration rheumatoid arthritis, muscular dystrophy and osteoporosis, and treatment of autologous chondrocytes prior to intraarticular implantation.

Administration

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug, dosage form, and/or route of administration. The interrelationship of dosages for animals and humans (based on milligrams per meter squared of body surface) is described by Freireich et al., Cancer Chemother. Rep. 50, 219-244 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or by injection. The methods herein contemplate administration of an effective amount of compound or compound composition to achieve the desired or stated effect. Typically, the pharmaceutical compositions of the present disclosure will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, and the judgment of the treating physician.

Dosage forms include from about 0.001 milligrams to about 2,000 milligrams (including, from about 0.001 milligrams to about 1,000 milligrams, from about 0.001 milligrams to about 500 milligrams, from about 0.01 milligrams to about 250 milligrams, from about 0.01 milligrams to about 100 milligrams, from about 0.05-milligrams to about 50 milligrams, and from about 0.1 milligrams to about 25 milligrams) of a compound of Formula I (and/or a compound of any of the other formulae described herein) or a salt (e.g., a pharmaceutically acceptable salt) thereof as defined anywhere herein. The dosage forms can further include a pharmaceutically acceptable carrier and/or an additional therapeutic agent.

With regard to ophthalmic preparation, because AMD and related diseases (including dry-AMD, wet-AMD, geographic atrophy, diabetic retinopathy, retinopathy of prematurity, polypoidal choroidal vasculopathy, and degeneration of retinal or photoreceptor cells) primarily afflict the back of the eye, local administration such as topical administration, trans-scleral drug delivery and intravitreal administration may be preferable over systemic administration. Intravitreal administration can be further divided into intravitreal injection and intravitreal implants. Of these, intravitreal injection appears to be the most widely used. Products utilizing intravitreal injection include Trivaris® (triamcinolone acetonide), Triescence® (triamcinolone acetonide, Alcon Fort Worth, Tex.), Macugen® (pegaptanib sodium, Bausch and Lomb, Rochester, N.Y.), Lucentis® (ranibizumab injection, Genentech, South San Francisco, Calif.), Ozurdex® (dexamethasone, Allergan, Inc., Irvine, Calif.) and Iluvien® (flucinolone acetonide, Alimera Sciences, Alpharetta, Ga.). The preferred dosage range for local administration to the back of the eye ranges from 0.001 mg to 100 mg (including from about 0.01 milligrams to about 500 milligrams, from about 0.05 milligrams to about 250 milligrams, from about 0.05 milligrams to about 100 milligrams, from about 0.1 milligrams to about 50 milligrams, from about 0.1 milligrams to about 25 milligrams, and from about 0.1 milligrams to about 10 milligrams). References on the subject of ophthalmic drug delivery include:

Kompella U. B. et al., Recent Advances in Ophthalmic Drug Delivery, Ther. Deliv. 2010 1(3): 435-456;

Gaudana R. et al., Ocular Drug Delivery, AAPS Journal, Vol. 12, No. 3: 348-360 (2010);

Haghjou N. et al., Sustained Release Intraocular Drug Delivery Devices for Treatment of Uveitis, J. Ophthalmic Vis. Res. 2011; 6 (4): 317-329;

Kuno N. and Fujii S. Recent Advances in Ocular Drug Delivery Systems, Polymers (2011), 3:193-221;

Patel A. et al., Ocular Drug Delivery Systems: An Overview, World J. Pharmacol. (2013) 2:47-64;

Morrison P. W. J. and Khutoryanskiy V. V. Advances in Ophthalmic Drug Delivery, Ther. Deliv. (2014) 5:1297-1315;

Chen H. Recent Developments in Ocular Drug Delivery, J. Drug Target (2015), 23:597-604; all of which are incorporated by reference.

For the treatment and/or prevention of ocular disorders, as described above, the preferred route for administering the compounds of the present disclosure is topically at the eye or by an ocular drug delivery system. Intraocular injections are another way to administer the compounds of the present disclosure that is suitable for such purposes.

Delivery to areas within the eye can be accomplished by injection, employing a cannula or another invasive device designed to introduce precisely metered amounts of a desired formulation to a particular compartment or tissue within the eye (e.g., posterior chamber or retina). An intraocular injection may be into the vitreous (intravitreal), under the conjunctiva (subconjunctival), behind the eye (retrobulbar), into the sclera, or under the Capsule of Tenon (sub-Tenon), and may be in a depot form. Other intraocular routes of administration and injection sites and forms are also contemplated and are within the scope of the present disclosure.

The compounds according to the present disclosure may be formulated in a manner known to those skilled in the art so as to give adequate delivery to the back of the eye, which may be by regular dosing, such as with eye drops, or by using a delivery system to give a controlled release, such as slow release, of the compounds according to the present disclosure.

Preferred ocular formulations for the compounds of the present disclosure include aqueous solutions, suspensions or gels of these compounds in the form of drops of liquid, liquid washes, sprays, ointments or gels, in a mixture with excipients suitable for the manufacture and use of such application forms. Alternatively, the compounds of the present disclosure may be applied to the eye via liposomes or other ocular delivery systems that are known in the art.

Appropriate dosage levels may be determined by any suitable method known to one skilled in the art of treating eye diseases. Preferably, the active substance is administered at a frequency of 1 to 4 times per day for topical administration, or less often if a drug delivery system is used. Typically, an ocular formulation intended for topical application contains the active ingredient in a concentration range of about 0.001% to 10%.

Nevertheless, actual dosage levels and time course of administration of the active ingredients in the pharmaceutical compositions of the present disclosure may be varied so as to obtain an amount of the active ingredient which is effective to achieve the desired therapeutic response for a particular patient, composition and mode of administration, without being toxic to the patient. It may therefore be necessary where appropriate to deviate from the stated amounts, in particular as a function of age, gender, body weight, diet and general health status of the patient, route of administration, individual response to the active ingredient, nature of the preparation, and time or interval over which administration takes place. Thus, it may be satisfactory in some cases to manage with less than the aforementioned minimum amount, whereas in other cases the stated upper limit must be exceeded. It may in the event of administration of larger amounts be advisable to divide these into multiple individual doses spread over the day.

In one aspect the compounds of the present disclosure may be co-administered with one or more additional agents. The additional agents include, but are not limited to Acuvail® (ketorolac tromethamine ophthalmic solution), AK-Con-A®/OcuHist® (pheniramine maleate-naphazoline HCl, ophthalmic solution), Akten® (lidocaine HCl ophthalmic gel), Alamast® (pemirolast potassium ophthalmic solution), Alphagan® (brimonidine tartrate ophthalmic solution), Bepreve® (bepotastine besilate ophthalmic solution), Besivance® (besifloxacin ophthalmic suspension), Betaxon® (levobetaxolol HCl ophthalmic suspension), Cosopt® (dorzolamide HCl—timolol maleate, ophthalmic solution), Cystaran® (cysteamine HCl ophthalmic solution), Durezol® (difluprednate ophthalmic emulsion), Eylea® (aflibercept intravitreal injection), Jetrea® (ocriplasmin intravitreal injection), Lotemax® (loteprednol etabonate ophthalmic suspension), Lucentis® (ranibizumab injection), Lumigan® (bimatoprost ophthalmic solution), Macugen® (pegaptanib intravitreal injection), Ocuflox® (ofloxacin ophthalmic solution), Omidria® (phenylephrine and ketorolac injection), Ozurdex® (dexamethasone intravitreal implant), Quixin® (levofloxacin ophthalmic solution), Rescula® (unoprostone isopropyl ophthalmic solution 0.15%), Restasis® (cyclosporine ophthalmic emulsion), Salagen® (pilocarpine HCl tablets), Travatan® (travoprost ophthalmic solution), Valcyte® (valganciclovir HCl tablets and oral solution), Vistide® (cidofovir tablets), Visudyne® (verteporfin injection), Vitrasert® (ganciclovir implant), Vitravene® (fomivirsen injection), Zioptan® (tafluprost ophthalmic solution), Zirgan® (ganciclovir ophthalmic gel), and Zymaxid® (gatifloxacin ophthalmic solution). Furthermore the compounds of the disclosure may be co-administered with one or more inhibitors of VEGF-mediated angiogenesis, such as, for example, ACTB-1003 (Edding Pharm, CN), apatinib, axitinib, bevacizumab, bevasiranib, BMS-690514 (Bristol-Myers Squibb (BMS), NY), brivanib, cediranib, CT-322 (Adnexus/BMS, MA), dovitinib, lenvatinib, foretinib, KH-902/conbercept (approved in CN for exudative macular degeneration), linifanib, MGCD-265 (Mirati Therapeutics, CA), motesanib, elpamotide, pazopanib, pegaptanib, ranibizumab, regorafenib, ruboxystaurin, sorafenib, SU-14813 (Pfizer, CT), sunitinib, telatinib, TG-100801, tivozanib, TSU-68 (Taiho Pharmaceuticals, JP), vandetanib, vargatef, vatalanib and Carbometyx® (cabozantinib tablets, Exelixis, CA), or with inhibitors of other signaling pathways, such as disulfiram, fenretinide, mecamylamine, PF-04523655 (Pfizer, CT), sonepcizumab, tandospirone and volociximab.

Additional agents which may be utilized for co-administration include: known vitamins and antioxidants such as AREDS/AREDS2 (supplements used in Age-Related Eye Disease Study/Study 2, National Eye Institute, US), omega-3 fatty acids, lutein, zeaxanthin, vitamin A; visual-cycle modulators such as emixustat (ACU-4429, Acucela, WA); anti-inflammatory agents such as Illuvien® (fluocinolone acetonide), sirolimus, Triesence®/Trivaris® (triamcinolone acetonide); complement modulators such as lampalizumab, Soliris® (eculizumab, Alexion, CT); amyloid-modulators such as GSK933776 (GlaxosmithKline, PA), RN6G (PF-04382923, Pfizer, CT) and platelet-derived growth factor modulators such as, for example, Fovista® (pegpleranib, Ophthotech, NY).

In certain embodiments, the additional agents may be administered separately (e.g., sequentially; on different overlapping schedules), as part of a multiple dose regimen, from the compounds of the present disclosure (e.g., one or more compounds of Formula (I) and/or a compound of any of the other formulae, including any subgenera or specific compounds thereof). In other embodiments, these agents may be part of a single dosage form, mixed together with the compounds of the present disclosure in a single composition. In still another embodiment, these agents can be given as a separate dose that is administered at about the same time as that of one or more compounds of Formula (I) (and/or a compound of any of the other formulae, including any subgenera or specific compounds thereof) are administered (e.g., simultaneously with the administration of one or more compounds of Formula (I) (and/or a compound of any of the other formulae, including any subgenera or specific compounds thereof)). When the compositions of the present disclosure include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of the present disclosure may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions of the present disclosure may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase and then combined with emulsifying and/or suspending agents. If desired, certain sweetening and/or flavoring and/or coloring agents may be added.

Biological Function

The utility of the present disclosure can be demonstrated by one or more of the following methods or other methods known in the art:

Full Length HTRA1 Assay

Serial dilutions (1/3) from 1000 µM down to 0.051 µM of test compounds were prepared in dimethyl sulfoxide (DMSO). Then 2 µL of solution from each dilution were added to 100 µL of 4 nM full-length human His-HTRA1 in assay buffer (50 mM Tris, pH 7.5, 200 mM NaCl and 0.25% 3-[(3-cholamidopropyl)dimethylammonio]-1-propanesulfonate or CHAPS) in white non-binding 96-well plates. The assay solutions were mixed for 5 seconds on a shaker plate and incubated for 10 minutes at room temperature. Mca-H2OPT (Mca-Ile-Arg-Arg-Val-Ser-Tyr-Ser-Phe-Lys(Dnp)-Lys-OH trifluoroacetate salt) (Mca=7-methoxycoumarin-4-acetic acid; Dnp=dinitrophenyl) (5 µM) in 100 µL of assay buffer was added to the assay solutions. The reaction mixture was shaken for 5 seconds on a shaker plate and cleavage of Mca-H2OPT was monitored by spectrofluorometry (SpectraMax M3 by Molecular Devices, CA) for 10 minutes (Exλ=330 nm; Emλ=420 nm). Percent inhibition was calculated by fitting values to a standard mathematical model for determining the dose response curve.

| Example | HtrA1 IC$_{50}$ (µM) |
|---|---|
| 1 | 0.261 |
| 2 | 2.91 |

-continued

| Example | HtrA1 IC$_{50}$ (µM) |
|---|---|
| 3 | 0.0472 |
| 4 | 0.00562 |
| 5 | 0.00908 |
| 6 | 0.675 |
| 7 | 0.138 |
| 8 | 0.0125 |
| 9 | 0.199 |
| 10 | 0.0181 |
| 11 | 0.00982 |
| 12 | 0.0811 |
| 13 | 0.0172 |
| 14 | 0.0156 |
| 15 | 0.046 |
| 16 | 0.155 |
| 17 | 0.0201 |
| 18 | 0.0244 |
| 19 | 0.157 |
| 20 | 0.0901 |
| 21 | 0.142 |
| 22 | 0.0403 |
| 23 | 0.0596 |
| 24 | 0.0138 |
| 25 | 0.0368 |
| 26 | 0.0216 |
| 27 | 0.0374 |
| 28 | 0.0553 |
| 29 | 0.0631 |
| 30 | 0.303 |
| 31 | 0.144 |
| 32 | 0.146 |
| 33 | 0.11 |
| 34 | 0.62 |
| 35 | 0.223 |
| 36 | 0.00665 |
| 37 | 0.0104 |
| 38 | 0.523 |
| 39 | 0.0305 |
| 40 | 0.0252 |
| 41 | 0.068 |
| 42 | 0.606 |
| 43 | 1.18 |
| 44 | 0.0223 |
| 45 | 0.0385 |
| 46 | 0.181 |
| 47 | 0.0782 |
| 48 | 0.011 |

Synthesis

The starting materials used for the synthesis are either synthesized or obtained from commercial sources, such as, but not limited to, Sigma-Aldrich, Fluka, Acros Organics, Alfa Aesar, VWR Scientific, Chem-Impex, PharmaBlock, Combi-Blocks, Astatech, Enamine and the like. Nuclear Magnetic Resonance (NMR) analysis was conducted using a Varian Mercury 300 MHz spectrometer with an appropriate deuterated solvent. LCMS analysis was conducted using a Waters Acquity UPLC with a QDA MS detector using a Waters C18 BEH 1.7 M, 2.1×50 mm column, eluting with 95:5 to 0:100 H$_2$O:MeCN+0.1% formic acid at a flow rate of 0.6 mL/min over 3.5 minutes. The QDA MS detector was set up to scan under both positive and negative mode ions ranging from 100-1200 Daltons. General methods for the preparation of compounds can be modified by the use of appropriate reagents and conditions for the introduction of the various moieties found in the structures as provided herein.

Abbreviations

Boc tert-butyl carbonate
Bn Benzyl

C celcius
CBz carboxybenzyl
m-CPBA meta-chloroperoxybenzoic acid
DBU 1,8-Diazabicyclo[5.4.0]undec-7-ene
DCM Dichloromethane
DMP Dess-Martin periodinane
DMF dimethylformamide
DMSO dimethylsulfoxide
EtOAc ethyl acetate
Et ethyl
equiv equivalents
h hours
HATU 1-[bis(dimethylamino)methylene]-1H-1,2,3-triazolo[4,5-b]pyridinium 3-oxid hexafluorophosphate
PyAOP (7-Azabenzotriazol-1-yloxy)tripyrrolidinophosphonium hexafluorophosphate
g grams
L liter
LDA lithium diisopropylamide
LAH lithium aluminum hydride
LCMS liquid chromatography-mass spectrometry
liq. liquid
M molar
Ms methanesulfonyl
Me methyl
MeCN acetonitrile
mg milligrams
mL milliliter
mmol millimoles
mol moles
MS mass spectrometry
Pr (iPr) propyl (isopropyl)
sat. saturated
THF tetrahydrofuran
TLC thin layer chromatography (normally silica gel based)
TEA triethylamine
TFA trifluoroacetic acid
Tf$_2$O triflic anhydride
L microliter
UHP urea hydrogen peroxide General Synthetic Scheme In some embodiments, compounds described herein are prepared as outlined in the following general synthetic schemes. These compounds may be viewed as consisting of four units as shown in the general structure: A—the $R^1$—C(O) group, B—an α-amino acyl group, C—the prolyl group, and D—an aminocarbocyclic group. All the variables in the general structure and in the synthetic schemes are, unless otherwise specified, as defined in the claims.

General Structure

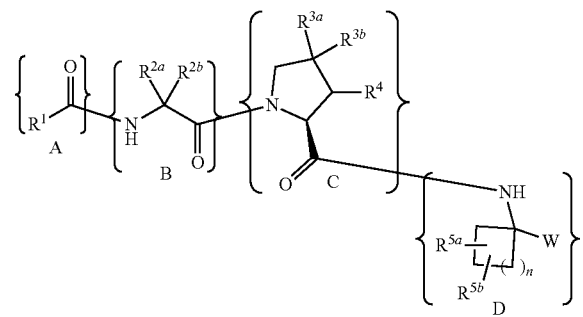

In the schemes, unless otherwise specified, PG is a conventional protecting group (e.g., BOC or CBz for amino group, alkyl ester for carboxylic or boronic acid group); LG is a leaving group (e.g., methanesulfonyloxy); Nuc is a nucleophile (e.g., $N_3$ or piperidine); and R is a protecting group or one or more of optionally protected A, B, C, D units.

Method A: Synthesis of 1-amino 2-hydroxyacetamides

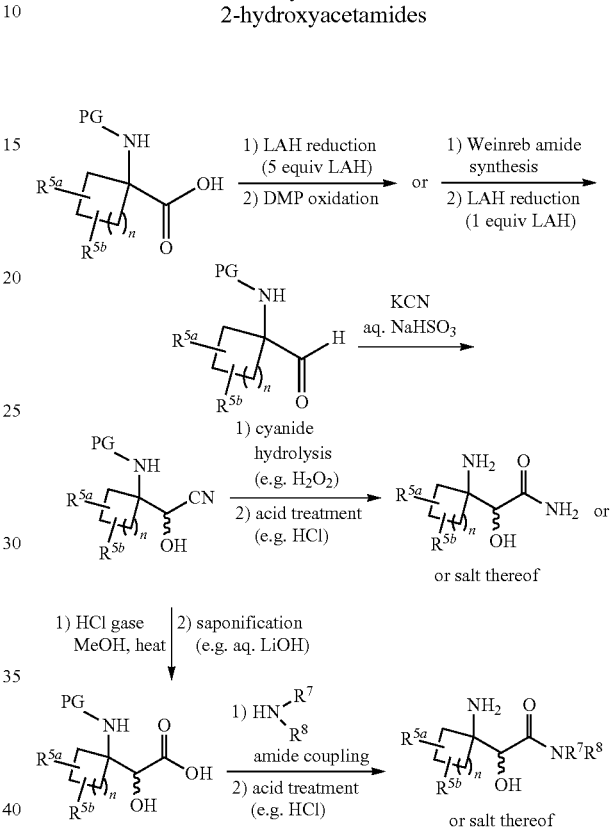

An α-amino acid (commercially available, or otherwise prepared from corresponding ketone using the following literature procedure: Naydenova, E. D., et al. *Eur. J. Med. Chem.* 2008, 43, 1199-1205) is reduced to primary alcohol using excess amount of LAH, which is then oxidized to an aldehyde via DMP oxidation. Alternatively, the α-amino acid can be coupled with N,O-dimethylhydroxylamine via amide coupling conditions described in the literature (e.g. Valeur, E., et al. *Chem. Soc. Rev.* 2009, 38, 606-631), yielding a Weinreb amide, which is reacted with 1 equiv LAH to afford the α-amino aldehyde. The resulting α-amino aldehyde is reacted with KCN under aqueous acidic condition (such as aq. NaHSO$_3$) to give 1-amino 2-hydroxycyanide. The cyanide is hydrolyzed to a hydroxyacetamide via oxidative conditions (such as hydrogen peroxide or urea hydrogen peroxide (UHP)). The subsequent N-protected 1-amino 2-hydroxyacetamide is converted to 1-amino 2-hydroxyacetamide or salt thereof by treatment with a strong acid (such as HCl).

Alternatively, the 1-amino 2-hydroxycyanide is treated with excess strong acid (such as HCl gas) in the presence of methanol at elevated temperatures to afford an α-hydroxyl carboxylic ester, which can then be hydrolyzed to the corresponding carboxylic acid under aqueous basic condition (such as aq. 1 M LiOH). The resulting α-hydroxyl carboxylic acid can be coupled with various amines using literature procedures (e.g. Valeur, E., et al. *Chem. Soc. Rev.* 2009, 38, 606-631). Deprotection of the amine under acidic conditions results in 1-amino 2-hydroxyacetamides or salts thereof.

Method B: Synthesis of α-Amino Boronates

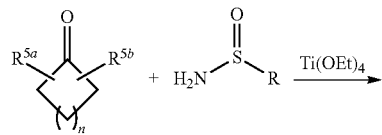

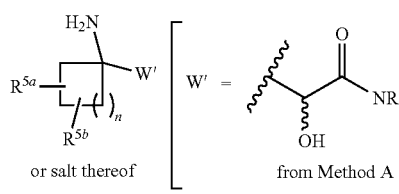

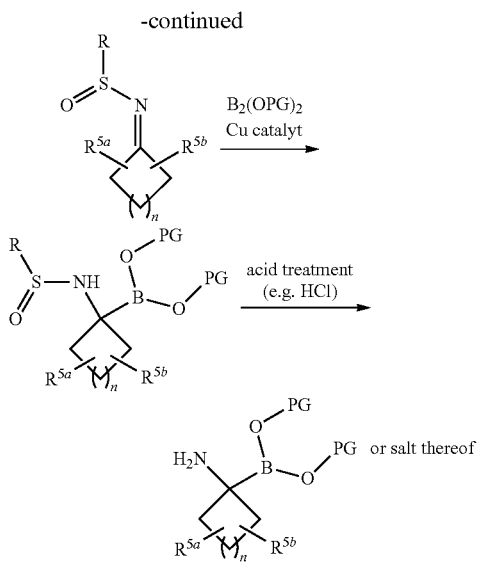

N-Sulfinylimine is prepared via a titanium-mediated imine formation reaction between ketones and sulfinamides (such as 2-methylpropane-2-sulfinamide) as described in the literature (e.g. Ruano, J. L. G., et al. *Org. Lett.* 2005, 7, 179-182). The resulting N-sulfinylimine is reacted with a bis diboron compound (such as bis(pinacolato)diboron, $B_2pin_2$) through a copper(II)-catalyzed imine borylation reaction following a literature procedure (e.g. Buesking, A. W., et al.

*J. Org. Chem.* 2014, 79, 3671-3677). The subsequent N-sulfinyl α-amino boronate is converted to α-amino boronate or salt thereof by treatment with a strong acid (such as HCl).

Method C: Amide coupling with 1-amino 2-hydroxyacetamides or α-amino boronates

The prepared 1-amino 2-hydroxyacetamide from Method A or α-amino boronates from Method B can be attached to the proline residue using standard amide coupling conditions described in the literature (e.g. Valeur, E., et al. *Chem. Soc. Rev.* 2009, 38, 606-631). The proline acid may be protected at the nitrogen (e.g. Boc, Cbz) or may be further functionalized with an α-amino acid or derivative.

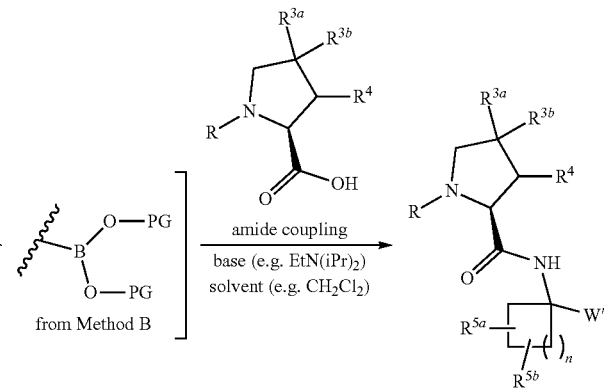

Method D: Synthesis of 4-Substituted Proline Analogs Via Nucleophilic Displacement The alcohol moiety of a 4-hydroxyproline analog can be converted into a suitable leaving group (e.g. mesylate) under standard conditions and then reacted in the presence of a suitable nucleophile (e.g. amine, azide) in the presence of a base (e.g. $Et_3N$ or NaH) to afford a 4-substituted proline derivative. The proline may be protected at the proline nitrogen (e.g. Boc, Cbz) or may be further functionalized with an α-amino acid or derivative.

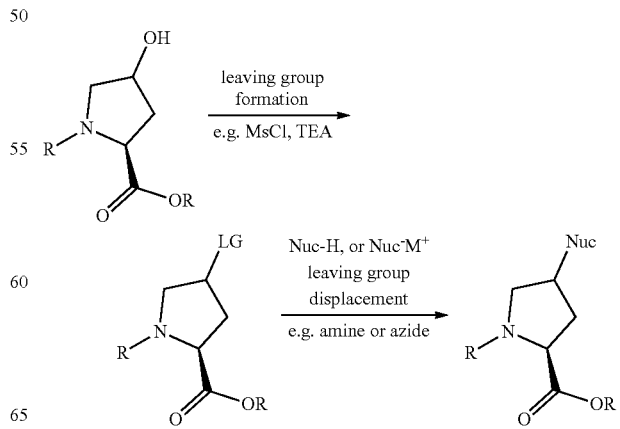

Method E: Synthesis of 4-Triazole Substituted Proline Analogs

An appropriate 4-azido proline analog, prepared as in Method D (where LG is $N_3$), is reacted with a terminal alkyne (such as 2-methyl-3-butyn-2-ol) under a transition metal catalyzed 1,5-cycloaddition reaction (such as RuCp*Cl(PPh$_3$)$_2$, as described in the literature: Boren, B. C., et al. *J. Am. Chem. Soc.* 2008, 130, 8923-8930), resulting in the 1,5-isomer of the 4-triazole substituted proline analogs. Alternatively, applying another transition metal catalytic system (such as CuSO$_4$/L-ascorbic acid, as described in the literature: Rostovtsev, V. V., et al. *Angew. Chem. Int. Ed.* 2002, 41, 2596-2599), the 1,4-cycloaddition product can be facilitated. The proline may be protected at the proline nitrogen (e.g. Boc, Cbz) or may be further functionalized with an α-amino acid or derivative. The proline may be further functionalized with a 1-amino 2-hydroxyacetamide or α-amino boronates.

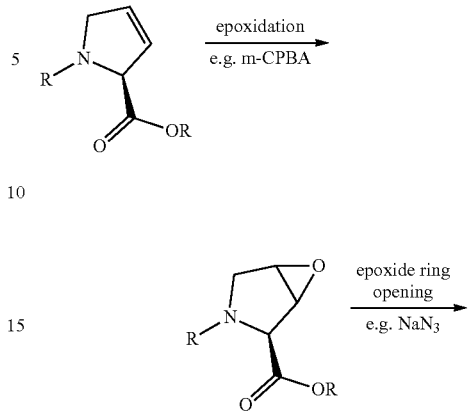

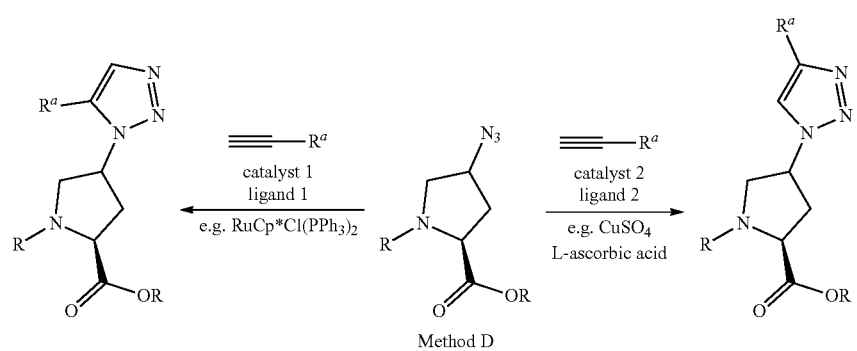

Method D

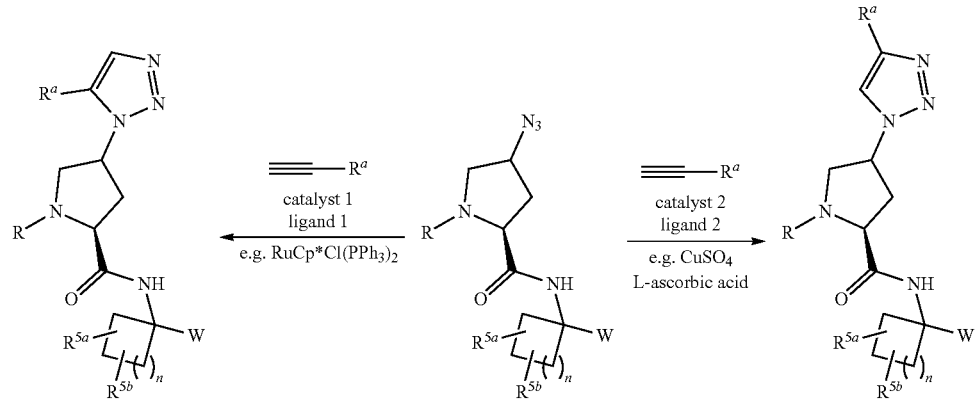

$R^a$ is a substituent for heteroaryl group, as defined under formula (I)

Method F: Synthesis of 3,4-Disubstituted Proline Analogs

The alkene moiety from a 3,4-dehydroproline analog is converted into an epoxide under standard epoxidation conditions (e.g. m-CPBA). The resulting epoxide is then reacted in the presence of a suitable nucleophile (e.g. azide) to afford a 3-hydoxyl 4-substituted proline derivative. The hydroxyl moiety is alkylated using literature alkylation procedures (such as Altmann, E., et al. WO 2012/093101 A1, Jul. 12, 2012). The proline may be protected at the proline nitrogen (e.g. Boc, Cbz) or may be further functionalized with an α-amino acid or derivative. The proline may contain a 2-ester moiety.

-continued

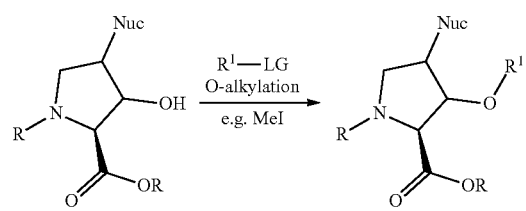

Method G: Synthesis of α-Monosubstituted α-Amino Acid Derivatives

A series of α-monosubstituted α-amino acid derivatives can be obtained via a three-step synthesis from a commercially available primary alcohol. The alcohol is firstly oxidized to an aldehyde under standard alcohol oxidation conditions (e.g. DMP oxidation). The resulting aldehyde can react with commercially available α-phosphoryl-α-amino acid derivatives via a Horner-Wadsworth-Emmons reaction following literature procedures (e.g. St. Jean Jr. D. J., et al. *J. Med. Chem.*, 2014, 57, 309-324). A subsequent olefin hydrogenation of an α,β-unsaturated β-amino ester can be facilitated using conventional heterogeneous catalytic hydrogenation conditions (e.g. cat. Pd/C, H$_2$ balloon), affording α-monosubstituted α-amino acid derivatives.

Method I: Amide Coupling of Proline Analogs with α-Amino Acids

A substituted proline analog (or salt thereof) can be linked with an appropriate carboxylic acid to afford the coupled product under standard amide coupling conditions (e.g. HATU, EtN(iPr)$_2$, CH$_2$Cl$_2$). Typical amide coupling conditions have been described in the literature, including the review article by Valeur, E. et al. *Chem. Soc. Rev.* 2009, 38, 606-631. The α-amino acids may be protected at the nitrogen (e.g. Boc, Cbz) or may be further functionalized with another α-amino acid or derivatives (e.g. R$^1$C(O)—) via another subsequent amide coupling reaction.

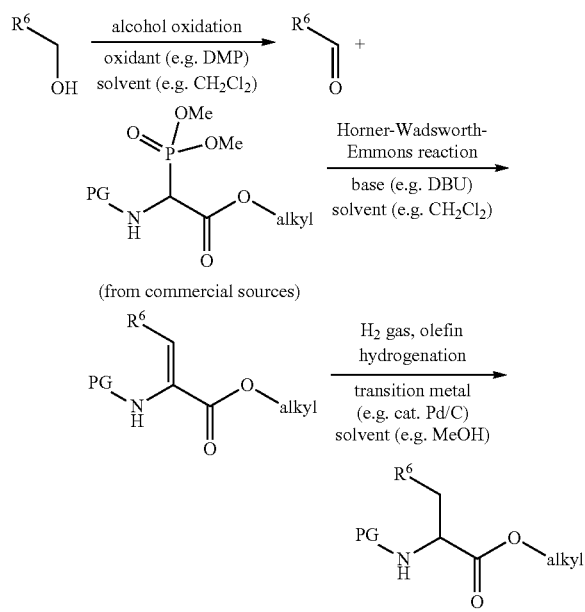

Method H: Synthesis of α,α-Disubstituted α-Amino Acid Derivatives

In certain examples, the α-monosubstituted α-amino acid derivatives can be further functionalized through an α-alkylation process to α,α-disubstituted α-amino acid derivatives. In such cases, an α-monosubstituted α-amino acid derivative is first subjected to α-deprotonation by treatment with a strong base (such as LDA), and the resulting α-nucleophile is reacted with alkyl halides (such as methyl iodide), resulting in an α,α-disubstituted α-amino acid derivative.

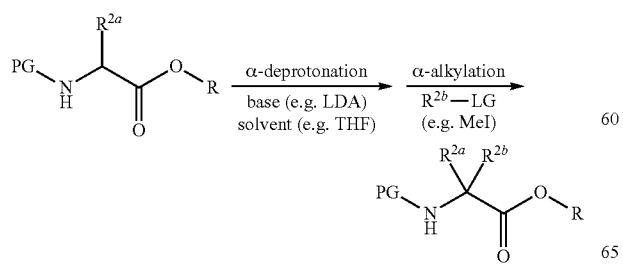

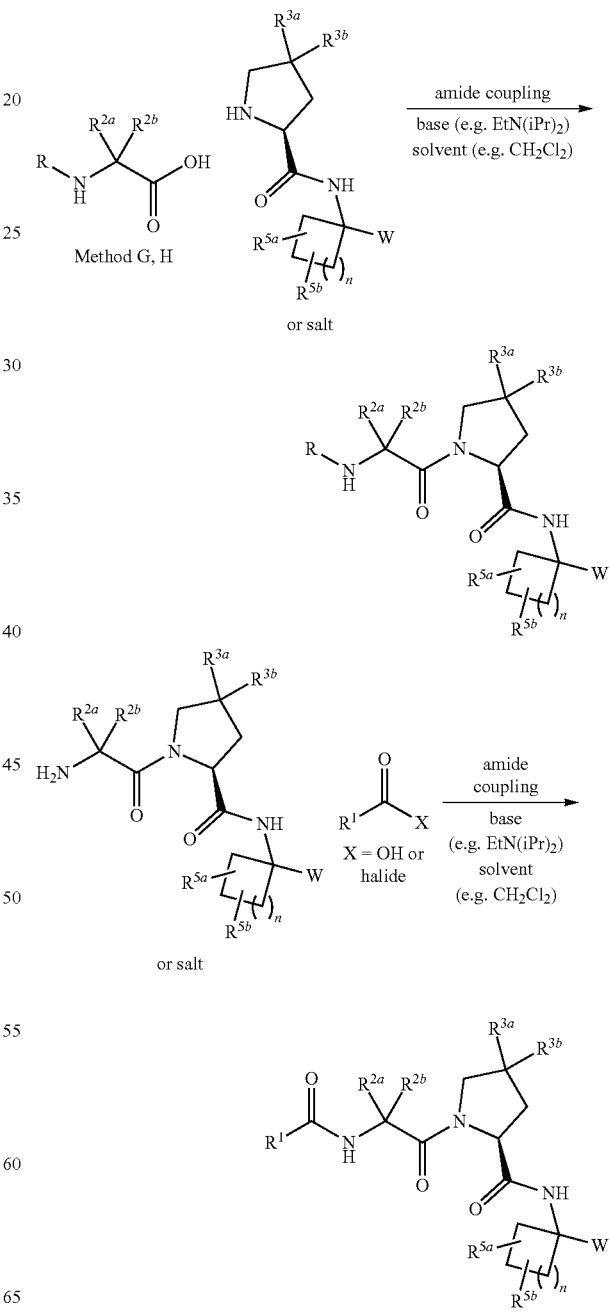

Method J: Oxidation of Hydroxyacetamides to Ketoamides

When W is a hydroxyacetamide moiety, the alcohol can be oxidized to the corresponding ketoamide under standard alcohol oxidation conditions, using oxidizing agents such as DMP or IBX. The proline nitrogen may be protected (e.g. Boc, Cbz) or may be further functionalized with α-amino acids or derivatives.

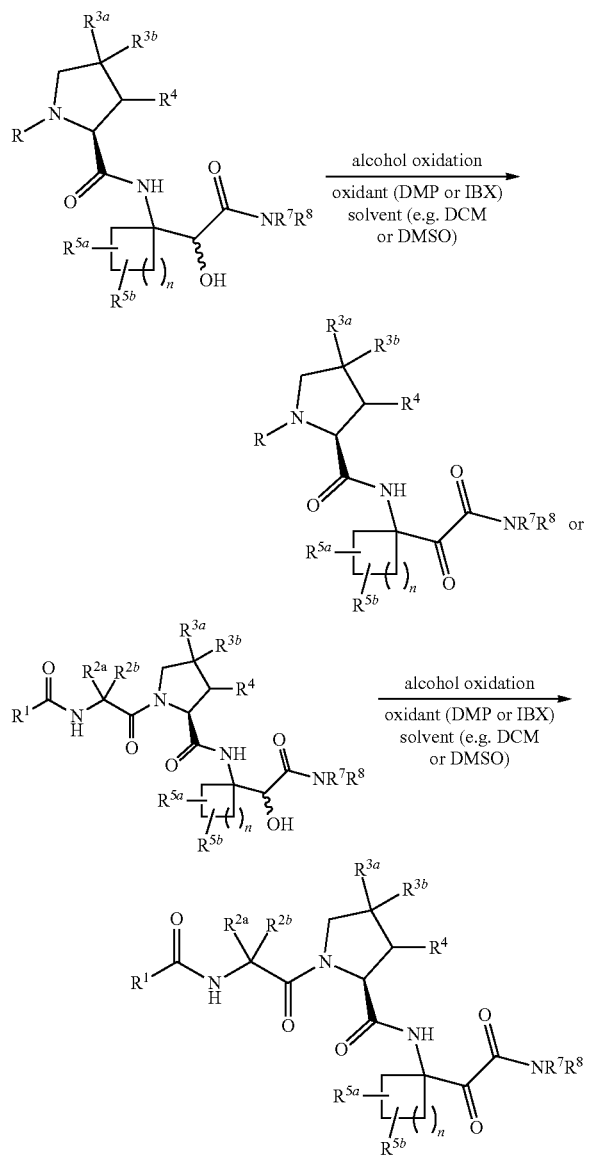

Method K: Deprotection of Boronate Esters to Boronic Acids

Boronate esters can be converted to boronic acids using a number of procedures described in the literature, including those described within Boronic Acids: Preparation and Applications in Organic Synthesis, Medicine and Materials, Second Edition; Dennis Hall, Ed.; 2011 John Wiley & Sons. For example, the boronate ester can be reacted with a sacrificial boronic acid (e.g. phenyl boronic acid or isobutyl boronic acid) in an appropriate solvent (e.g. methanol, ethanol, hexanes or octane) with an acid catalyst (e.g. hydrochloric acid or acetic acid).

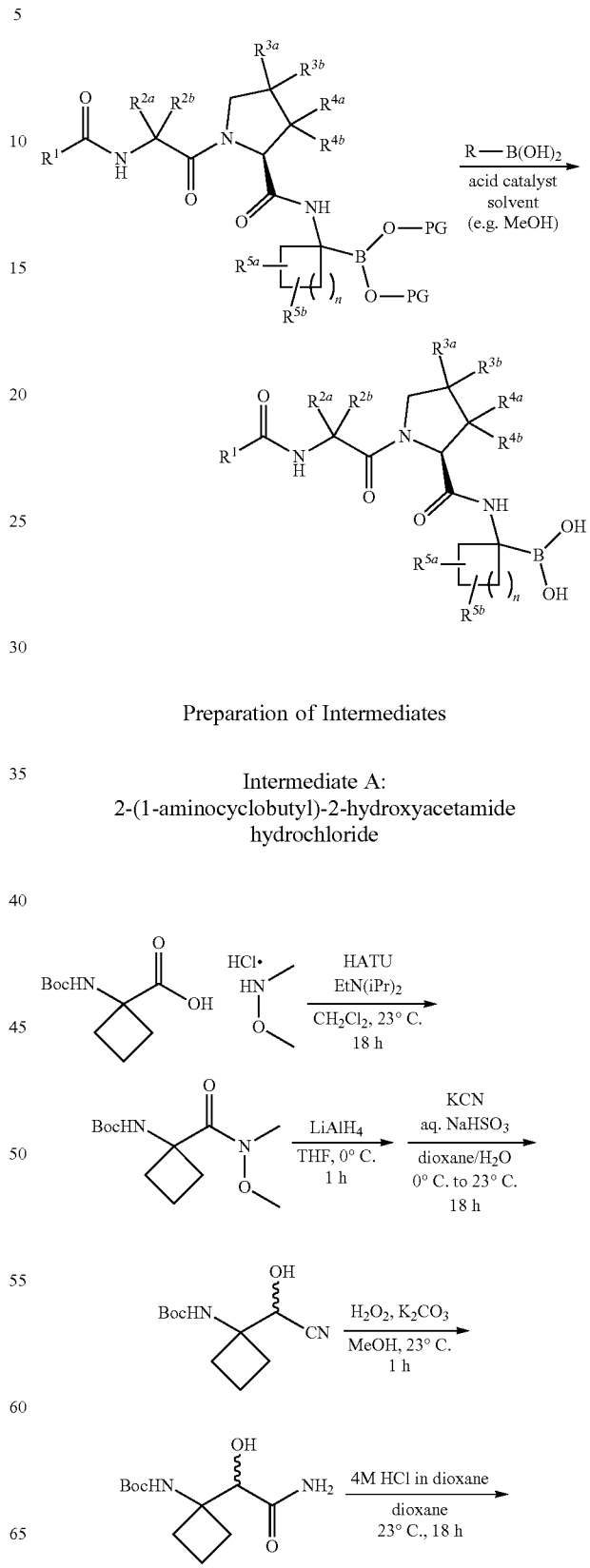

Preparation of Intermediates

Intermediate A:
2-(1-aminocyclobutyl)-2-hydroxyacetamide hydrochloride

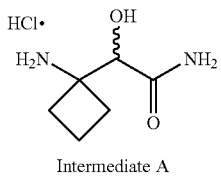

Intermediate A

Step 1: Preparation of tert-butyl (1-(methoxy(methyl)carbamoyl)cyclobutyl)carbamate Into a 100 mL round-bottom flask equipped with a magnetic stir bar and under nitrogen was added the commercially available 1-((tert-butoxycarbonyl)amino)cyclobutanecarboxylic acid (2.0 g, 9.3 mmol, 1.0 equiv), N,O-dimethylhydroxylamine hydrochloride (996 mg, 10.2 mmol, 1.1 equiv), HATU (4.2 g, 11.2 mmol, 1.2 equiv) and dichloromethane (15 mL). EtN(iPr)$_2$ (3.3 mL, 18.6 mmol, 2.0 equiv) was then added to the reaction mixture. The yellow suspension was stirred at room temperature for 18 h. LCMS analysis revealed conversion to product. The reaction mixture was quenched with sat. aqueous ammonia chloride (50 mL) and extracted with CH$_2$Cl$_2$ (3×50 mL) using a 250 mL separatory funnel. The combined organic extracts were washed with brine (50 mL), dried over MgSO$_4$, filtered and concentrated under reduced pressure. The resulting yellow oil was dried under vacuum and used directly without further purification.

Step 2: Preparation of tert-butyl (1-(cyano(hydroxy)methyl)cyclobutyl)carbamate Into a flamed-dried 100 mL round-bottom flask equipped with a magnetic stir bar and under nitrogen was added LiAlH$_4$ (706 mg, 18.6 mmol, 1.9 equiv) and THF (anhydrous, 15 mL). The grey suspension was cooled to −10° C. in an ice/brine bath. The mixture was treated with the dropwise addition of tert-butyl (1-(methoxy(methyl)carbamoyl)cyclobutyl)carbamate (9.9 mmol, 1.0 equiv, dissolved in 15 mL THF) over 20 minutes. The resulting reaction mixture was stirred at −10° C. for 1 hour. The reaction mixture was quenched with the dropwise addition of NaHSO$_4$ in H$_2$O (~40%, 10 mL). The suspension was warmed up to room temperature and stirred for 1 hour. The mixture was poured into a 125 mL separatory funnel and extracted with Et$_2$O (3×30 mL). The combined organic extracts were washed with 1 M aq. HCl (30 mL), sat. aqueous NaHCO$_3$ (30 mL) and brine (30 mL), then dried over MgSO$_4$, filtered and concentrated under reduced pressure.

Without further purification, the resulting orange-yellow oil was dissolved in 1,4-dioxane (20 mL) under nitrogen in a 100 mL round-bottom flask equipped with a magnetic stir bar. The reaction mixture was cooled to 0° C. in an ice bath. To this mixture was added aq. NaHSO$_3$ (40% in H$_2$O, 8.4 mL, 32.2 mmol, 4.0 equiv) over 30 minutes via an additional funnel. KCN (2.1 g, 32.2 mmol, 4.0 equiv) was then added to the reaction mixture. The mixture was stirred at 0° C. for 1 hour and then allowed to warm to room temperature overnight. The reaction mixture was quenched with sat. aq. NaHCO$_3$ (20 mL) and poured into a 125 mL separatory funnel containing water (25 mL) and extracted with EtOAc (3×30 mL). The combined organic extracts were washed with brine (25 mL), then dried over MgSO$_4$, filtered and concentrated under reduced pressure. The residue was purified by column chromatography on the ISCO Rf (40 g silica gel column+20 g pre-cartridge) eluting with 100:0 to 60:40 hexanes:EtOAc as a gradient over 30 min. The title product was obtained as a white solid.

Step 3: Preparation of tert-butyl (1-(2-amino-1-hydroxy-2-oxoethyl)cyclobutyl)carbamate Into a 100 mL round-bottom flask equipped with a magnetic stir bar was added tert-butyl (1-(cyano(hydroxy)methyl)cyclobutyl)carbamate (5.2 mmol, 1.0 equiv) and methanol (20 mL). To this solution was added K$_2$CO$_3$ (786 mg, 5.7 mmol, 1.1 equiv) and the mixture was treated with the dropwise addition of H$_2$O$_2$ (35% in H$_2$O, 1.5 mL, 15.5 mmol, 3.0 equiv). The suspension was stirred at room temperature for 1 hour. TLC analysis at this time revealed conversion to product. The reaction mixture was poured into a 125 mL separatory funnel containing water (50 mL) and extracted with EtOAc (3×20 mL). The combined organic extracts were washed with brine (20 mL), dried over MgSO$_4$, filtered and concentrated under reduced pressure. The residue was purified by column chromatography on the ISCO Rf (50 g silica gel column) eluting with 80:20 to 0:100 hexanes:EtOAc as a gradient over 25 min. The title product was obtained as a clear oil.

Step 4: Preparation of 2-(1-aminocyclobutyl)-2-hydroxyacetamide hydrochloride Into a 50 mL round-bottom flask equipped with a magnetic stir bar under nitrogen was added tert-butyl (1-(2-amino-1-hydroxy-2-oxoethyl)cyclobutyl)carbamate (1.9 mmol, 1.0 equiv) and dioxane (2.4 mL). HCl (4 M in dioxane, 2.4 mL, 9.7 mmol, 5.0 equiv) was added and the yellow solution was stirred at room temperature for 18 h. LCMS analysis revealed the complete conversion of starting material. The reaction mixture was concentrated under reduced pressure and was co-evaporated with MeOH to remove any excess HCl. The resulting solid was dried under vacuum for 18 h. Without further purification, the yellowish crude solid was used directly in subsequent steps.

The following hydroxyacetamide hydrochloride salts, intermediates B, C, D and E, were prepared using the same procedures as described above in the synthesis of intermediate A replacing 1-((tert-butoxycarbonyl)amino)cyclobutanecarboxylic acid with 1-((tert-butoxycarbonyl)amino)cyclopropanecarboxylic acid, 1-((tert-butoxycarbonyl)amino)cyclopentanecarboxylic acid, 1-((tert-butoxycarbonyl)amino)cycloheptanecarboxylic acid and 1-((tert-butoxycarbonyl)amino)-cyclooctanecarboxylic acid, respectively.

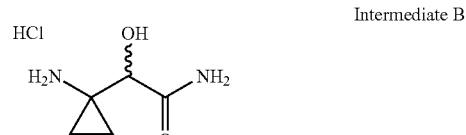

Intermediate B

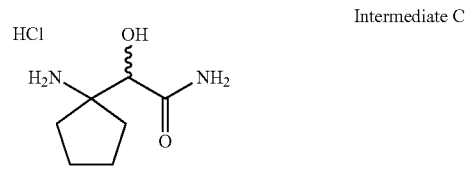

Intermediate C

-continued

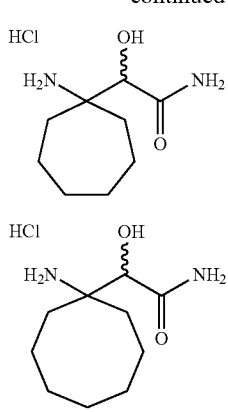

Intermediate D

Intermediate E

Intermediate F: 2-(1-aminocyclohexyl)-2-hydroxyacetamide hydrochloride

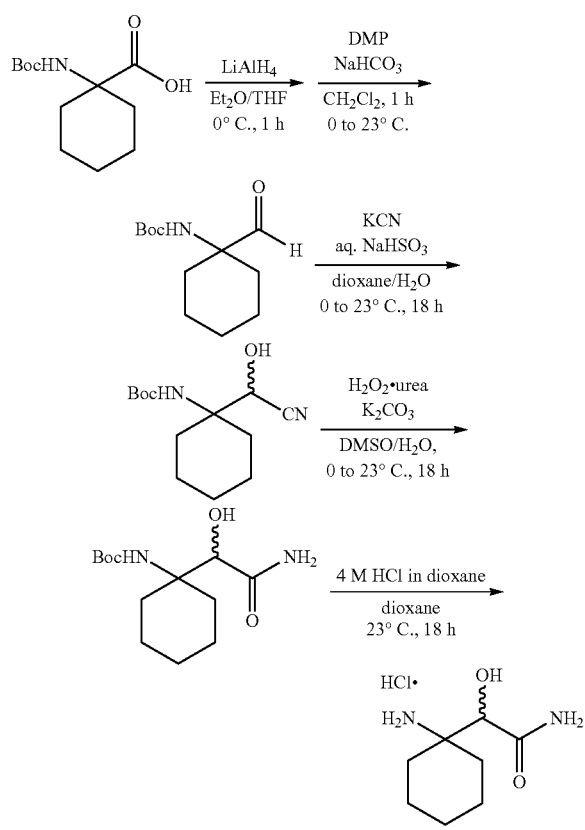

Intermediate F

Step 1: Preparation of tert-butyl (1-formylcyclohexyl)carbamate

Into a flamed-dried 500 mL round-bottom flask equipped with a magnetic stir bar and under nitrogen was added LiAlH$_4$ powder (9.4 g, 246.0 mmol, 4.0 equiv). The solid was diluted with Et$_2$O (anhydrous, 100 mL) and cooled to 0° C. in an ice bath. Into another 250 mL round-bottom flask under nitrogen was added the commercially available 1-((tert-butoxycarbonyl)amino)cyclohexanecarboxylic acid (15.0 g, 61.6 mmol, 1.0 equiv) and THF (anhydrous, 100 mL). The mixture was sonicated to give a solution, which was added dropwise to the LiAlH$_4$/Et$_2$O slurry via an additional funnel over 1 hour. The grey suspension was stirred at 0° C. for 1 hour and then carefully quenched by sequentially dropwise addition of 10 mL H$_2$O, 10 mL of 15% aq. NaOH solution and 25 mL H$_2$O. The resulting grey-white suspension was stirred at 0° C. for 20 minutes and then filtered through a pad of celite on a sintered glass funnel, washing with EtOAc (3×100 mL). The filtrate was dried over MgSO$_4$, filtered and concentrated under reduced pressure. The crude oil was dried under vacuum for 2 hours and used directly without further purification.

Into a 500 mL round-bottom flask equipped with a magnetic stir bar and under nitrogen was added the crude alcohol (61.6 mmol, 1.0 equiv), CH$_2$Cl$_2$ (123 mL, 0.5 M) and NaHCO$_3$ (7.8 g, 92.4 mmol, 1.5 equiv). The suspension was cooled to 0° C. in an ice bath and DMP (31.3 g, 73.9 mmol, 1.2 equiv) was added portionwise over 20 min. The resultant grey-brown reaction mixture was stirred at 0° C. for 40 min. TLC analysis revealed complete conversion of starting material. The reaction mixture was quenched with dropwise addition of 10% aq. sodium thiosulfate solution (50 mL) and poured into a 250 mL separatory funnel containing water (100 mL). The mixture was extracted with CH$_2$Cl$_2$ (3×75 mL). The combined organic extracts were washed with brine (100 mL), dried over MgSO$_4$, filtered and concentrated under reduced pressure. The residue was purified by column chromatography on the ISCO Rf (100 g silica gel column) eluting with 100:0 to 60:40 hexanes:EtOAc as a gradient over 30 min. The title product was obtained as a yellow oil.

Step 2: Preparation of tert-butyl (1-(cyano(hydroxy)methyl)cyclohexyl)carbamate Into a 250 mL round-bottom flask equipped with a magnetic stir bar and under nitrogen was added tert-butyl (1-formylcyclohexyl)carbamate (24.5 mmol, 1.0 equiv) and dioxane (60 mL). The reaction mixture was cooled to 0° C. in an ice bath. To this mixture was added aq. NaHSO$_3$ (40% in H$_2$O, 12.6 mL, 49.0 mmol, 2.0 equiv) over 30 minutes via an additional funnel. KCN (3.2 g, 49.0 mmol, 2.0 equiv) was added last. The mixture was stirred at 0° C. for 1 hour then allowed to warm to room temperature overnight. The reaction mixture was diluted with water (100 mL) and poured into a 250 mL separatory funnel containing water (50 mL) and extracted with EtOAc (3×50 mL). The combined organic extracts were washed with brine (50 mL), then dried over MgSO$_4$, filtered and concentrated under reduced pressure. The residue was purified by column chromatography on the ISCO Rf (100 g SNAP cartridge) eluting with 100:0 to 60:40 hexanes:EtOAc as a gradient over 30 min. The title product was obtained as a white solid.

Step 3: Preparation of tert-butyl (1-(2-amino-1-hydroxy-2-oxoethyl)cyclohexyl)carbamate Into a 100 mL round-bottom flask equipped with a magnetic stir bar was added tert-butyl (1-(cyano(hydroxy)methyl)cyclohexyl)carbamate (9.56 mmol, 1.0 equiv), DMSO (30 mL) and water (10 mL). The reaction mixture was cooled to 0° C. in an ice bath. To this solution was added K$_2$CO$_3$ (660 mg, 4.78 mmol, 0.5 equiv) followed by H$_2$O$_2$·urea (4.5 g, 47.8 mmol, 5.0 equiv). The suspension was stirred at 0° C. for 30 min, then slowly warmed up to room temperature overnight in an ice bath. TLC analysis at this time revealed conversion to product. The reaction mixture was cooled to 0° C. in an ice bath, 10% aq. sodium thiosulfate solution (75 mL) was added and the reaction mixture was stirred for 30 min. The mixture was poured into a 250 mL separatory funnel and extracted with EtOAc (3×100 mL). The combined organic extracts were washed with brine (100 mL), dried over MgSO₄, filtered and concentrated under reduced pressure. The residue was purified by column chromatography on the ISCO Rf (40 g silica gel column) eluting with 80:20 to 0:100 hexanes:EtOAc as a gradient over 30 min. The title product was obtained as a yellow oil.

Step 4: Preparation of 2-(1-aminocyclohexyl)-2-hydroxyacetamide hydrochloride

Prepared in the same manner as 2-(1-aminocyclobutyl)-2-hydroxyacetamide hydrochloride (step 4, intermediate A) using tert-butyl (1-(2-amino-1-hydroxy-2-oxoethyl)cyclohexyl)carbamate to provide the title product.

Intermediate G: 2-(2-aminospiro[3.3]heptan-2-yl)-2-hydroxyacetamide hydrochloride

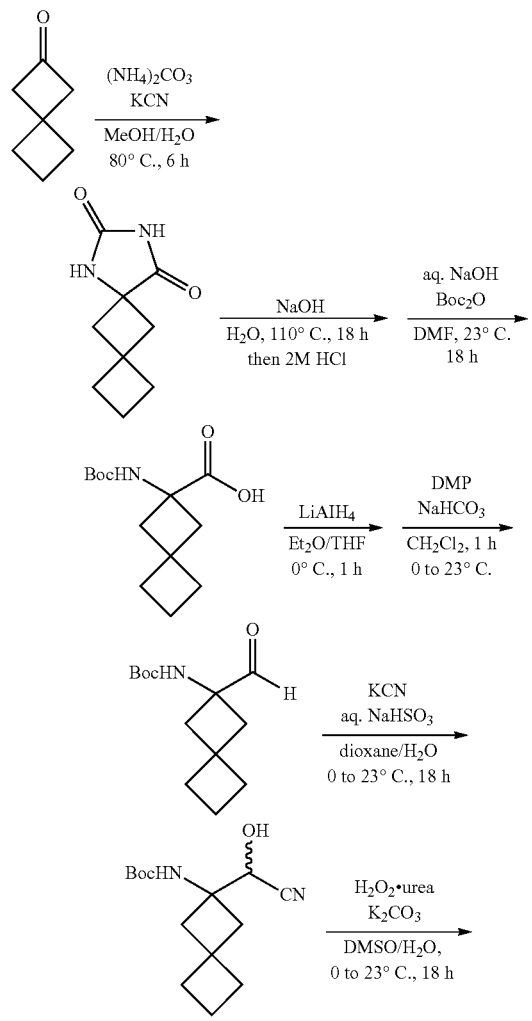

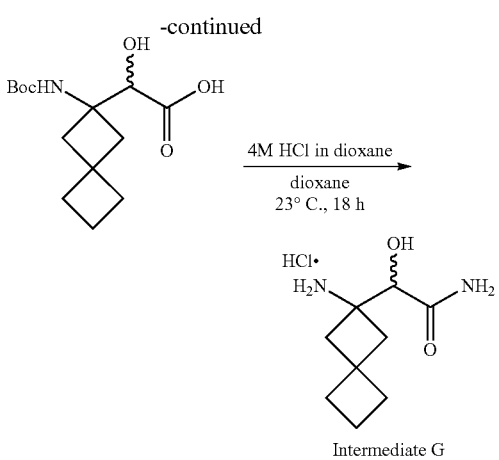

Intermediate G

Step 1: Preparation of 7,9-diazadispiro[3.1.4⁶.1⁴] undecane-8,10-dione

Into a 250 mL round-bottom flask equipped with a magnetic stir bar, reflux condenser and under nitrogen was added spiro[3.3]heptan-2-one (3.3 g, 30 mmol, 1.0 equiv), KCN (5.9 g, 90 mmol, 3.0 equiv), (NH₄)₂CO₃ (8.7 g, 90 mmol, 3.0 equiv), H₂O (45 mL) and methanol (45 mL). The brown solution was refluxed at 80° C. for 6 hours. LCMS analysis revealed the completion of reaction. The reaction mixture was cooled to room temperature and concentrated under reduced pressure to half of its volume. The concentrated solution was cooled in an ice bath for 20 min. The chilled solution was acidified with 2 M HCl (18.8 mL). The resulting precipitate was collected via vacuum filtration and washed with cold water to remove traces of cyanide salt. The solid was dried under vacuum for 18 h to afford the title product as a fine pale yellow solid.

Step 2: Preparation of 2-((tert-butoxycarbonyl)amino)spiro[3.3]heptane-2-carboxylic acid Into a 250 mL round-bottom flask equipped with a magnetic stir bar, reflux condenser and under nitrogen was added 7,9-diazadispiro[3.1.4⁶.1⁴]undecane-8,10-dione (3.0 g, 16.8 mmol, 1.0 equiv), NaOH (2.7 g, 67.3 mmol, 4.0 equiv) and H₂O (67 mL). The suspension was refluxed at 110° C. for 18 hours, yielding a homogeneous dark brown solution. LCMS revealed the completion of hydrolysis. The reaction mixture was cooled to room temperature and chilled in an ice bath. To the chilled solution was added 34 mL of 2 M HCl (67 mmol, 4.0 equiv). Further dropwise addition of 2 M HCl was conducted until the pH of the solution reached 4-6, as monitored by pH paper. The resultant white precipitate was collected through vacuum filtration and washed with water. The solid was further dried under vacuum for 18 h before subjecting to Boc protection.

Into a 250 mL round-bottom flask equipped with a magnetic stir bar was added the above white solid, 1 M NaOH aqueous solution (33.6 mL, 2.0 equiv), Boc₂O (7.2 g, 33.6 mmol, 2.0 equiv) and DMF (5 mL). The reaction mixture was stirred at room temperature for 18 hours. LCMS revealed the completion of reaction. Any excess Boc₂O was quenched by adding imidazole (1.1 g, 16.8 mmol, 1.0 equiv). The mixture was stirred for 10 min, diluted with EtOAc (70 mL) and 1 M HCl (70 mL). The biphasic mixture was poured into a 250 mL separatory funnel and extracted with EtOAc (3×100 mL). The organic extracts were combined, washed with brine (100 mL), dried over MgSO$_4$ and concentrated under reduced pressure to yield a white solid, which was further dried under vacuum for 18 h to afford the title product.

Steps 3-6: Preparation of 2-(2-aminospiro[3.3]heptan-2-yl)-2-hydroxyacetamide hydrochloride Steps 3-6 was performed in the same manner as in the steps 1-4 for the synthesis of intermediate F starting with 2-((tert-butoxycarbonyl)amino)spiro[3.3]heptane-2-carboxylic acid.

The following hydroxyacetamide hydrochloride salts, intermediate H and intermediate I, were prepared using the same procedure as described above in the synthesis of intermediate G, starting with 4,4-dimethylcyclohexanone and spiro[2.5]octan-6-one, respectively.

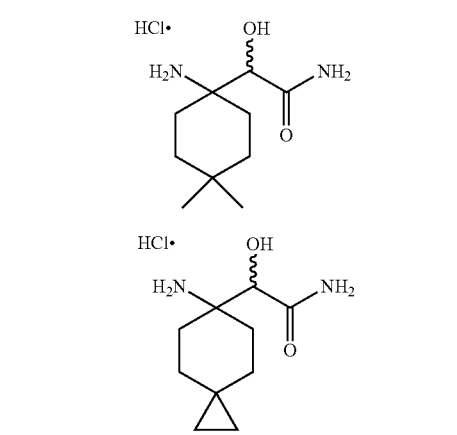

Intermediate H

Intermediate I

Intermediate J: methyl 2-(1-aminocyclohexyl)-2-hydroxyacetate hydrochloride

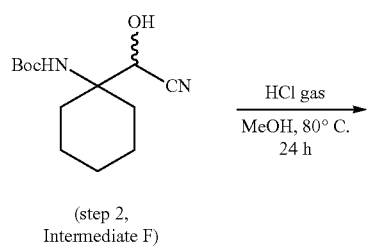

(step 2, Intermediate F)

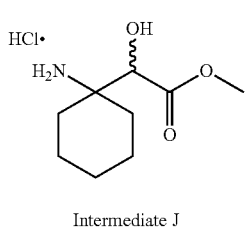

Intermediate J

Into a 200 mL round-bottom flask equipped with a magnetic stir bar, reflux condenser and under nitrogen was added tert-butyl (1-(cyano(hydroxy)methyl)cyclohexyl)carbamate (2.5 g, 9.9 mmol, 1.0 equiv) and methanol (25 mL). The solution was treated with HCl (gas) until saturated (10 min). The resulting mixture was refluxed at 80° C. for 1 hour and additional HCl (gas) was added (1 min). After refluxing at 80° C. for 2 hours, HCl gas was charged again for 1 min. The reaction mixture was refluxed at 80° C. for 18 h. LCMS revealed product and several impurities but no remaining starting material. The reaction mixture was further treated with HCl (gas, 1 min) and refluxed for another 6 hours. The mixture was cooled and concentrated under reduced pressure to give a yellowish oil, which was further dried under vacuum for 18 h to afford the title product.

Intermediate K: 1-(4,4,5,5-tetramethyl-1,3,2-dioxaborolan-2-yl)cyclohexan-1-amine hydrochloride

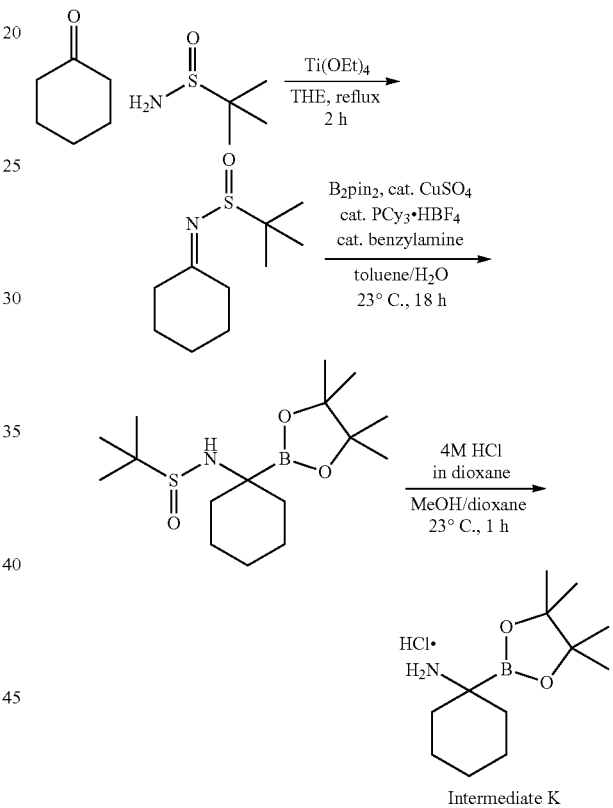

Intermediate K

Step 1: Preparation of N-cyclohexylidene-2-methylpropane-2-sulfinamide

Into a 100 mL round-bottom flask equipped with a magnetic stir bar and under nitrogen was added cyclohexanone (2.0 g, 18.4 mmol, 1.0 equiv), 2-methyl-2-propanesulfinamide (2.3 g, 18.4 mmol, 1.0 equiv), Ti(OEt)$_4$ (8.1 mL, 37.0 mmol, 2.0 equiv) and THF (anhydrous, 25 mL). The mixture was refluxed for 2 hours. TLC analysis revealed completion of reaction. The mixture was cooled to room temperature and poured into 10 mL of sat. aq. NaHCO$_3$ and filtered through a pad of celite on a sintered plastic funnel and washed with CH$_2$Cl$_2$. The combined organic extracts were concentrated under reduced pressure. The residue was purified by column chromatography through silica gel (8 cm×4 cm), eluting with 50:50 hexanes:EtOAc. The title product was obtained as a light yellow oil.

Step 2: Preparation of 2-methyl-N-(1-(4,4,5,5-tetramethyl-1,3,2-dioxaborolan-2-yl)cyclohexyl) propane-2-sulfinamide Into a 4 mL vial equipped with a magnetic stir bar and under nitrogen was added tricyclohexylphosphine tetrafluoroborate ($PCy_3 \cdot HBF_4$) (11 mg, 0.03 mmol, 0.02 equiv), toluene (300 µL), and an aq. solution of $CuSO_4$ (100 mM, 300 µL, 0.03 mmol, 0.02 equiv). The blue suspension was treated with benzylamine and the reaction mixture was stirred at room temperature for 10 min. The mixture was treated with N-cyclohexylidene-2-methylpropane-2-sulfinamide (300 mg, 1.49 mmol, 1.0 equiv) as a solution in 1.2 mL toluene and bis(pinacolate)diboron (762 mg, 3.0 mmol, 1.0 equiv). The resulting light brown solution was stirred at room temperature for 23 hours. LCMS analysis revealed product formation. The reaction mixture was filtered through a plug of Fluorosil (5 cm×3 cm diameter), eluting with EtOAc (30 mL). The yellow filtrate was concentrated under reduced pressure. The residue was purified by column chromatography through Fluorosil (12 cm×4 cm), eluting with 75:25 hexanes:EtOAc. The title product was obtained as a yellow oily solid.

Step 3: Preparation of 1-(4,4,5,5-tetramethyl-1,3,2-dioxaborolan-2-yl)cyclohexan-1-amine hydrochloride Into a 100 mL round-bottom flask equipped with a magnetic stir bar and under nitrogen was added 2-methyl-N-(1-(4,4,5,5-tetramethyl-1,3,2-dioxaborolan-2-yl)cyclohexyl) propane-2-sulfinamide, methanol (1 mL) and dioxane (3 mL). The solution was treated with 4 M HCl in dioxane (900 µL, 3.7 mmol, 2.0 equiv) and the reaction mixture was stirred at room temperature for 1 hour. LCMS analysis revealed complete conversion of starting material. The reaction mixture was concentrated under reduced pressure, resuspended in $Et_2O$ (3 mL) and stirred for 20 min, resulting in a beige suspension. After 30 min, the suspension was filtered through Nylon 0.45 µm filter paper and the beige solid was dried under vacuum for 18 h to afford the title product.

Intermediate L: (2S,4S)-1-((R)-2-(2-naphthamido)-3-cyclohexylpropanoyl)-4-azidopyrrolidine-2-carboxylic acid

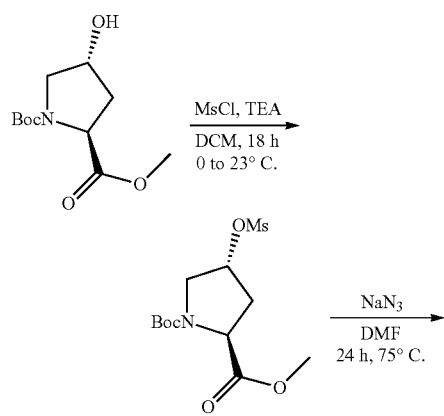

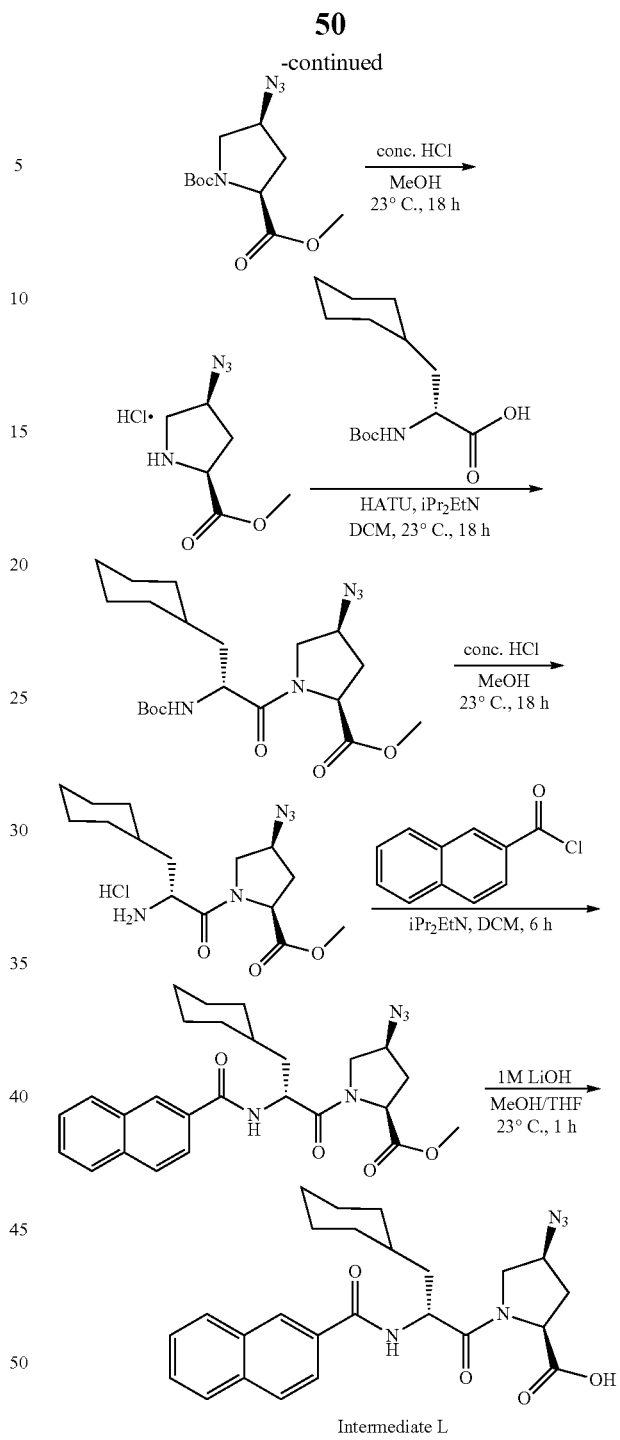

Intermediate L

Step 1: Preparation of 1-(tert-butyl) 2-methyl (2S, 4R)-4-((methylsulfonyl)oxy) pyrrolidine-1,2-dicarboxylate To a solution of 1-(tert-butyl) 2-methyl (2S,4R)-4-hydroxypyrrolidine-1,2-dicarboxylate (13.2 g, 53.8 mmol, 1.0 equiv) in DCM (110 mL) cooled to 0° C. in an ice bath was added TEA (17 mL, 236.8 mmol, 4.4 equiv) and MsCl (9.2 mL, 118.4 mmol, 2.2 equiv). The reaction mixture was allowed to warm to 23° C. and stirred for 18 hours. After this time, the reaction mixture was diluted with DCM and washed with sat. aq. $NaHCO_3$, water and then brine. The organic layer was dried over MgSO4, filtered and concentrated under reduced pressure to provide the title compound.

Step 2: Preparation 1-(tert-butyl) 2-methyl (2S,4S)-4-azidopyrrolidine-1,2-dicarboxylate A suspension of 1-(tert-butyl) 2-methyl (2S,4R)-4-((methylsulfonyl)oxy) pyrrolidine-1,2-dicarboxylate (20.0 g, 53.8 mmol, 1.0 equiv) and NaN$_3$ (7.0 g, 107.6 mmol, 2.0 equiv) in DMF (110 mL) was stirred at 75° C. After 24 hours, the mixture was allowed to cool to 23° C. and was diluted with water and extracted with EtOAc (3×). The combined organic extracts were washed with brine, dried over MgSO$_4$, filtered and concentrated under reduced pressure. This residue was purified by column chromatography using a RediSep cartridge (80 g) eluting with a 0:100 to 20:80 EtOAc:hexanes gradient. The desired fractions were concentrated under reduced pressure to provide the title compound.

Step 3: Preparation of methyl (2S,4S)-4-azidopyrrolidine-2-carboxylate hydrochloride To a solution of 1-(tert-butyl) 2-methyl (2S,4S)-4-azidopyrrolidine-1,2-dicarboxylate (14.5 g, 53.8 mmol, 1.0 equiv) in MeOH (135 mL) was added 36% aq. HCl (19 mL, 188.3 mmol, 3.5 equiv) and the reaction mixture was stirred at 23° C. After 18 hours, the reaction mixture was concentrated under reduced pressure and the residue was azeotroped with MeOH (3×) to provide the title compound.

Step 4: Preparation of methyl (2S,4S)-4-azido-1-((R)-2-((tert-butoxycarbonyl)amino)-3-cyclohexylpropanoyl)pyrrolidine-2-carboxylate A suspension of (R)-2-((tert-butoxycarbonyl)amino)-3-cyclohexylpropanoic acid (12.8 g, 47 mmol, 1.0 equiv) and HATU (17.9 g, 47 mmol, 1.0 equiv) in DCM (110 mL) was stirred for 10 minutes and then methyl (2S,4S)-4-azidopyrrolidine-2-carboxylate hydrochloride (9.7 g, 47 mmol, 1.0 equiv) and iPr$_2$EtN (20.5 mL, 118 mmol, 2.5 equiv) were added and the reaction mixture was stirred at 23° C. After 18 hours, the mixture was partitioned with 1 M HCl (200 mL). The aqueous layer was extracted with DCM (3×). The combined organic extracts were washed with brine, dried over MgSO$_4$, filtered and concentrated under reduced pressure. This residue was purified by column chromatography using a RediSep cartridge (120 g) eluting with a 0:100 to 50:50 EtOAc:hexanes gradient. The fractions were monitored by TLC (EtOAc/hexanes (3/7), visualized by ninhydrin staining). The desired fractions were concentrated under reduced pressure to provide the title compound.

Step 5: Preparation of methyl (2S,4S)-1-((R)-2-amino-3-cyclohexylpropanoyl)-4-azidopyrrolidine-2-carboxylate hydrochloride Prepared in a similar manner as methyl (2S,4S)-4-azidopyrrolidine-2-carboxylate hydrochloride (step 3, intermediate L) using methyl (2S,4S)-4-azido-1-((R)-2-((tert-butoxycarbonyl)amino)-3-cyclohexylpropanoyl)pyrrolidine-2-carboxylate to provide the title compound.

Step 6: Preparation of methyl (2S,4S)-1-((R)-2-(2-naphthamido)-3-cyclohexylpropanoyl)-4-azidopyrrolidine-2-carboxylate To a suspension of methyl (2S,4S)-1-((R)-2-amino-3-cyclohexylpropanoyl)-4-azidopyrrolidine-2-carboxylate hydrochloride (10.4 g, 29 mmol, 1.0 equiv) and 2-naphthoyl chloride (6.1 g, 31.9 mmol, 1.1 equiv) in DCM (150 mL) was added iPr$_2$EtN (12.6 mL, 72.5 mmol, 2.5 equiv) and the reaction mixture was stirred at 23° C. After 6 hours, the mixture was partitioned between 1 M HCl (100 mL) and DCM (3×). The combined organic extracts were washed with water, dried over MgSO$_4$, filtered and concentrated under reduced pressure. This residue was purified by column chromatography using a RediSep cartridge (330 g) eluting with a 0:100 to 50:50 EtOAc:hexanes gradient. The desired fractions were concentrated under reduced pressure to provide the title compound.

Step 7: Preparation of (2S,4S)-1-((R)-2-(2-naphthamido)-3-cyclohexylpropanoyl)-4-azido pyrrolidine-2-carboxylic acid To a solution of methyl (2S,4S)-1-((R)-2-(2-naphthamido)-3-cyclohexylpropanoyl)-4-azido pyrrolidine-2-carboxylate (2.9 g, 5.3 mmol, 1.0 equiv) in MeOH (25 mL) and THF (25 mL) was added 1 M aq. LiOH (26 mL, 26 mmol, 5.0 equiv) and the mixture was stirred at 23° C. After 1 hour, the reaction mixture was concentrated under reduced pressure and the resulting residue was dissolved in THF (30 mL) and 1 M aq. HCl was added until the pH of the solution reached 1. This mixture was further diluted with water and extracted with EtOAc (3×20 mL). The combined organic extracts were dried over MgSO$_4$, filtered and concentrated under reduced pressure to provide the title compound.

Intermediate M: (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylic acid

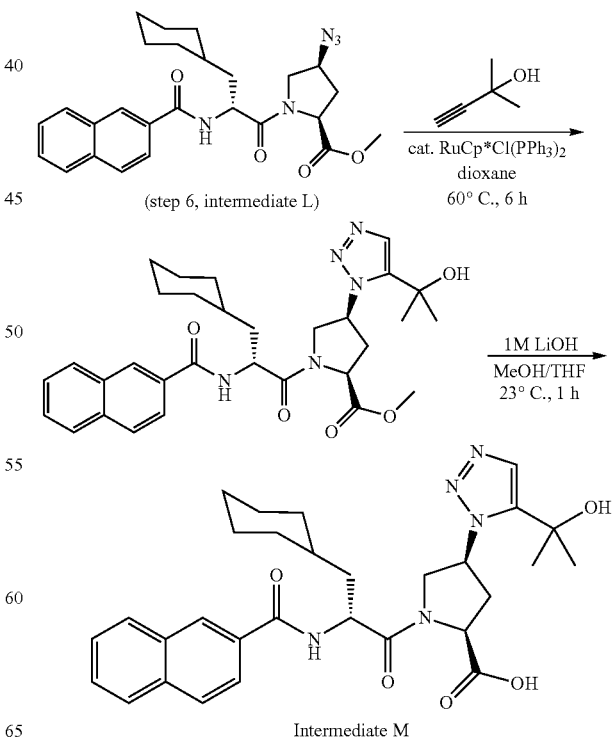

Intermediate M

Step 1: Preparation of methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate To a 40 mL scintillation vial was added methyl (2S,4S)-1-((R)-2-(2-naphthamido)-3-cyclohexylpropanoyl)-4-azidopyrrolidine-2-carboxylate (2.5 g, 5.2 mmol, 1.0 equiv), 2-methylbut-3-yn-2-ol (1.7 g, 20.8 mmol, 4.0 equiv), pentamethylcyclopentadienylbis(triphenylphosphine)ruthenium (II) chloride (199 mg, 0.26 mmol, 0.05 equiv) and dioxane (26 mL). The dark brown solution was purged with a stream of nitrogen for 30 min. The bubbler was removed and this mixture was stirred at 60° C. under nitrogen for 6 h. After this time, the mixture was purified by column chromatography using a RediSep cartridge (40 g) eluting with 100% EtOAc. The desired fractions were concentrated under reduced pressure to provide the title compound.

Step 2: Preparation of (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) to provide the title compound.

Intermediate N:
(R)-2-(2-naphthamido)-3-cyclohexylpropanoic acid

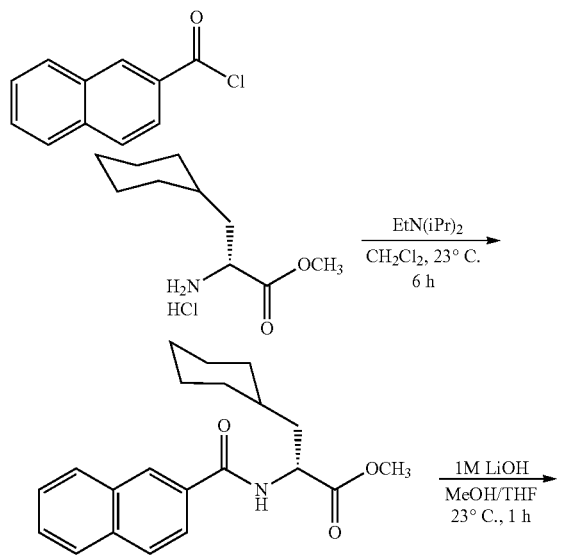

Intermediate N

Step 1: Preparation of methyl (R)-2-(2-naphthamido)-3-cyclohexylpropanoate

Prepared in a similar manner as methyl (2S,4S)-1-((R)-2-(2-naphthamido)-3-cyclohexylpropanoyl)-4-azidopyrrolidine-2-carboxylate (step 6, intermediate L) using (R)-methyl 2-amino-3-cyclohexylpropanoate hydrochloride and 2-naphthoyl chloride to provide the title compound.

Step 2: Preparation of (R)-2-(2-naphthamido)-3-cyclohexylpropanoic acid

Prepared in a similar manner as (2S,4S)-1-((R)-2-(2-naphthamido)-3-cyclohexylpropanoyl)-4-azido pyrrolidine-2-carboxylic acid (step 7, intermediate L) using (R)-methyl 2-(2-naphthamido)-3-cyclohexylpropanoate to provide the title compound.

Intermediate O: Benzyl (2S,3R,4R)-4-(5-(2-hydroxypropan-2-yl)-1H-1,2,3-triazol-1-yl)-3-methoxypyrrolidine-2-carboxylate hydrochloride

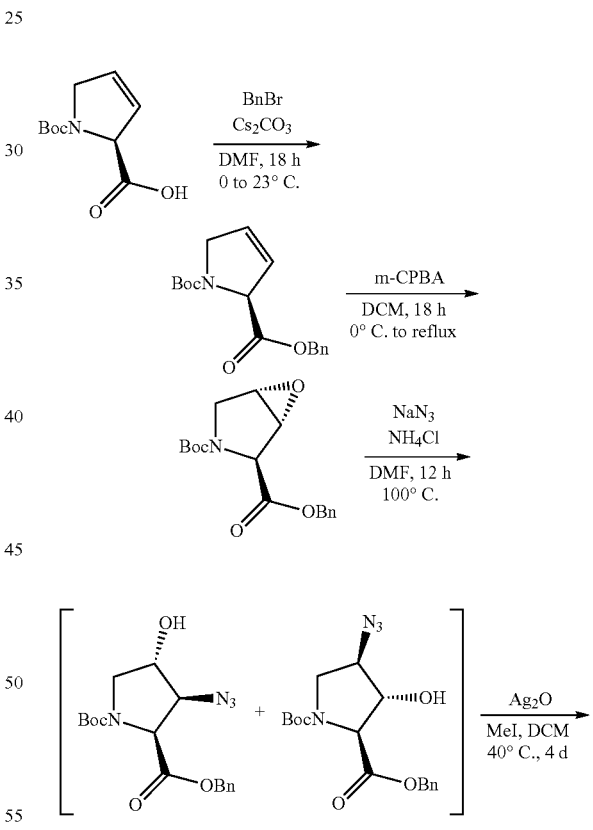

mixture of regiomers

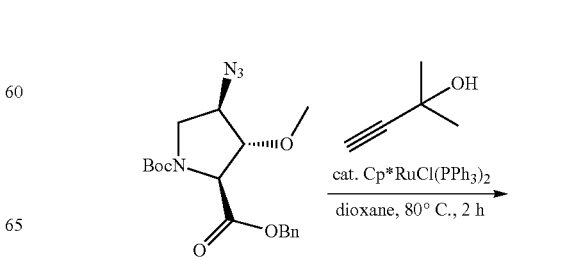

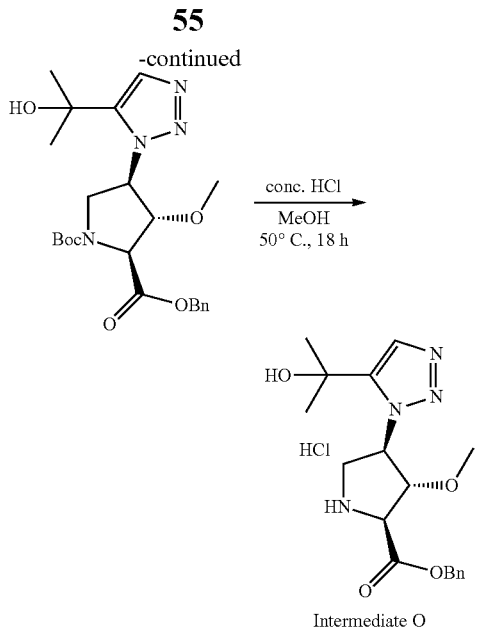

Intermediate O

Step 1: Preparation of (S)-2-benzyl 1-tert-butyl 1H-pyrrole-1,2(2H,5H)-dicarboxylate Into a 250 mL round bottom flask equipped with a magnetic stir bar and under nitrogen was added Boc-3,4-dihydro-Pro-OH (5.0 g, 23.4 mmol, 1.0 equiv), $Cs_2CO_3$ (8.4 g, 25.7 mmol, 1.1 equiv) and DMF (75 mL). The suspension was cooled to 0° C. and benzyl bromide (3.3 mL, 28.1 mmol, 1.2 equiv) was added. The grey-tan suspension was stirred at 0° C. for 1 hour, then allowed to warm to room temperature overnight. LCMS revealed product formation. The reaction mixture was quenched with water (200 mL) and poured into a 500 mL separatory funnel containing water (50 mL) and extracted with EtOAc (3×50 mL). The combined organic extracts were washed with brine, dried over $MgSO_4$, filtered and concentrated under reduced pressure. The residue was purified by column chromatography on the ISCO Rf (100 g SNAP cartridge) eluting with 100:0 to 60:40 hexanes:EtOAc as a gradient over 30 min. The resulting yellow oil was further dried under vacuum to yield the title product.

Step 2: Preparation of 2-benzyl 3-(tert-butyl) (1R,2S,5S)-6-oxa-3-azabicyclo[3.1.0]hexane-2,3-dicarboxylate Into a 250 mL round bottom flask equipped with magnetic stir bar, reflux condenser and under nitrogen was added (S)-2-benzyl 1-tert-butyl 1H-pyrrole-1,2(2H,5H)-dicarboxylate (4.5 g, 14.9 mmol, 1.0 equiv) and DCM (35 mL). The solution was cooled to 0° C. in an ice bath and treated with m-CPBA (6.7 g, 29.7 mmol, 2.0 equiv). After warming to room temperature, the reaction mixture was refluxed for 18 h. LCMS analysis revealed complete conversion of starting material. The reaction mixture was cooled to room temperature and quenched with 10% aq. $Na_2S_2O_3$ (100 mL). The mixture was stirred at room temperature for 1 hour and poured into a 250 mL separatory funnel and extracted with DCM (3×75 mL). The combined organic extracts were washed with sat. aq. $NaHCO_3$ (2×75 mL), brine (75 mL), dried over $MgSO_4$, filtered and concentrated under reduced pressure. The residue was purified by column chromatography on the ISCO Rf (80 g silica gel Gold column+20 g pre-cartridge) eluting with 100:0 to 60:40 hexanes:EtOAc as a gradient over 30 min. Both diastereomers were collected and further dried under vacuum. The resulting mixture of two diastereomers was subject to further purification by column chromatography on the ISCO Rf (80 g silica gel Gold column+20 g pre-cartridge) eluting with 100:0 to 60:40 hexanes:EtOAc as a gradient over 30 min. The desired diastereomer (first eluting peak) was isolated as a clear oil.

Step 3: Preparation of 2-benzyl 1-(tert-butyl) (2S,3S,4S)-3-azido-4-hydroxypyrrolidine-1,2-dicarboxylate and 2-benzyl 1-(tert-butyl) (2S,3R,4R)-4-azido-3-hydroxypyrrolidine-1,2-dicarboxylate (mixture of two regioisomers)

Into a 100 mL microwave vial equipped with magnetic stir bar under nitrogen was added 2-benzyl 3-(tert-butyl) (1R,2S,5S)-6-oxa-3-azabicyclo[3.1.0]hexane-2,3-dicarboxylate (1.8 g, 5.6 mmol, 1.0 equiv), sodium azide (1.8 g, 28.2 mmol, 5.0 equiv), $NH_4Cl$ (603 mg, 11.3 mmol, 2.0 equiv) and DMF (15 mL). The vial was sealed, kept under nitrogen and heated to 100° C. in an oil bath for 2 hours. LCMS analysis revealed complete conversion of starting material and formation of two regioisomers. Both LCMS and TLC indicated that the two regioisomers would be difficult to separate. The reaction mixture was cooled to room temperature and poured into a 250 mL separatory funnel containing water (100 mL) and extracted with EtOAc (3×30 mL). The combined organic extracts were washed with brine, dried over $MgSO_4$, filtered and concentrated under reduced pressure. The residue was purified by column chromatography on the ISCO Rf (80 g silica gel column+20 g pre-cartridge) eluting with 80:20 to 20:80 hexanes:EtOAc as a gradient over 30 min. The mixture of two regioisomers were collected, further dried under vacuum to afford a clear oil.

Step 4: Preparation of 2-benzyl 1-(tert-butyl) (2S,3R,4R)-4-azido-3-methoxypyrrolidine-1,2-dicarboxylate Into a 75 mL bomb (high pressure, thick-walled reaction flask) equipped with magnetic stir bar was added the mixture of regioisomers obtained in step 3 (1.6 g, 4.3 mmol, 1.0 equiv), silver oxide (5.0 g, 21.5 mmol, 5.0 equiv) and DCM (10 mL). Iodomethane (1.3 mL, 21.5 mmol, 5.0 equiv) was then added. The black suspension was sealed in the flask, wrapped with aluminum foil and heated in an oil bath at 40° C. for 4 days. LCMS analysis revealed complete conversion of one regioisomer and formation of the desired methylation product, while the other regioisomer remained inactive under above reaction conditions. The reaction mixture was cooled to room temperature and filtered through a pad of celite on a sintered glass funnel, washing with DCM (3×10 mL). The combined organic extracts were concentrated under reduced pressure and dried under vacuum to afford the title product as a clear oil.

Step 5: Preparation of 2-benzyl 1-(tert-butyl) (2S,3R,4R)-4-(5-(2-hydroxypropan-2-yl)-1H-1,2,3-triazol-1-yl)-3-methoxypyrrolidine-1,2-dicarboxylate To a 40 mL scintillation vial was added 2-benzyl 1-(tert-butyl) (2S,3R,4R)-4-azido-3-methoxypyrrolidine-1,2-dicarboxylate (4.3 mmol, 1.0 equiv), 2-methylbut-3-yn-2-ol (855 μL, 8.6 mmol, 2 equiv), pentamethylcyclopentadienylbis (triphenylphosphine)ruthenium(II) chloride (169 mg, 0.22 mmol, 0.05 equiv) and dioxane (15 mL). This mixture was stirred at 80° C. under nitrogen for 2 hours. This reaction mixture was concentrated under reduced pressure and loaded onto an 80 g Gold silica gel column. The residue was purified by column chromatography on the ISCO Rf eluting with 80:20 to 20:80 hexanes:EtOAc as a gradient over 25 min. The desired fractions were concentrated under reduced pressure and further dried under vacuum to afford a brownish oil as the title product.

Step 6: Preparation of benzyl (2S,3R,4R)-4-(5-(2-hydroxypropan-2-yl)-1H-1,2,3-triazol-1-yl)-3-methoxypyrrolidine-2-carboxylate hydrochloride Into a 100 mL round bottom flask equipped with magnetic stir bar and under nitrogen was added 2-benzyl 1-(tert-butyl) (2S,3R,4R)-4-(5-(2-hydroxypropan-2-yl)-1H-1,2,3-triazol-1-yl)-3-methoxy pyrrolidine-1,2-dicarboxylate (1.7 g, 3.7 mmol, 1.0 equiv) and methanol (25 mL). Concentrated aq. HCl (12 M, 2 mL, 24 mmol, 6.5 equiv) was added and the brown solution was heated to 50° C. in an oil bath for 18 h. LCMS revealed conversion of starting material to product. The reaction mixture was cooled to room temperature and concentrated under reduced pressure. The crude mixture was co-evaporated with methanol (2×30 mL) to remove any trace amounts of HCl and water, yielding the title product.

Intermediate P: 2-((tert-butoxycarbonyl)amino)-3-cyclohexyl-2-methylpropanoic acid

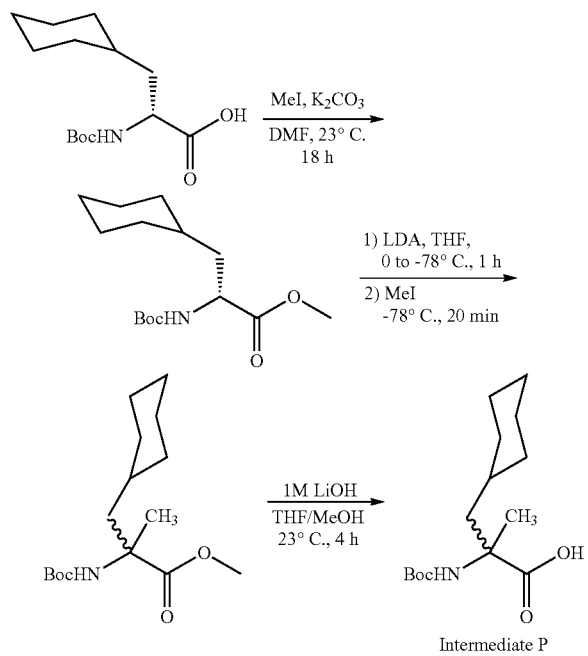

Intermediate P

Step 1: Preparation of methyl (R)-2-((tert-butoxycarbonyl)amino)-3-cyclohexylpropanoate Into a 100 mL round bottom flask equipped with a magnetic stir bar and under nitrogen was added Boc-3-cyclohexyl-D-alanine (3.0 g, 11.1 mmol, 1.0 equiv), $K_2CO_3$ (8.4 g, 11.1 mmol, 1.0 equiv) and DMF (20 mL). The solution was treated with methyl iodide (753 μL, 12.1 mmol, 1.1 equiv) and the reaction mixture was stirred at room temperature for 18 h. To the reaction mixture was added EtOAc (100 mL) and the mixture was washed with water (3×100 mL). The organic layer was dried over $MgSO_4$, filtered and concentrated under reduced pressure to give the title compound as an oil.

Step 2: Preparation of methyl 2-((tert-butoxycarbonyl)amino)-3-cyclohexyl-2-methylpropanoate Into a 100 mL flame-dried round bottom flask equipped with magnetic stir bar under nitrogen was added diisopropylamine (3.7 mL, 26.4 mmol, 2.4 equiv) and anhydrous THF (25 mL). The solution was cooled to −78° C. in an acetone/dry ice bath. n-Butyllithium (2.5 M in hexanes, 10.6 mL, 2.4 equiv) was added dropwise and the mixture was stirred at −78° C. for 30 min. Into another 100 mL flame-dried round bottom flask under nitrogen was added (R)-2-((tert-butoxycarbonyl)amino)-3-cyclohexylpropanoate (11.0 mmol, 1.0 equiv) and anhydrous THF (25 mL). The mixture was added to the lithium diisopropylamide solution dropwise. The reaction mixture was stirred at −78° C. for 30 min, followed by the addition of methyl iodide (691 μL, 11.0 mmol, 1.1 equiv). The mixture was allowed to warm up to room temperature and stirred for 20 min. LCMS analysis revealed the formation of product. The reaction mixture was quenched with sat. aq. $NaHCO_3$ (100 mL) and poured into a 250 mL separatory funnel and extracted with DCM (3×100 mL). The combined organic extracts were washed with brine (75 mL), dried over $MgSO_4$, filtered and concentrated under reduced pressure. The residue was purified by column chromatography on the ISCO Rf (40 g silica gel Gold column+20 g pre-cartridge) eluting with 100:0 to 90:10 DCM:MeOH as a gradient over 17 min. The desired peaks were concentrated under reduced pressure and dried under vacuum to afford the title compound.

Step 3: Preparation of 2-((tert-butoxycarbonyl)amino)-3-cyclohexyl-2-methylpropanoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-((tert-butoxycarbonyl)amino)-3-cyclohexyl-2-methylpropanoate to provide the title compound.

Intermediate Q: 2-((tert-butoxycarbonyl)amino)-3-(spiro[3.3]heptan-2-yl)propanoic acid

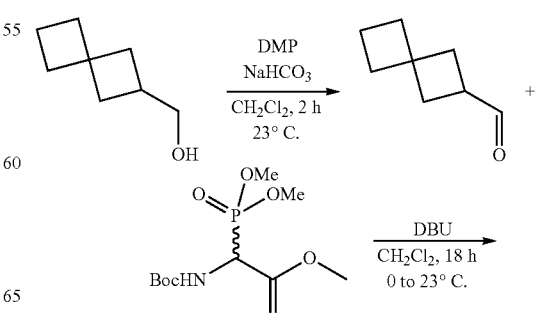

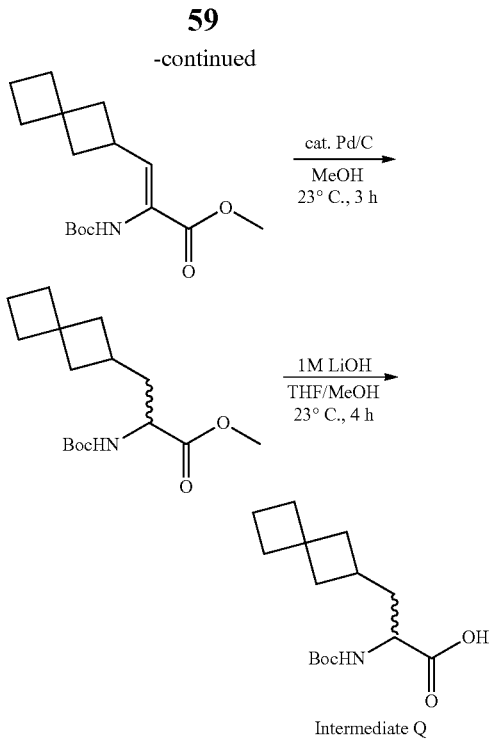

Intermediate Q

Step 1: Preparation of spiro[3.3]heptane-2-carbaldehyde

Into a 50 mL round-bottom flask equipped with a magnetic stir bar and under nitrogen was added spiro[3.3]heptan-2-ylmethanol (150 mg, 1.2 mmol, 1.0 equiv), NaHCO₃ (150 mg, 1.8 mmol, 1.5 equiv) and DCM (3 mL). The suspension was treated with DMP (605 mg, 1.4 mmol, 1.2 equiv) and the mixture was stirred for 2 hours at room temperature. TLC analysis (10:90 EtOAC:hexanes v/v) revealed complete conversion of the starting alcohol. The reaction mixture was quenched with 10 mL of 10% aq. Na₂S₂O₃ and stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (12 g Gold C18 column) eluting with 0:100 to 20:80 MeOH:DCM as a gradient over 20 min. The desired peaks were concentrated under reduced pressure and dried under vacuum to afford the title compound as a clear oil.

Step 2: Preparation of methyl (Z)-2-((tert-butoxycarbonyl)amino)-3-(spiro[3.3]heptan-2-yl) acrylate Into a 100 mL flame-dried round bottom flask equipped with magnetic stir bar under nitrogen was added methyl 2-((tert-butoxycarbonyl)amino)-2-(dimethoxyphosphoryl)acetate (169 mg, 0.57 mmol, 1.0 equiv) and anhydrous DCM (2 mL). The solution was cooled to 0° C. in an ice bath. To this mixture was slowly added DBU (86 µL, 0.57 mmol, 1.0 equiv). The mixture was stirred at 0° C. for 20 min and then treated with a solution of spiro[3.3]heptane-2-carbaldehyde (86 mg, 0.69 mmol, 1.2 equiv) in DCM (2 mL). The reaction mixture was allowed to warm to room temperature slowly overnight. LCMS analysis revealed the formation of product. The reaction mixture was quenched with sat. aq. NH₄Cl (20 mL) and poured into a 125 mL separatory funnel and extracted with DCM (3×15 mL). The combined organic extracts were washed with brine (25 mL), dried over MgSO₄, filtered and concentrated under reduced pressure. The residue was purified by column chromatography on the ISCO Rf (12 g silica gel column+5 g pre-cartridge) eluting with 0:100 to 30:70 EtOAc:hexanes as a gradient over 19 min. The desired peaks were concentrated under reduced pressure and dried under vacuum to afford the title compound.

Step 3: Preparation of methyl 2-((tert-butoxycarbonyl)amino)-3-(spiro[3.3]heptan-2-yl) propanoate Into a 25 mL round bottom flask equipped with a magnetic stir bar and under nitrogen was added methyl (Z)-2-((tert-butoxycarbonyl)amino)-3-(spiro[3.3]heptan-2-yl) acrylate (358 mg, 0.57 mmol, 1.0 equiv) and MeOH (3 mL). The solution was sparged with nitrogen for 30 min. Pd/C (10% wt., 25 mg) was added. The nitrogen source was then replaced with a hydrogen balloon. The reaction mixture was sparged with 1 balloon of hydrogen and the reaction mixture was stirred at room temperature under an atmosphere of hydrogen for 3 h. LCMS analysis revealed completion of reaction. The reaction mixture was filtered through a pad of celite on a plastic sintered funnel, washed with DCM (3×5 mL). The clear filtrate was concentrated under reduced pressure and used directly in the next step without further purification.

Step 4: Preparation of 2-((tert-butoxycarbonyl)amino)-3-(spiro[3.3]heptan-2-yl)propanoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-((tert-butoxycarbonyl)amino)-3-(spiro[3.3]heptan-2-yl) propanoate to provide the title compound.

Intermediate R: 3-(bicyclo[2.2.1]heptan-1-yl)-2-((tert-butoxycarbonyl)amino)propanoic acid

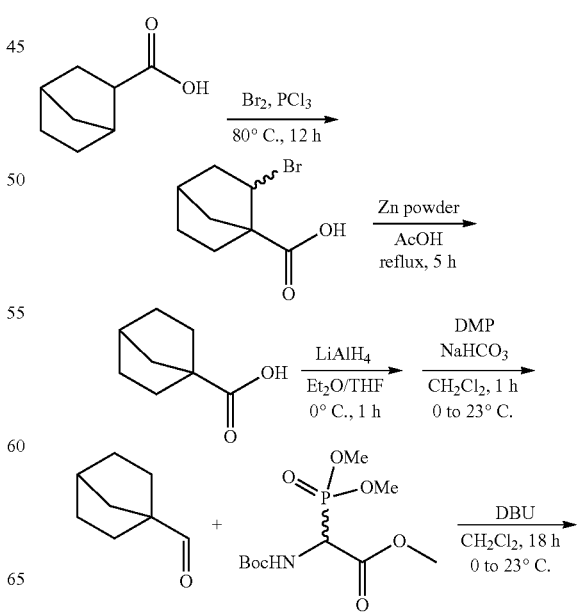

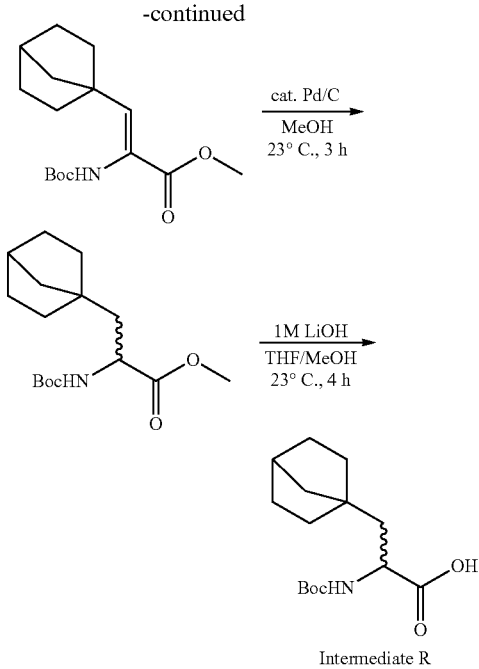

Step 1: Preparation of 2-bromobicyclo[2.2.1]heptane-1-carboxylic acid

To a 50 mL round bottom flask equipped with magnetic stir bar was added norbornane-2-carboxylic acid (4.7 g, 35.7 mmol, 1.0 equiv) and bromine (1.9 mL, 40.8 mmol, 1.1 equiv). The suspension was stirred at room temperature until a solution was obtained. $PCl_3$ (141 µL, 1.7 mmol, 0.05 equiv) was then added slowly and dropwise (significant exotherm observed). A reflux condenser was fitted to the flask with a nitrogen gas inlet and gas outlet (Tygon tubing) running into a scrubber solution of sodium sulfite (1 M, 200 mL). After the addition was complete, the reaction mixture was heated in an oil bath at 80° C. for 4 h. After this time, the reaction mixture was cooled to 10° C. and $PCl_3$ (2 ml, 24.2 mmol, 0.68 equiv) was added dropwise. The reaction mixture was again heated to 80° C. for 8 h. The resulting dark orange mixture was then cooled to room temperature and diluted with ether (500 mL). The ethereal solution was transferred to a 1 L separation funnel and washed with 1 M sodium sulfite (2×300 mL), water (1×200 mL), and brine (1×200 mL). The organic layer was dried over $MgSO_4$, filtered, and concentrated under reduced pressure to afford an oil. Ice cold pentane (30 mL) was then added to the crude product and the mixture was stirred vigorously. After 20 min, a fine white precipitate formed, which was filtered and washed with pentane (10 mL) and then air dried under a gentle vacuum to afford the title product as a white solid material.

Step 2: Preparation of bicyclo[2.2.1]heptane-1-carboxylic acid

To a 50 mL round bottom flask equipped with magnetic stir bar and refluxing condenser was added zinc powder (<10 micron, 4.8 g, 73 mmol, 10 equiv) and acetic acid (6.7 mL). While vigorously stirring the heterogeneous mixture, 2-bromobicyclo[2.2.1]heptane-1-carboxylic acid (1.6 g, 7.3 mmol, 1.0 equiv) was added. A second portion of acetic acid (6.7 mL) was applied to rinse the walls of the flask. The reaction mixture was brought to a gentle reflux in an oil bath for 5 h. The reaction mixture was cooled to room temperature, filtered through a pad of Celite on a plastic sintered funnel, and washed with acetic acid (10 mL) and ethyl acetate (15 mL). The filtrate was concentrated under reduced pressure, water (10 mL) was added, and then the mixture was stirred vigorously to induce precipitation. The precipitate was collected by filtration, washed with water, and dried under vacuum for 18 h. Pentane (10 mL) was then added, and the mixture was stirred vigorously for 20 min during which time a fine white precipitate formed. The resulting precipitate was filtered, washed with pentane (5 mL), and air dried to afford the title product as a white solid.

Step 3: Preparation of bicyclo[2.2.1]heptane-1-carbaldehyde

Prepared in a similar manner as tert-butyl (1-formylcyclohexyl)carbamate (step 1, intermediate F) using bicyclo[2.2.1]heptane-1-carboxylic acid to provide the title compound.

Steps 4-6: Preparation of 3-(bicyclo[2.2.1]heptan-1-yl)-2-((tert-butoxycarbonyl)amino)propanoic acid Steps 4-6 were performed in the same manner as in steps 2-4 for the synthesis of intermediate Q starting with bicyclo[2.2.1]heptane-1-carbaldehyde.

PREPARATION OF EXAMPLES

Example 1: (2S,4S)-1-((R)-2-(2-naphthamido)-3-cyclohexylpropanoyl)-N-(1-(2-amino-2-oxoacetyl)cyclobutyl)-4-(5-(2-hydroxypropan-2-yl)-1H-1,2,3-triazol-1-yl)pyrrolidine-2-carboxamide

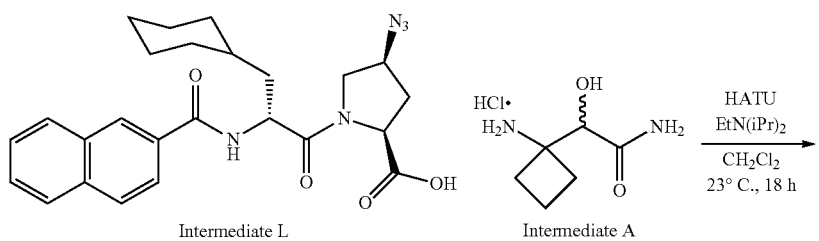

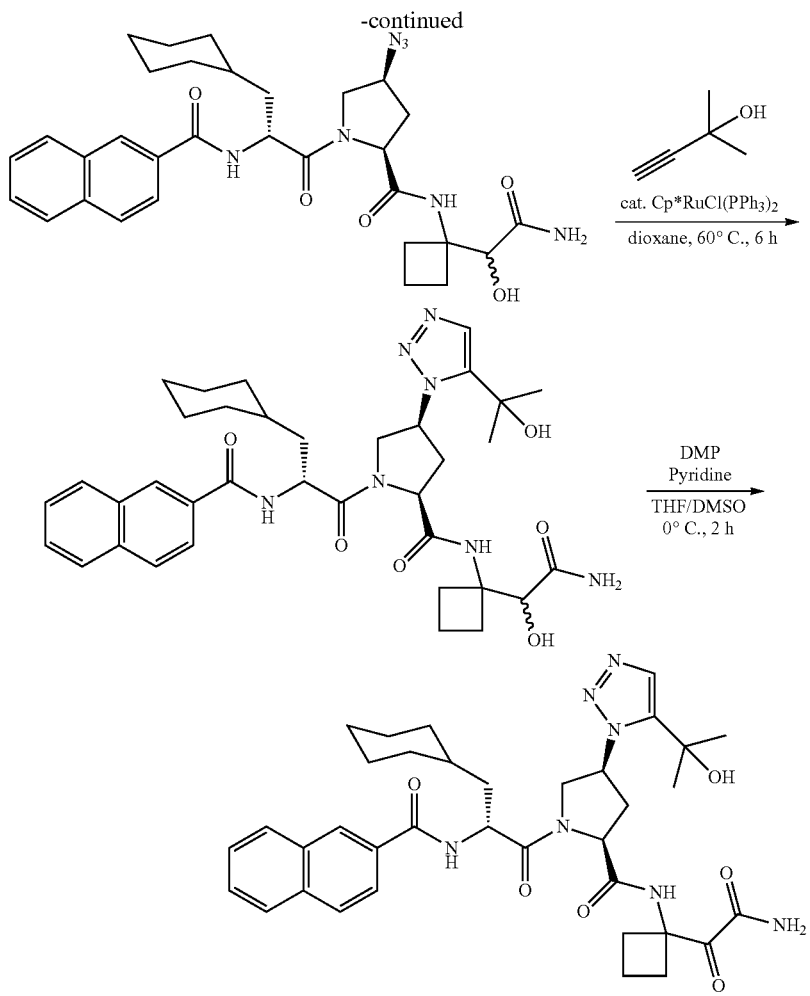

Example 1

Step 1: Preparation of (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide Into a 100 mL round-bottom flask, equipped with a magnetic stir bar and under nitrogen was added intermediate L (816 mg, 1.8 mmol, 1.0 equiv), intermediate A (350 mg, 1.9 mmol, 1.1 equiv) and HATU (737 mg, 1.9 mmol, 1.1 equiv). The solids were suspended in $CH_2Cl_2$ (anhydrous, 5 mL), treated with $EtN(iPr)_2$ (615 µL, 3.5 mmol, 2.0 equiv) and the reaction mixture was stirred at room temperature for 1 hour. LCMS analysis revealed conversion to product. The reaction mixture was quenched with 1 M HCl (30 mL) and extracted with $CH_2Cl_2$ (3×30 mL) using a Cl-phase separator cartridge. The combined organic extracts were concentrated under reduced pressure. The residue was purified by column chromatography on the ISCO Rf (40 g silica gel column+20 g pre-cartridge), eluting with 100:0 to 90:10 $CH_2Cl_2$:MeOH as a gradient over 20 min. The title product was obtained as a solid.

Step 2: Preparation of (2S,4S)-1-((R)-2-(2-naphthamido)-3-cyclohexylpropanoyl)-N-(1-(2-amino-1-hydroxy-2-oxoethyl)cyclobutyl)-4-(5-(2-hydroxypropan-2-yl)-1H-1,2,3-triazol-1-yl)pyrrolidine-2-carboxamide Prepared in a similar manner as methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate (step 1, intermediate M) using (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide to provide the title compound.

Step 3: Preparation of (2S,4S)-1-((R)-2-(2-naphthamido)-3-cyclohexylpropanoyl)-N-(1-(2-amino-2-oxoacetyl)cyclobutyl)-4-(5-(2-hydroxypropan-2-yl)-1H-1,2,3-triazol-1-yl)pyrrolidine-2-carboxamide Into a 25 mL round-bottom flask equipped with a magnetic stir bar and under nitrogen was added (2S,4S)-1-((R)-2-(2-naphthamido)-3-cyclohexylpropanoyl)-N-(1-(2-amino-1-hydroxy-2-oxoethyl) cyclobutyl)-4-(5-(2-hydroxypropan-2-yl)-1H-1,2,3-triazol-1-yl)pyrrolidine-2-carboxamide (180 mg, 0.27 mmol, 1.0 equiv), THF (2 mL), DMSO (0.5 mL) and pyridine (3 drops). The solution was cooled to 0° C. and DMP (907 mg, 2.14 mmol, 8.0 equiv) was added in two portions over 15 min. The mixture was stirred for 2 hours at 0° C. LCMS revealed approximately 60% conversion. In order to prevent further formation of impurities, the reaction mixture was quenched at this point by adding 2 mL of 10% aq. $Na_2S_2O_3$ and the mixture was stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (C18 column 26 g) eluting with 70:30 to 0:100 $H_2O$:MeCN+0.1% HCOOH as a gradient over 25 min. The desired peaks were concentrated under reduced pressure and dried under vacuum to afford the title compound as a white solid. MS (ESI+) 672 (M+1)$^{\oplus}$ The following compounds, examples 2 and 3, were prepared in a similar manner as example 1, from intermediates B and C, respectively.

| Example | Structure | MW | MS (ESI+) |
|---|---|---|---|
| 2 | (2S,4S)-1-((R)-2-(2-naphthamido)-3-cyclohexylpropanoyl)-N-(1-(2-amino-2-oxoacetyl)cyclopropyl)-4-(5-(2-hydroxypropan-2-yl)-1H-1,2,3-triazol-1-yl)pyrrolidine-2-carboxamide | 657.77 | 658 (M + 1)$^{\oplus}$ |
| 3 | (2S,4S)-1-((R)-2-(2-naphthamido)-3-cyclohexylpropanoyl)-N-(1-(2-amino-2-oxoacetyl)cyclopentyl)-4-(5-(2-hydroxypropan-2-yl)-1H-1,2,3-triazol-1-yl)pyrrolidine-2-carboxamide | 685.83 | 686 (M + 1)$^{\oplus}$ |

Example 4: (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

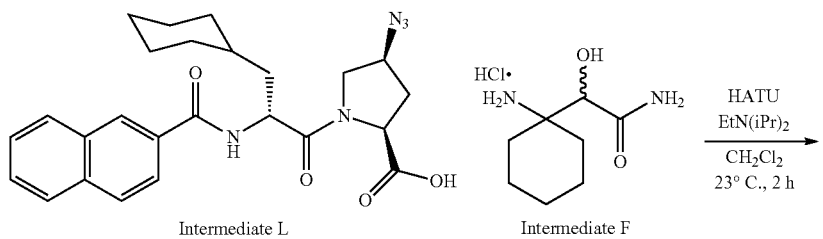

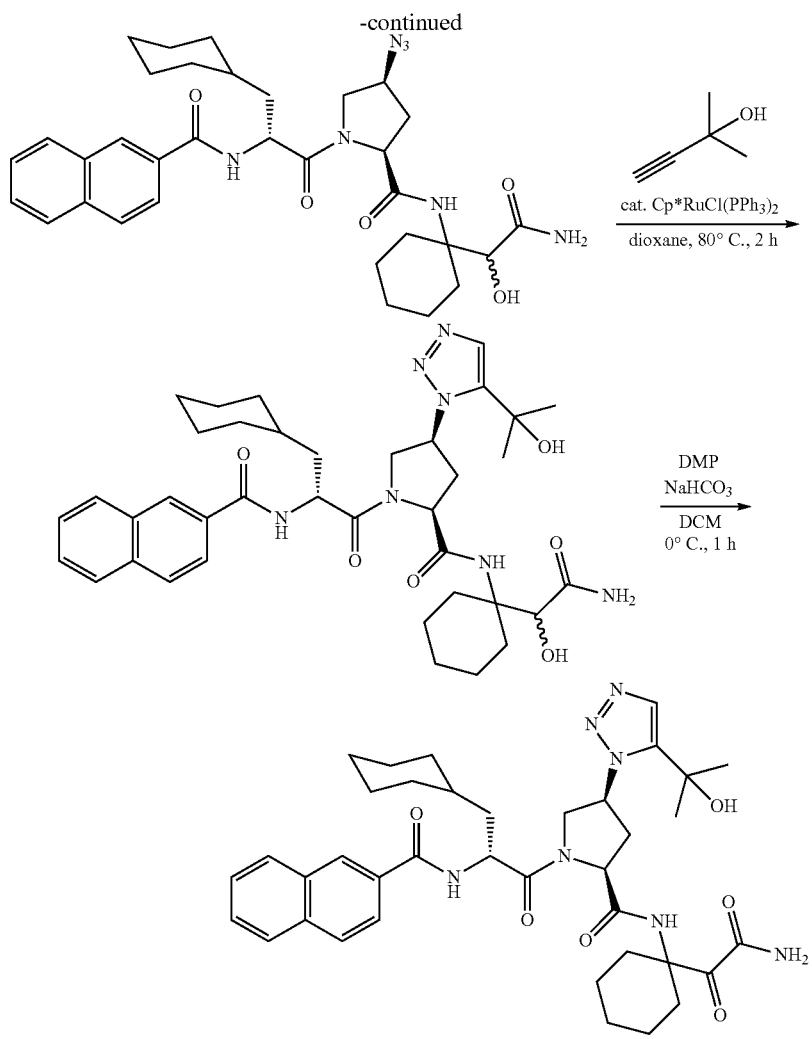

Example 4

Step 1: Preparation of (2S,4S)-1-((R)-2-(2-naphthamido)-3-cyclohexylpropanoyl)-N-(1-(2-amino-1-hydroxy-2-oxoethyl)cyclohexyl)-4-azidopyrrolidine-2-carboxamide Into a 50 mL round-bottom flask, equipped with a magnetic stir bar and under nitrogen was added intermediate L (326 mg, 0.70 mmol, 1.0 equiv), intermediate F (0.85 mmol, 1.2 equiv) and HATU (294 mg, 0.77 mmol, 1.1 equiv). The solids were suspended in $CH_2Cl_2$ (anhydrous, 2 mL), treated with EtN(iPr)$_2$ (367 μL, 2.1 mmol, 3.0 equiv) and the reaction mixture was stirred at room temperature for 2 h. LCMS analysis revealed conversion to product. The reaction mixture was quenched with 1 M HCl (15 mL) and extracted with $CH_2Cl_2$ (3×10 mL) using a Cl-phase separator cartridge. The combined organic extracts were concentrated under reduced pressure. The residue was purified by column chromatography on the ISCO Rf (24 g Gold silica gel column+5 g pre-cartridge), eluting with 100:0 to 90:10 $CH_2Cl_2$:MeOH as a gradient over 25 min. The desired fractions were concentrated under reduced pressure and dried under vacuum to provide the title compound.

Step 2: Preparation of (2S,4S)-1-((R)-2-(2-naphthamido)-3-cyclohexylpropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide Into a 25 mL round-bottom flask equipped with a magnetic stir bar, refluxing condenser and under nitrogen was added (2S,4S)-1-((R)-2-(2-naphthamido)-3-cyclohexylpropanoyl)-N-(1-(2-amino-1-hydroxy-2-oxoethyl)cyclohexyl)-4-azidopyrrolidine-2-carboxamide (350 mg, 0.57 mmol, 1.0 equiv), 2-methylbut-3-yn-2-ol (113 μL, 1.14 mmol, 2.0 equiv), pentamethylcyclopentadienylbis(triphenylphosphine)ruthenium (II) chloride (48 mg, 0.06 mmol, 0.1 equiv) and dioxane (3 mL). This red solution was sparged with nitrogen for 15 min, capped and heated in an oil bath at 80° C. under nitrogen for 2 h. After this time, the mixture was cooled to room temperature and loaded onto a 12 g silica gel pre-cartridge and dried. Purification was conducted by column chromatography on the ISCO Rf (24 g Gold silica gel column) eluting with 100:0 to 90:10 DCM:MeOH as a gradient over 25 min. The desired fractions were concentrated under reduced pressure and dried under vacuum to provide the title compound.

Step 3: Preparation of (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Into a 50 mL round-bottom flask equipped with a magnetic stir bar and under nitrogen was added (2S,4S)-1-((R)-2-(2-naphthamido)-3-cyclohexylpropanoyl)-N-(1-(2-amino-1-hydroxy-2-oxoethyl) cyclohexyl)-4-(5-(2-hydroxypropan-2-yl)-1H-1,2,3-triazol-1-yl)pyrrolidine-2-carboxamide (150 mg, 0.21 mmol, 1.0 equiv), NaHCO$_3$ (36 mg, 0.43 mmol, 2.0 equiv) and DCM (2 mL). The suspension was cooled to 0° C. in an ice bath and DMP (109 mg, 0.26 mmol, 1.2 equiv) was added. The mixture was stirred for 1 hour at 0° C. LCMS revealed approximately 70% conversion. Another 0.25 equiv of DMP (23 mg) was added and the reaction mixture was stirred for 30 min. LCMS revealed over 90% conversion. The reaction mixture was quenched with 10 mL of 10% aq. Na$_2$S$_2$O$_3$ and was stirred at room temperature for 30 min. The mixture was extracted with DCM (3×10 mL) using a Cl-phase separator cartridge. The combined organic extracts were concentrated under reduced pressure and loaded onto a 5 g C18 pre-cartridge. Purification was conducted by reverse-phase chromatography on the ISCO Rf (13 g Gold C18 column) eluting with 90:10 to 20:80 H$_2$O:MeCN+0.1% HCOOH as a gradient over 20 min. The desired peaks were concentrated under reduced pressure and dried under vacuum to afford the title compound as a white solid. MS (ESI+): 700 (M+1)$^\oplus$; $^1$H NMR (300 MHz, DMSO-d$_6$) δ 8.86-8.72 (m, 1H), 8.58-8.44 (m, 1H), 8.19-8.06 (m, 1H), 8.06-7.86 (m, 4H), 7.70-7.46 (m, 3H), 7.44-7.32 (m, 1H), 7.32-7.23 (m, 1H), 5.79-5.52 (m, 2H), 5.03-4.80 (m, 1H), 4.56-4.38 (m, 1H), 4.38-4.16 (m, 1H), 4.16-3.95 (m, 1H), 2.85-2.55 (m, 2H), 2.26-1.95 (m, 2H), 1.94-1.44 (m, 15H), 1.44-1.20 (m, 6H), 1.20-0.72 (m, 6H) ppm.

The following compounds, examples 5 and 6, were prepared in a similar manner as example 1, from intermediates D and E, respectively.

| Example | Structure | MW | MS (ESI+) |
|---------|-----------|------|-----------|
| 5 | (2S,4S)-1-((R)-2-(2-naphthamido)-3-cyclohexylpropanoyl)-N-(1-(2-amino-2-oxoacetyl)cycloheptyl)-4-(5-(2-hydroxypropan-2-yl)-1H-1,2,3-triazol-1-yl)pyrrolidine-2-carboxamide | 713.88 | 714 (M + 1)$^\oplus$ |
| 6 | (2S,4S)-1-((R)-2-(2-naphthamido)-3-cyclohexylpropanoyl)-N-(1-(2-amino-2-oxoacetyl)cyclooctyl)-4-(5-(2-hydroxypropan-2-yl)-1H-1,2,3-triazol-1-yl)pyrrolidine-2-carboxamide | 727.91 | 728 (M + 1)$^\oplus$ |

Example 7: (1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid

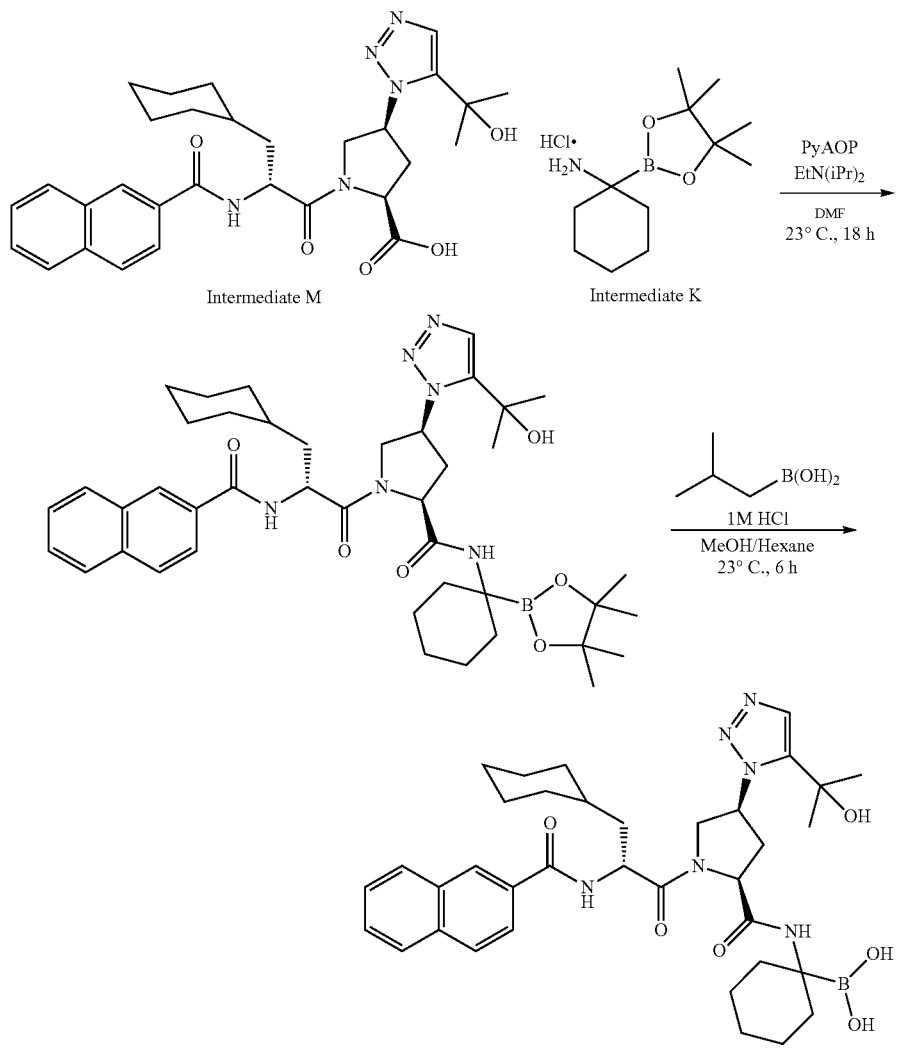

Intermediate M

Intermediate K

Example 7

Step 1: Preparation of (2S,4S)-1-((R)-2-(2-naphthamido)-3-cyclohexylpropanoyl)-4-(5-(2-hydroxypropan-2-yl)-1H-1,2,3-triazol-1-yl)-N-(1-(4,4,5,5-tetramethyl-1,3,2-dioxaborolan-2-yl)cyclohexyl)pyrrolidine-2-carboxamide Into a 4 mL sample vial equipped with a magnetic stir bar and under nitrogen was added intermediate M (103 mg, 0.19 mmol, 1.0 equiv), intermediate K (60 mg, 0.23 mmol, 1.2 equiv), PyAOP (120 mg, 0.23 mmol, 1.2 equiv), DMF (1 mL) and EtN(iPr)$_2$ (66 μL, 0.38 mmol, 2.0 equiv). The yellow solution was stirred at room temperature for 18 hours. LCMS revealed approximately 40% product formation. The reaction mixture was quenched with water (5 mL) and extracted with DCM (3×5 mL) using a Cl-phase separatory cartridge. The combined organic extracts were concentrated under reduced pressure. The residue was purified by column chromatography on Fluorosil (3 cm×8 cm), eluting with 95:5 DCM:MeOH. The desired fractions were concentrated under reduced pressure and dried under vacuum for 18 h to afford the title compound as a white solid.

Step 2: Preparation of (1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)boronic acid Into an 8 mL sample vial equipped with a magnetic stir bar and under nitrogen was added (2S,4S)-1-((R)-2-(2-naphthamido)-3-cyclohexylpropanoyl)-4-(5-(2-hydroxypropan-2-yl)-1H-1,2,3-triazol-1-yl)-N-(1-(4,4,5,5-tetramethyl-1,3,2-dioxaborolan-2-yl)cyclohexyl)pyrrolidine-2-carboxamide (30 mg, 0.04 mmol, 1.0 equiv), isobutyl boronic acid (20 mg, 0.20 mmol, 5.0 equiv) in methanol (0.5 mL) and hexanes (0.5 mL). The reaction mixture was treated with 1 M HCl in water (160 μL, 0.16 mmol, 4.0 equiv) and the biphasic suspension was stirred rigorously at room temperature for 6 h. LCMS analysis revealed complete conversion of starting material to desired product. The bottom methanol layer was removed and washed with hexanes (2×2 mL). The top hexane layer was further extracted with methanol (1 mL), and the combined methanol layers were concentrated under reduced pressure. Without further purification, the crude was further dried under vacuum for 18 h to afford the title compound. MS (ESI+) 656 (M-17)$^{\oplus}$ Example 8: (2S,4R)-1-((R)-2-(2-naphthamido)-3-cyclohexylpropanoyl)-N-(1-(2-amino-2-oxoacetyl)cyclohexyl)-4-(piperidin-1-yl)pyrrolidine-2-carboxamide

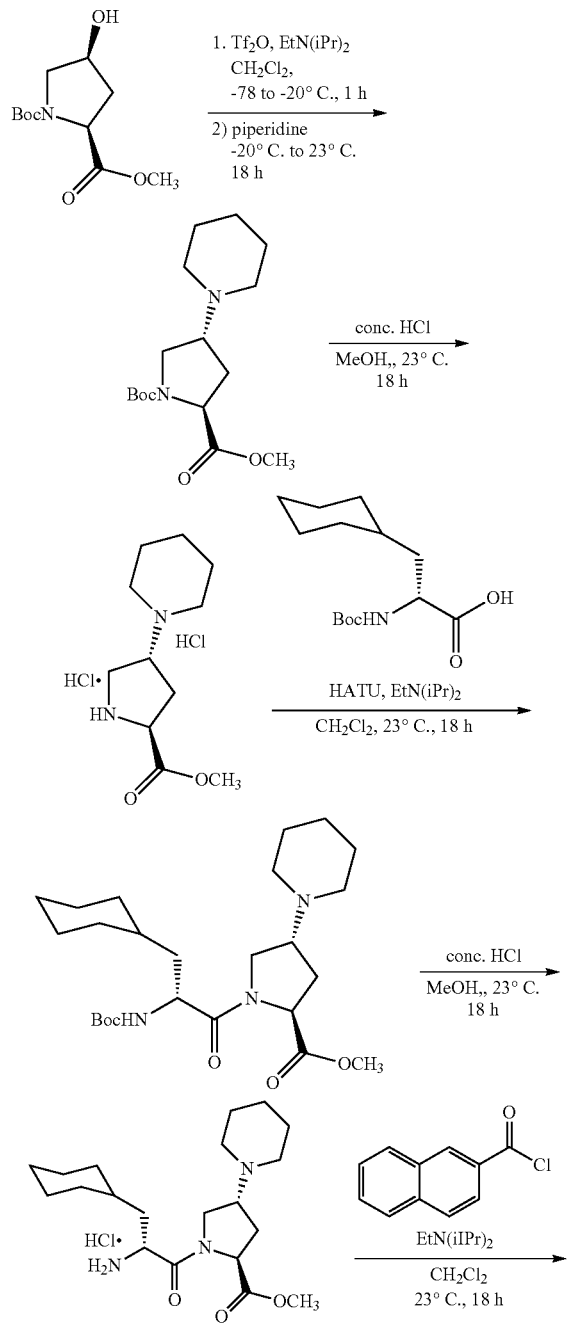

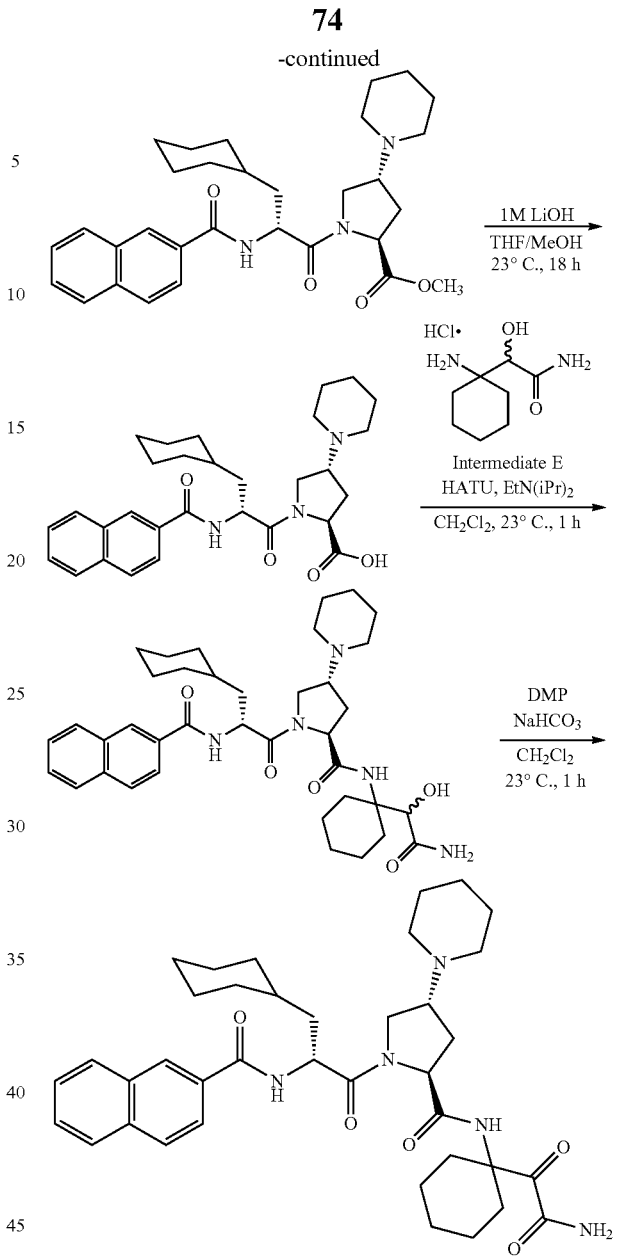

Example 8

Step 1: Preparation of 1-(tert-butyl) 2-methyl (2S,4R)-4-(piperidin-1-yl)pyrrolidine-1,2-dicarboxylate Into a 1 L round-bottom flask equipped with a magnetic stir bar and under nitrogen was weighted 1-(tert-butyl) 2-methyl (2S,4S)-4-hydroxypyrrolidine-1,2-dicarboxylate (19.8 g, 80.7 mmol, 1.0 equiv). The solid was dissolved in CH$_2$Cl$_2$ (330 mL) and cooled to −78° C. in a dry ice/acetone Dewar. The cold solution was treated with EtN(iPr)$_2$ (17.0 mL, 96.9 mmol, 1.2 equiv) and then triflic anhydride (14.7 mL, 88.8 mmol, 1.1 equiv) was added dropwise over 5 minutes. After stirring at −78° C. for 20 min, the mixture was warmed to −10° C. and piperidine (15.9 mL, 161.4 mmol, 2.0 equiv) was added dropwise over 15 minutes. The reaction mixture was allowed to warm to room temperature with stirring for 18 h. LCMS analysis revealed product formation. The reaction mixture was quenched with 200 mL sat. aq.

NaHCO$_3$ and the aqueous layer was extracted with DCM (3×). The combined organic extracts were washed with brine (1×), dried over MgSO$_4$, filtered and concentrated under reduced pressure. The residue was purified by column chromatography through silica gel (2×120 g), eluting with 20:80 to 80:20 EtOAc:Hexanes as a gradient over 34 min to afford the the title compound.

Step 2: Preparation of methyl (2S,4R)-4-(piperidin-1-yl)pyrrolidine-2-carboxylate dihydrochloride Prepared in a similar manner as methyl (2S,4S)-4-azidopyrrolidine-2-carboxylate hydrochloride (step 3, intermediate L) using 1-(tert-butyl) 2-methyl (2S,4R)-4-(piperidin-1-yl)pyrrolidine-1,2-dicarboxylate to provide the title compound.

Step 3: Preparation of methyl (2S,4R)-1-((R)-2-((tert-butoxycarbonyl)amino)-3-cyclohexyl propanoyl)-4-(piperidin-1-yl)pyrrolidine-2-carboxylate Prepared in a similar manner as methyl (2S,4S)-4-azido-1-((R)-2-((tert-butoxycarbonyl)amino)-3-cyclohexylpropanoyl)pyrrolidine-2-carboxylate (step 4, intermediate L) using methyl (2S,4R)-4-(piperidin-1-yl)pyrrolidine-2-carboxylate dihydrochloride to provide the title compound.

Step 4: Preparation of methyl (2S,4R)-1-((R)-2-amino-3-cyclohexylpropanoyl)-4-(piperidin-1-yl)pyrrolidine-2-carboxylate hydrochloride Prepared in a similar manner as methyl (2S,4S)-4-azidopyrrolidine-2-carboxylate hydrochloride (step 3, intermediate L) using methyl (2S,4R)-1-((R)-2-((tert-butoxycarbonyl)amino)-3-cyclohexyl propanoyl)-4-(piperidin-1-yl)pyrrolidine-2-carboxylate to provide the title compound.

Step 5: Preparation of methyl (2S,4R)-1-((R)-2-(2-naphthamido)-3-cyclohexylpropanoyl)-4-(piperidin-1-yl)pyrrolidine-2-carboxylate To a stirred solution of methyl (2S,4R)-1-((R)-2-amino-3-cyclohexylpropanoyl)-4-(piperidin-1-yl)pyrrolidine-2-carboxylate hydrochloride (47.7 mmol, 1.0 equiv) and 2-naphthoyl chloride (10.9 g, 57.2 mmol, 1.2 equiv) in DCM (160 mL) was added iPr$_2$EtN (26.5 mL, 152.6 mmol, 3.2 equiv) and the reaction mixture was stirred at 23° C. for 18 hours. The reaction was quenched with 250 mL of water and the aqueous layer was extracted with DCM (3×). The combined organic extracts were washed with brine (1×), dried over MgSO$_4$, filtered and concentrated under reduced pressure. The residue was purified by column chromatography through silica gel (2×120 g), eluting with 30:70 to 100:0 EtOAc:Hexanes as a gradient over 47 min to afford the title compound.

Step 6: Preparation of (2S,4R)-1-((R)-2-(2-naphthamido)-3-cyclohexylpropanoyl)-4-(piperidin-1-yl)pyrrolidine-2-carboxylic acid A solution of methyl (2S,4R)-1-((R)-2-(2-naphthamido)-3-cyclohexylpropanoyl)-4-(piperidin-1-yl)pyrrolidine-2-carboxylate (12.7 g, 24.6 mmol, 1.0 equiv) in MeOH (35 mL) and THF (35 mL). The resulting solution was treated with 1 M aqueous LiOH (36.8 mL, 36.8 mmol, 1.5 equiv). The solution was stirred at room temperature for 18 hours. The reaction mixture was quenched with acetic acid (2.1 mL, glacial, 17.5 M, 1.5 equiv), yielding a thick white precipitate. The organic solvents were removed under reduced pressure. The resulting aqueous suspension was stirred vigorously overnight. The precipitate was collected by vacuum filtration, washed with water and further dried under high vacuum to afford the title compound as a white solid.

Step 7: Preparation of (2S,4R)-1-((R)-2-(2-naphthamido)-3-cyclohexylpropanoyl)-N-(1-(2-amino-1-hydroxy-2-oxoethyl)cyclohexyl)-4-(piperidin-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4R)-1-((R)-2-(2-naphthamido)-3-cyclohexylpropanoyl)-4-(piperidin-1-yl)pyrrolidine-2-carboxylic acid and intermediate F to provide the title compound.

Step 8: Preparation of (2S,4R)-1-((R)-2-(2-naphthamido)-3-cyclohexylpropanoyl)-N-(1-(2-amino-2-oxoacetyl)cyclohexyl)-4-(piperidin-1-yl)pyrrolidine-2-carboxamide Prepared in a similar manner as (2S,4S)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide (step 3, example 4) using (2S,4R)-1-((R)-2-(2-naphthamido)-3-cyclohexylpropanoyl)-N-(1-(2-amino-1-hydroxy-2-oxoethyl)cyclohexyl)-4-(piperidin-1-yl)pyrrolidine-2-carboxamide to provide the title compound. MS (ESI+) 658 (M+1)$^{\oplus}$ Example 9: (2S,3R,4R)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)-3-methoxypyrrolidine-2-carboxamide

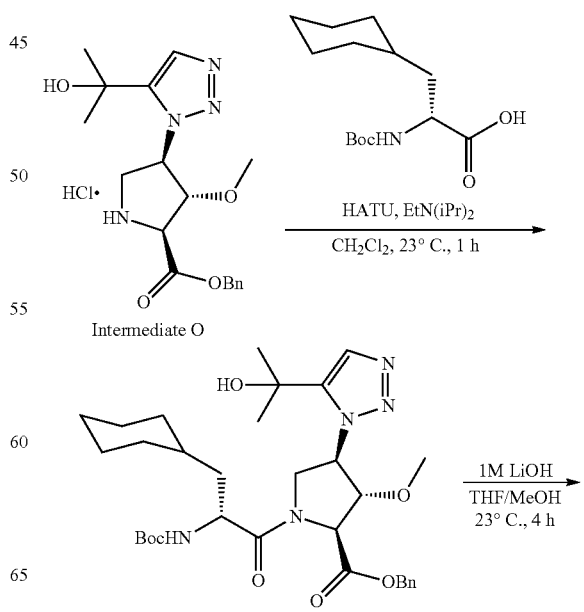

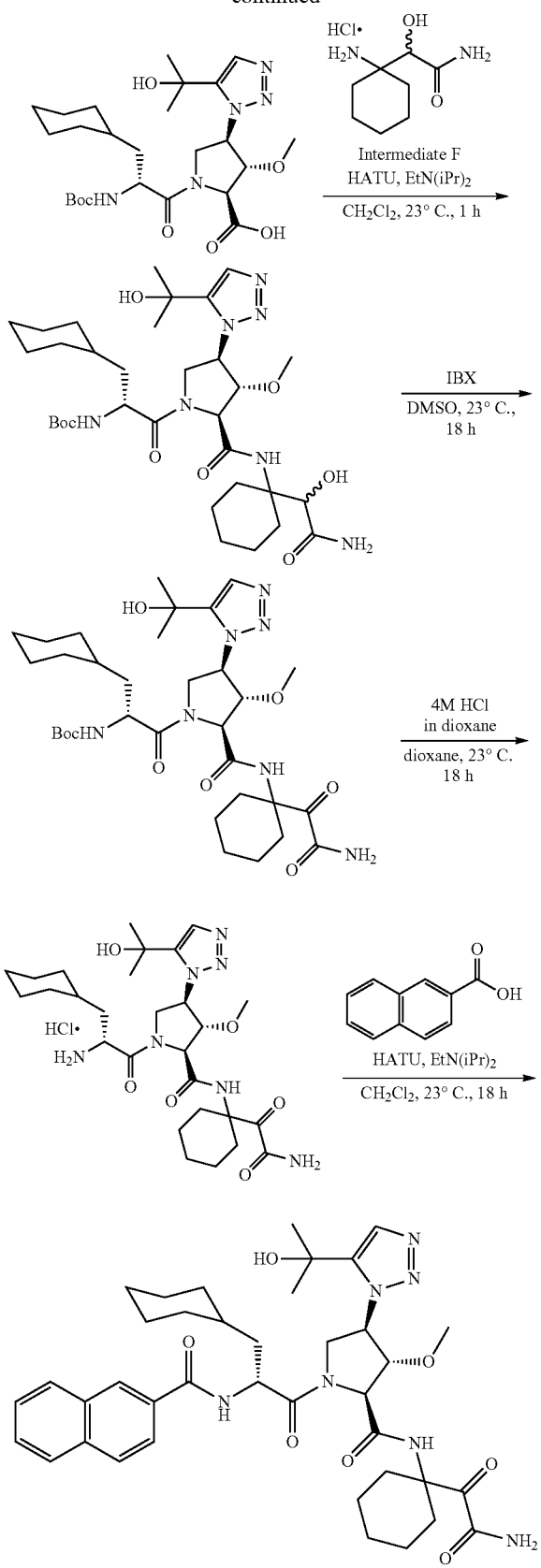

Example 9

Step 1: Preparation of benzyl (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using intermediate O and (R)-2-((tert-butoxycarbonyl)amino)-3-cyclohexylpropanoic acid to provide the title compound.

Step 2: Preparation of (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using benzyl (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylate to provide the title compound.

Step 3: Preparation of tert-butyl ((2R)-1-((2S,3R,4R)-2-((1-(2-amino-1-hydroxy-2-oxoethyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,3R,4R)-1-((R)-2-((tert-butoxycarbonyl)amino)-3-cyclohexylpropanoyl)-4-(5-(2-hydroxypropan-2-yl)-1H-1,2,3-triazol-1-yl)-3-methoxypyrrolidine-2-carboxylic acid and intermediate F to provide the title compound.

Step 4: Preparation of tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate Into a 50 mL round bottom flask equipped with a magnetic stir bar and under nitrogen was added tert-butyl ((2R)-1-((2S,3R,4R)-2-((1-(2-amino-1-hydroxy-2-oxoethyl)cyclohexyl)carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate (370 mg, 0.55 mmol, 1.0 equiv) and DMSO (2 mL). The solution was treated with IBX (679 mg, 1.1 mmol, 2.0 equiv) and the reaction mixture was stirred at room temperature for 18 h. LCMS revealed complete conversion of starting material and product formation. The reaction mixture was directly loaded onto a reverse-phase 5 g pre-cartridge and dried. Purification was conducted by reverse-phase column chromatography on the ISCO Rf (C18 Gold 15.5 g column) eluting with 80:20 to 20:80 $H_2O$:MeCN+0.1% HCOOH as a gradient over 20 min. The desired material was concentrated under reduced pressure and dried under vacuum to afford the title product as a white solid.

Step 5: Preparation of (2S,3R,4R)—N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)-3-methoxypyrrolidine-2-carboxamide hydrochloride Prepared in the same manner as 2-(1-aminocyclobutyl)-2-hydroxyacetamide hydrochloride (step 4, intermediate A). using tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl)carbamate to provide the title compound.

Step 6: Preparation of (2S,3R,4R)-1-((R)-2-(2-naphthamido)-3-cyclohexylpropanoyl)-N-(1-(2-amino-2-oxoacetyl)cyclohexyl)-4-(5-(2-hydroxypropan-2-yl)-1H-1,2,3-triazol-1-yl)-3-methoxypyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,3R,4R)—N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)-3-methoxypyrrolidine-2-carboxamide hydrochloride and 2-naphthoic acid to provide the title compound. MS (ESI+) 730 (M+1)⊕

Example 10: (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide

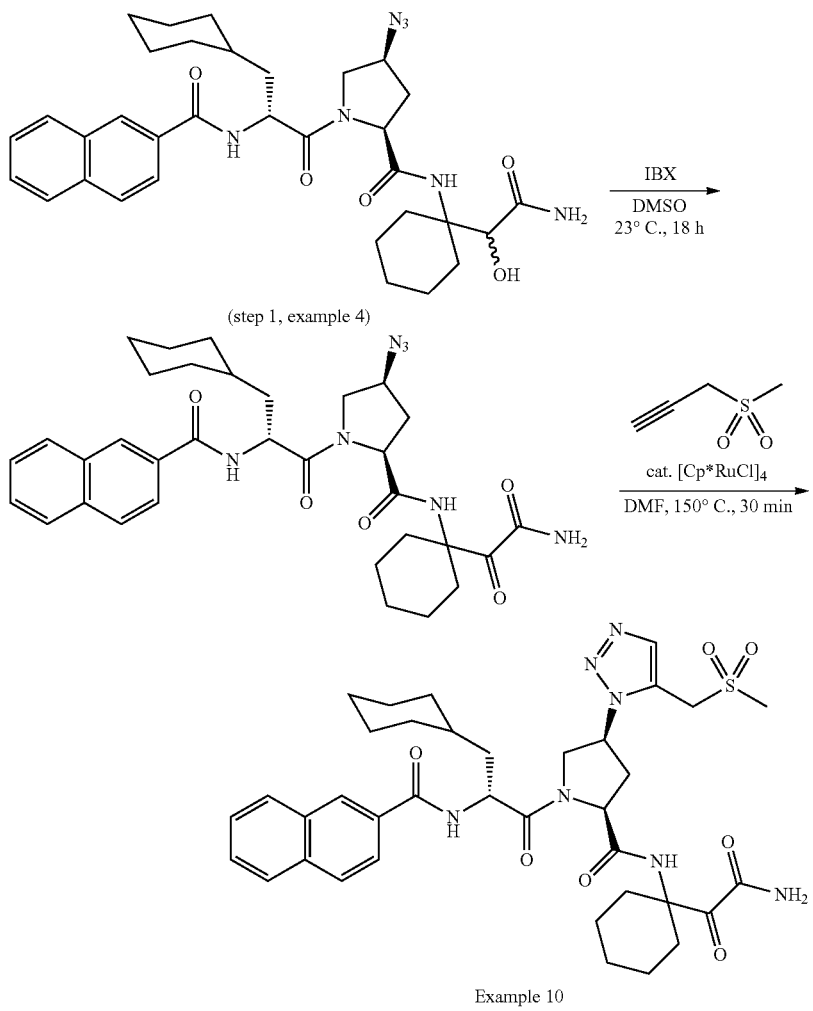

Example 10

Step 1: Preparation of (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) (2S,4S)-1-((R)-2-(2-naphthamido)-3-cyclohexylpropanoyl)-N-(1-(2-amino-1- hydroxy-2-oxoethyl)cyclohexyl)-4-azidopyrrolidine-2-carboxamide to provide the title compound.

Step 2: Preparation of (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide Into a 2.5 mL microwave vial with a magnetic stir bar was added (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide (25 mg, 0.04 mmol, 1.0 equiv), 3-methylsulfonyl-1-propyne (16 µL, 0.16 mmol, 4 equiv), [Cp*RuCl]₄ (4.5 mg, 0.004, 0.1 equiv) and DMF (anhydrous, 1 mL). The vial was sealed and heated to 150° C. for 30 min to yield a brown solution. LCMS revealed product formation. The mixture was loaded directly onto a 5 g C18 pre-cartridge and dried. Purification was conducted by reverse phase column chromatography on the ISCO Rf (15.5 g C18 Gold column) eluting with 80:20 to 0:100 H₂O:MeCN+0.1% HCOOH as a gradient over 20 min. The desired product was isolated as a beige solid, which was further dried under vacuum to afford the title product. MS (ESI+) 734 (M+1)⊕

The following compounds, examples 11, 12 and 13, were prepared in a similar manner as example 10 using 3-ethynyloxetan-3-ol, but-3-ynoic acid and N-(prop-2-yn-1-yl)cyclopropanesulfonamide, respectively, in step 2.

| Example | Structure | MW | MS (ESI+) |
|---|---|---|---|
| 11 | 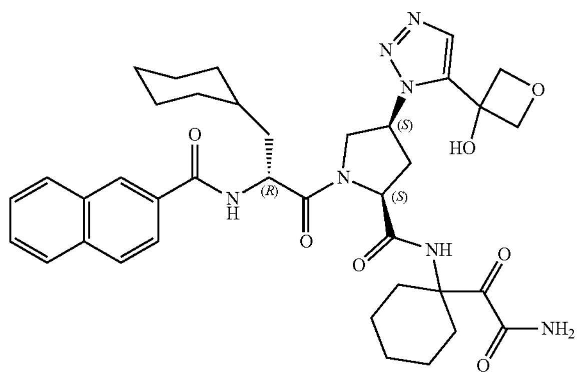 | 713.84 | 714 (M + 1)⊕ |

(2S,4S)-1-((R)-2-(2-naphthamido)-3-cyclohexylpropanoyl)-N-(1-(2-amino-2-oxoacetyl)cyclohexyl)-4-(5-(3-hydroxyoxetan-3-yl)-1H-1,2,3-triazol-1-yl)pyrrolidine-2-carboxamide

| 12 | | 699.81 | 700 (M + 1)⊕ |

2-(1-((3S,5S)-1-((R)-2-(2-naphthamido)-3-cyclohexylpropanoyl)-5-((1-(2-amino-2-oxoacetyl)cyclohexyl)carbamoyl)pyrrolidin-3-yl)-1H-1,2,3-triazol-5-yl)acetic acid

| Example | Structure | MW | MS (ESI+) |
|---|---|---|---|
| 13 | (2S,4S)-1-((R)-2-(2-naphthamido)-3-cyclohexylpropanoyl)-N-(1-(2-amino-2-oxoacetyl)cyclohexyl)-4-(5-(cyclopropanesulfonamidomethyl)-1H-1,2,3-triazol-1-yl)pyrrolidine-2-carboxamide | 774.94 | 775 (M + 1)⊕ |
Example 14: (2S,4S)—N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide
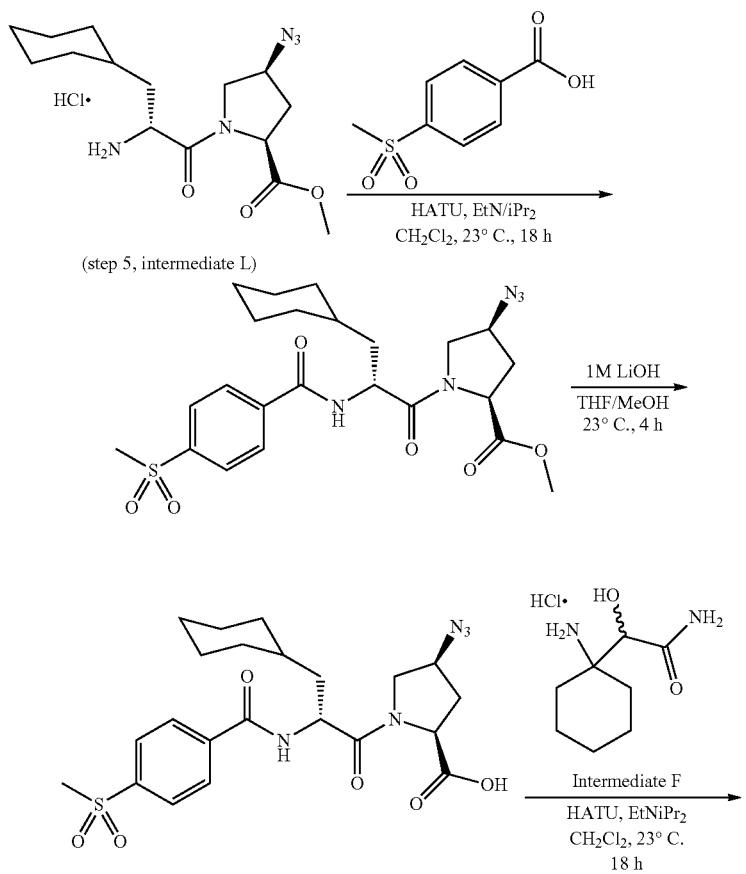

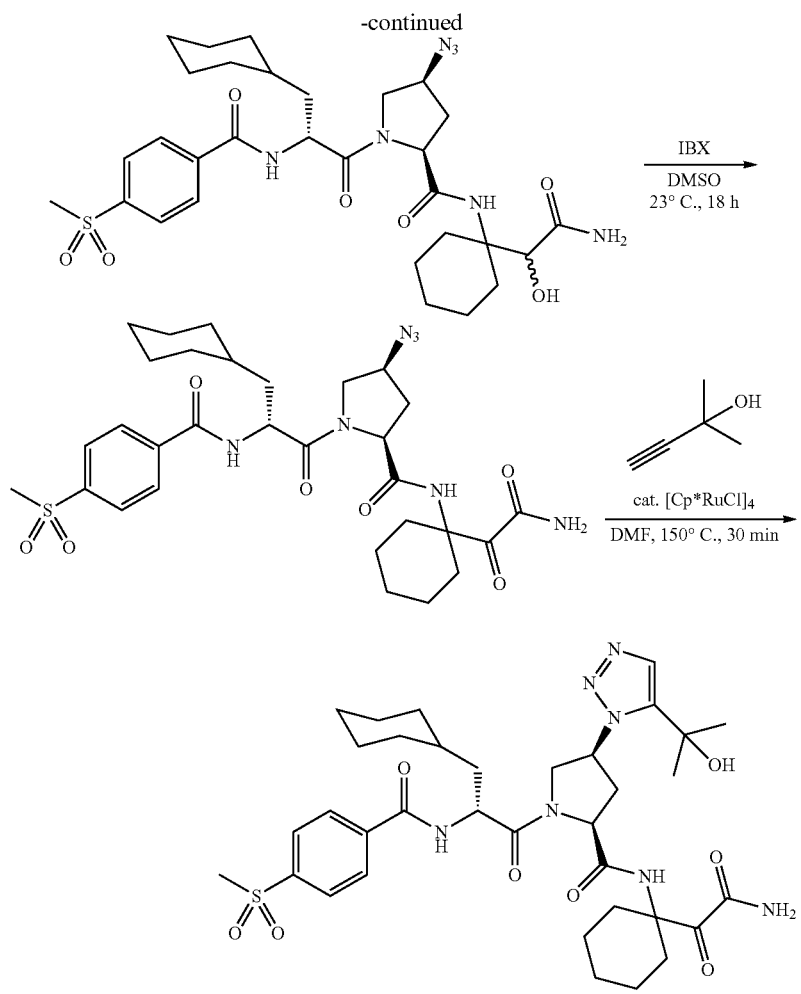

Example 14

Step 1: Preparation of (2S,4S)-methyl 4-azido-1-((R)-3-cyclohexyl-2-(4-(methylsulfonyl)benzamido)propanoyl)pyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-methyl 1-((R)-2-amino-3-cyclohexylpropanoyl)-4-azidopyrrolidine-2-carboxylate hydrochloride and 4-(methylsulfonyl)benzoic acid to provide the title compound.

Step 2: Preparation of (2S,4S)-4-azido-1-((R)-3-cyclohexyl-2-(4-(methylsulfonyl)benzamido) propanoyl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using (2S,4S)-methyl 4-azido-1-((R)-3-cyclohexyl-2-(4-(methylsulfonyl)benzamido)propanoyl)pyrrolidine-2-carboxylate to provide the title compound.

Step 3: Preparation of (2S,4S)—N-(1-(2-amino-1-hydroxy-2-oxoethyl)cyclohexyl)-4-azido-1-((R)-3-cyclohexyl-2-(4-(methylsulfonyl)benzamido)propanoyl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-4-azido-1-((R)-3-cyclohexyl-2-(4-(methylsulfonyl)benzamido) propanoyl) pyrrolidine-2-carboxylic acid and intermediate F to provide the title compound.

Step 4: Preparation of (2S,4S)—N-(1-(2-amino-2-oxoacetyl)cyclohexyl)-4-azido-1-((R)-3-cyclohexyl-2-(4-(methylsulfonyl)benzamido)propanoyl)pyrrolidine-2-carboxamide Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)—N-(1-(2-amino-1-hydroxy-2-oxoethyl)cyclohexyl)-4-azido-1-((R)-3-cyclohexyl-2-(4-(methylsulfonyl)benzamido)propanoyl) pyrrolidine-2-carboxamide to provide the title compound.

Step 5: Preparation of (2S,4S)—N-(1-(2-amino-2-oxoacetyl)cyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-2-oxoacetyl)cyclohexyl)-4-(5-((methylsulfonyl)methyl)-1H-1,2,3-triazol-1-yl)pyrrolidine-2-carboxamide (step 2, example 10) using (2S,4S)—N-(1-(2-amino-2-oxoacetyl)cyclohexyl)-4-azido-((R)-3-cyclohexyl-2-(4-(methylsulfonyl)benzamido)propanoyl)pyrrolidine-2-carboxamide and 2-methylbut-3-yn-2-ol to provide the title compound. MS (ESI+) 728 (M+1)⊕; ¹H NMR (300 MHz, CDCl₃) δ 8.80-7.75 (m, 6H), 7.75-6.62 (m, 4H), 6.12-5.50 (m, 2H), 5.40-4.75 (m, 2H), 4.75-4.0 (m, 4H), 3.80-2.80 (m, 2H), 2.75-0.45 (m, 29H) ppm.

The following compound examples 15 and 16 was prepared in a similar manner as example 14 using 3-ethynyloxetan-3-ol and prop-2-yne-1-sulfonic acid, respectively, in step 5

| Example | Structure | MW | MS (ESI+) |
|---|---|---|---|
| 15 | (2S,4S)-N-(1-(2-amino-2-oxoacetyl)cyclohexyl)-1-((R)-3-cyclohexyl-2-(4-(methylsulfonyl)benzamido)propanoyl)-4-(5-(3-hydroxyoxetan-3-yl)-1H-1,2,3-triazol-1-yl)pyrrolidine-2-carboxamide | 741.86 | 742 (M + 1)⊕ |
| 16 | (2S,4S)-N-(1-(2-amino-2-oxoacetyl)cyclohexyl)-1-((R)-3-cyclohexyl-2-(4-(methylsulfonyl)benzamido)propanoyl)-4-(5-((methylsulfonyl)methyl-1H-1,2,3-triazol-1-yl)pyrrolidine-2-carboxamide | 761.91 | 762 (M + 1)⊕ |

Example 17: (2S,4S)-1-((R)-2-(2-naphthamido)-3-cyclohexylpropanoyl)-N-(1-(2-amino-2-oxoacetyl)cyclohexyl)-4-(4-(2-hydroxypropan-2-yl)-1H-1,2,3-triazol-1-yl)pyrrolidine-2-carboxamide

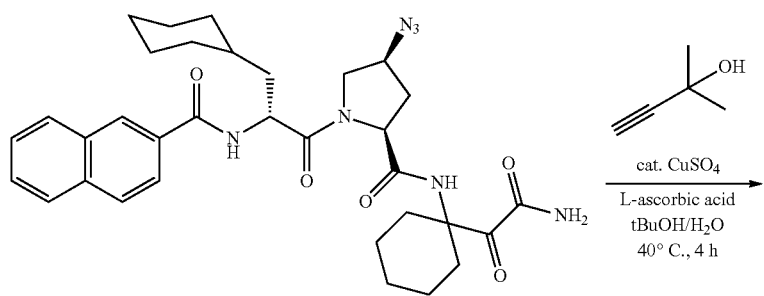

(step 1, example 10)

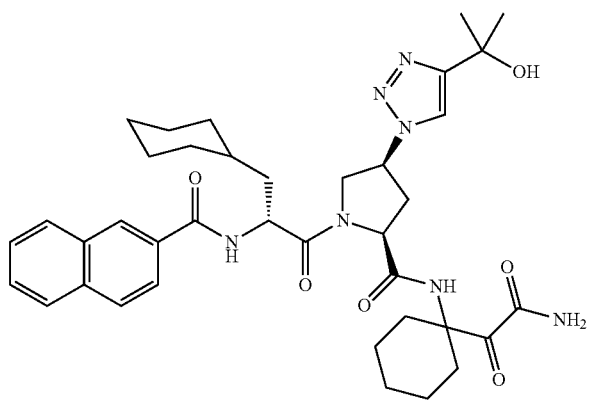

Example 17

Into an 8 mL sample vial equipped with a magnetic stir bar was added (2S,4S)-1-((R)-2-(2-naphthamido)-3-cyclohexylpropanoyl)-N-(1-(2-amino-2-oxoacetyl)cyclohexyl)-4-azidopyrrolidine-2-carboxamide (100 mg, 0.16 mmol, 1.0 equiv), 2-methylbut-3-yn-2-ol (40 µL, 0.41 mmol, 2.5 equiv), $CuSO_4$ (5 mg, 0.03 mmol, 0.2 equiv), L-ascorbic acid (29 mg, 0.16 mmol, 1.0 equiv) and $tBuOH:H_2O$ (1:1 v/v, 2 mL). The mixture was heated to 40° C. for 4 h. LCMS analysis revealed product formation. The reaction mixture was loaded onto a C18 5 g pre-cartridge and dried. Purification was conducted by reverse phase column chromatography on the ISCO Rf (15.5 g C18 Gold column) eluting with 80:20 to 10:90 $H_2O$:MeCN+0.1% HCOOH as a gradient over 20 min. The desired product was isolated as a beige solid, which was further dried under vacuum to afford the title product. MS (ESI+) 722 (M+23)$^\oplus$ The following compound, examples 18, was prepared in a similar manner as example 17 using 3-ethynyloxetan-3-ol.

| Example | Structure | MW | MS (ESI+) |
|---|---|---|---|
| 18 | 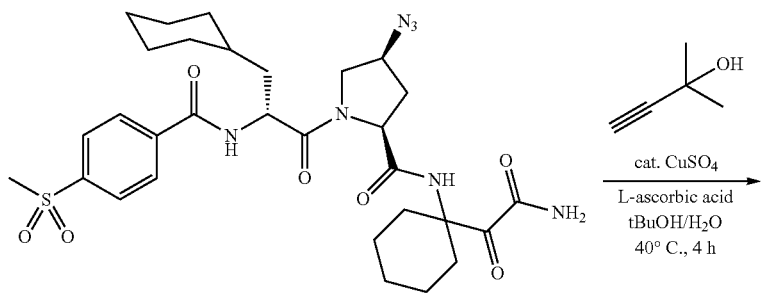<br>(2S,4S)-1-((R)-2-(2-naphthamido)-3-cyclohexylpropanoyl)-N-(1-(2-amino-2-oxoacetly)cyclohexyl)-4-(4-(3-hydroxyoxetan-3-yl)-1H-1,2,3-triazol-1-yl)pyrrolidine-2-carboxamide | 713.84 | 714 (M + 1)⁺ |
Example 19: (2S,4S)—N-(1-(2-amino-2-oxoacetyl)cyclohexyl)-1-((R)-3-cyclohexyl-2-(4-(methylsulfonyl)benzamido)propanoyl)-4-(4-(2-hydroxypropan-2-yl)-1H-1,2,3-triazol-1-yl)pyrrolidine-2-carboxamide
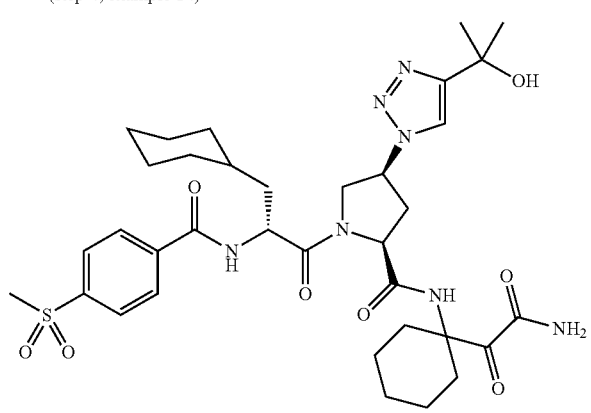
Example 19

Prepared in a similar manner as (2S,4S)-1-((R)-2-(2-naphthamido)-3-cyclohexylpropanoyl)-N-(1-(2-amino-2-oxoacetyl)cyclohexyl)-4-(4-(2-hydroxypropan-2-yl)-1H-1,2,3-triazol-1-yl)pyrrolidine-2-carboxamide (example 17) using (2S,4S)—N-(1-(2-amino-2-oxoacetyl)cyclohexyl)-4-azido-1-((R)-3-cyclohexyl-2-(4-(methylsulfonyl)benzamido)propanoyl)pyrrolidine-2-carboxamide to provide the title compound. MS (ESI+) 728 (M+1)⊕

The following compounds, examples 20 and 21, were prepared in a similar manner as example 19 using 3-ethynyloxetan-3-ol and 3-(methylsulfonyl)prop-1-yne, respectively.

| Example | Structure | MW | MS (ESI+) |
|---|---|---|---|
| 20 | 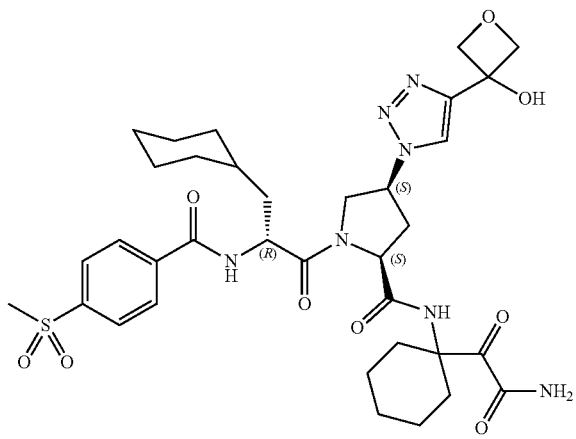 (2S,4S)-N-(1-(2-amino-2-oxoacetyl)cyclohexyl)-1-((R)-3-cyclohexyl-2-(4-(methylsulfonyl)benzamido)propanoyl)-4-(4-(3-hydroxyoxetan-3-yl)-1H-1,2,3-triazol-1-yl)pyrrolidine-2-carboxamide | 741.86 | 742 (M + 1)⊕ |
| 21 | 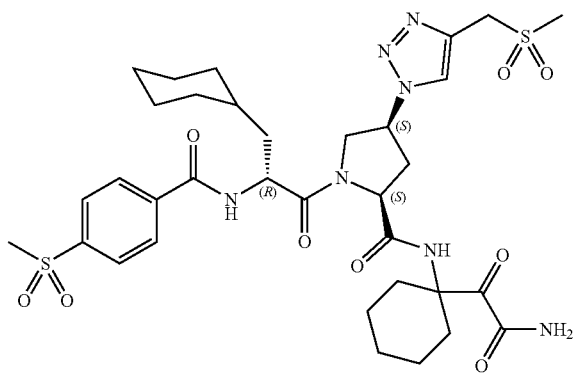 (2S,4S)-N-(1-(2-amino-2-oxoacetyl)cyclohexyl)-1-((R)-3-cyclohexyl-2-(4-(methylsulfonyl)benzamido)propanoyl)-4-(4-((methylsulfonyl)methyl)-1H-1,2,3-triazol-1-yl)pyrrolidine-2-carboxamide | 761.91 | 762 (M + 1)⊕ |

Example 22: N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide
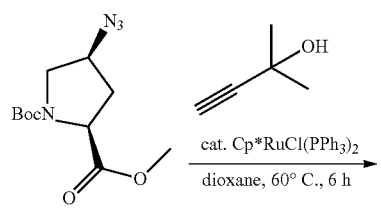
(step 2, intermediate L)
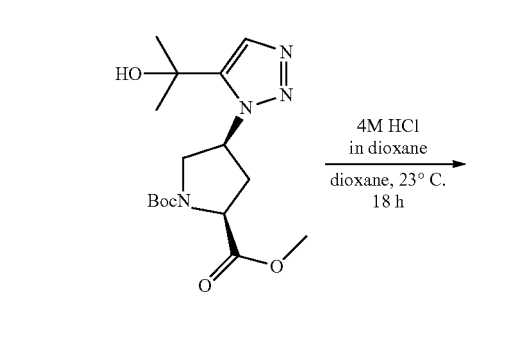
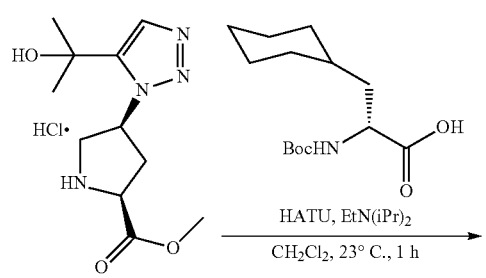
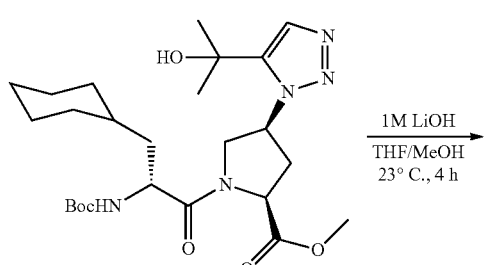
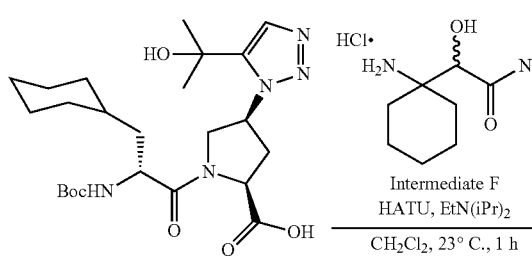
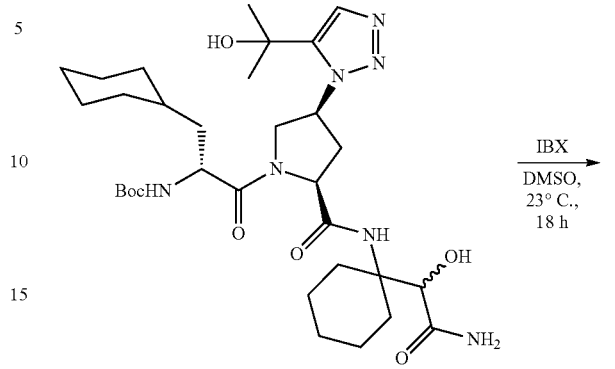
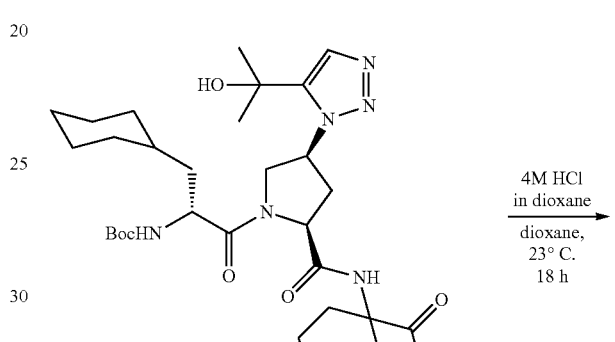
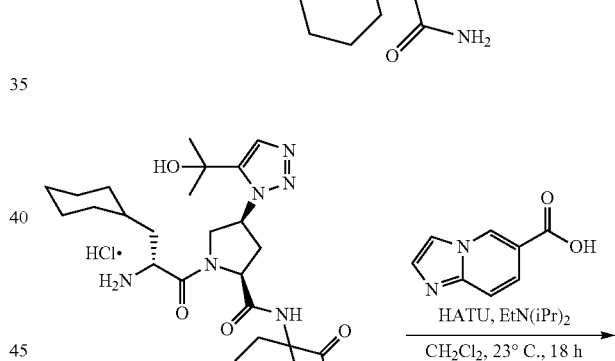
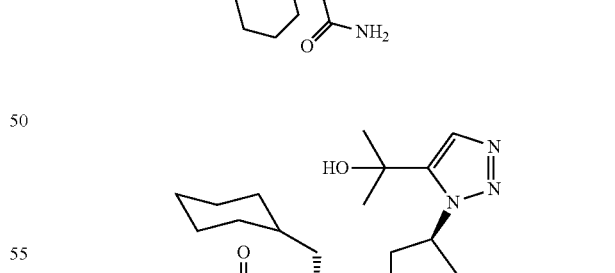
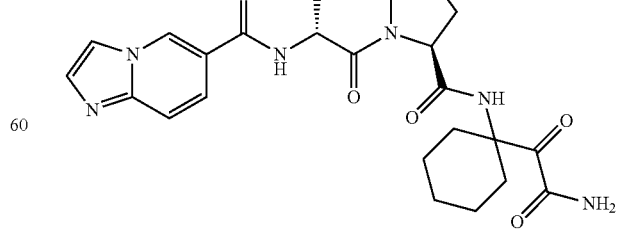
Example 22

Step 1: Preparation of 1-(tert-butyl) 2-methyl (2S,4S)-4-(5-(2-hydroxypropan-2-yl)-1H-1,2,3-triazol-1-yl)pyrrolidine-1,2-dicarboxylate Prepared in a similar manner as methyl (2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxylate (step 1, intermediate M) using (2S,4S)-1-tert-butyl 2-methyl 4-azidopyrrolidine-1,2-dicarboxylate to provide the title compound.

Step 2: Preparation of methyl (2S,4S)-4-(5-(2-hydroxypropan-2-yl)-1H-1,2,3-triazol-1-yl) pyrrolidine-2-carboxylate hydrochloride Prepared in the same manner as 2-(1-aminocyclobutyl)-2-hydroxyacetamide hydrochloride (step 4, intermediate A) using 1-(tert-butyl) 2-methyl (2S,4S)-4-(5-(2-hydroxypropan-2-yl)-1H-1,2,3-triazol-1-yl)pyrrolidine-1,2-dicarboxylate to provide the title compound.

Step 3: Preparation of methyl (2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using methyl (2S,4S)-4-(5-(2-hydroxypropan-2-yl)-1H-1,2,3-triazol-1-yl) pyrrolidine-2-carboxylate hydrochloride and (R)-2-((tert-butoxycarbonyl)amino)-3-cyclohexylpropanoic acid to provide the title compound.

Step 4: Preparation of (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid Prepared in a similar manner as (2S,4S)-1-((R)-2-(2-naphthamido)-3-cyclohexylpropanoyl)-4-azido pyrrolidine-2-carboxylic acid (step 7, intermediate L) using (2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxylate to provide the title compound.

Step 5: Preparation of tert-butyl ((2R)-1-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate F to provide the title compound.

Step 6: Preparation of tert-butyl ((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl) pyrrolidin-1-yl)-3-cyclohexyl-1-oxopropan-2-yl) carbamate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl ((2R)-1-((2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 7: Preparation of (2S,4S)—N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl ((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamate.

Step 8: Preparation of N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and imidazo[1,2-a]pyridine-6-carboxylic acid to provide the title compound. MS (ESI+) 690 (M+1)$^{\oplus}$ The following compounds, examples 23, 24, 25, 26, 27 and 28, were prepared in a similar manner as example 22 using commercially available acids.

| Example | Structure | MW | MS (ESI+) |
|---|---|---|---|
| 23 | 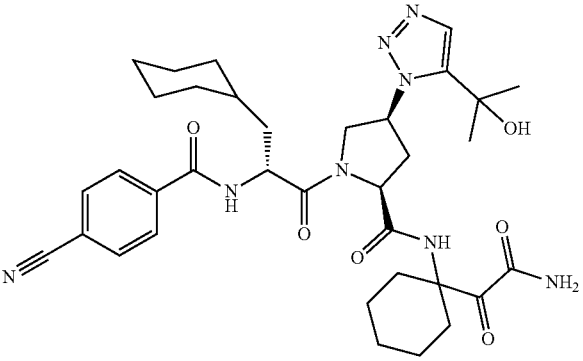<br>(2S,4S)-N-(1-(2-amino-2-oxoacetyl)cyclohexyl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide | 674.79 | 676 (M + 1)⊕ |
| 24 | 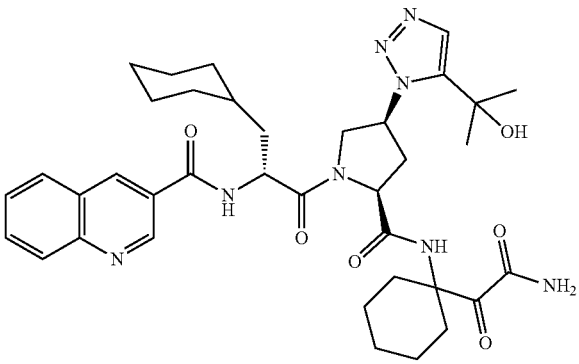<br>N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide | 746.86 | 745 (M−1)⊖ |
| 25 | 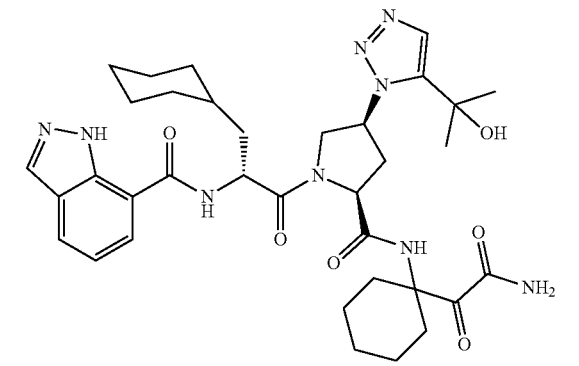<br>N-((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide | 689.82 | 690 (M + 1)⊕ |

-continued

| Example | Structure | MW | MS (ESI+) |
|---|---|---|---|
| 26 | (2S,4S)-N-(1-(2-amino-2-oxoacetyl)cyclohexyl)-1-((R)-3-cyclohexyl-2-(4-((2-methoxyethyl)sulfonyl)benzamido)propanoyl)-4-(5-(2-hydroxypropan-2-yl)-1H-1,2,3-triazol-1-yl)pyrrolidine-2-carboxamide | 771.92 | 772 (M + 1)⊕ |
| 27 | (2S,4S)-N-(1-(2-amino-2-oxoacetyl)cyclohexyl)-1-((R)-3-cyclohexyl-2-(4-((difluoromethyl)sulfonyl)benzamido)propanoyl)-4-(5-(2-hydroxypropan-2-yl)-1H-1,2,3-triazol-1-yl)pyrrolidine-2-carboxamide | 763.85 | 765 (M + 1)⊕ |
| 28 | (2S,4S)-N-(1-(2-amino-2-oxoacetyl)cyclohexyl)-1-((R)-2-(4-((2-amino-2-oxoethyl)sulfonyl)benzamido)-3-cyclohexylpropanoyl)-4-(5-(2-hydroxypropan-2-yl)-1H-1,2,3-triazol-1-yl)pyrrolidine-2-carboxamide | 770.90 | 772 (M + 1)⊕ |

Example 29: N²—((R)-1-((2S,4S)-2-((1-(2-amino-2-oxoacetyl)cyclohexyl)carbamoyl)-4-(5-(2-hydroxy-propan-2-yl)-1H-1,2,3-triazol-1-yl)pyrrolidin-1-yl)-3-cyclohexyl-1-oxopropan-2-yl)-N⁶-(2,5,8,11-tetraoxatridecan-13-yl)naphthalene-2,6-dicarboxamide
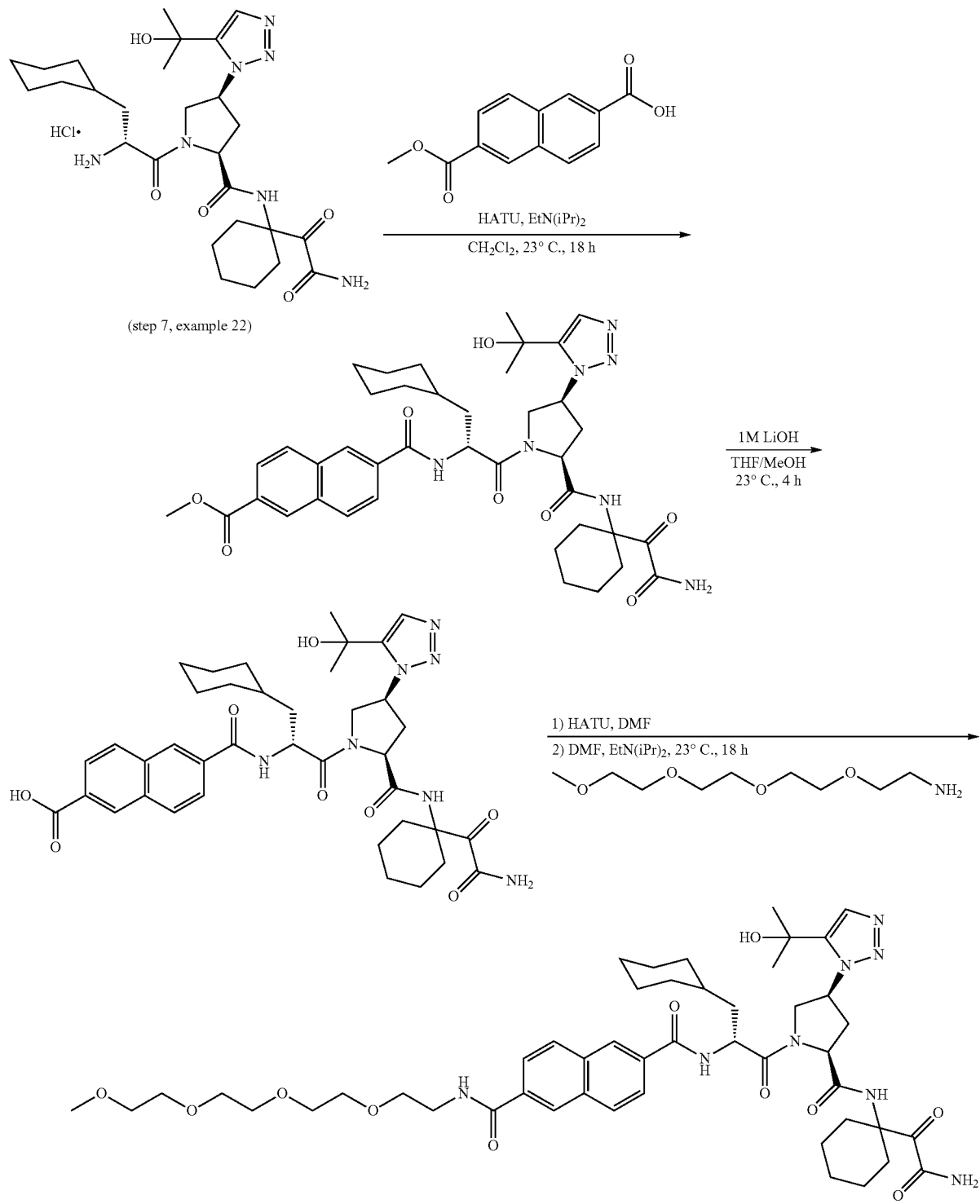
Example 29

Step 1: Preparation of methyl 6-(((R)-1-((2S,4S)-2-((1-(2-amino-2-oxoacetyl)cyclohexyl) carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-2-oxoacetyl)cyclohexyl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 6-(methoxycarbonyl)-2-naphthoic acid to provide the title compound.

Step 2: Preparation of 6-(((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 6-(((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoate to provide the title compound.

Step 3: Preparation of $N^2$—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide Into a 4 mL sample vial equipped with a magnetic stir bar was added 6-(((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamoyl)-2-naphthoic acid (42.6 mg, 0.057 mmol, 1.0 equiv), HATU (25 mg, 0.066 mmol, 1.2 equiv) and DMF (300 µL). The resulting solution was stirred at room temperature for 10 min. A DMF (200 µL) solution of 2,5,8,11-tetraoxatridecan-13-amine (24 mg, 0.114 mmol, 2.0 equiv) was added. Another 200 µL DMF was used to wash and transfer the remaining 2,5,8,11-tetraoxatridecan-13-amine. $EtNiPr_2$ (25 µL, 0.143 mmol, 2.5 equiv) was then added and the mixture was stirred at room temperature for 18 h. LCMS analysis revealed product formation. The reaction mixture was loaded onto a C18 5 g pre-cartridge and dried. Purification was conducted by reverse phase column chromatography on the ISCO Rf (30 g C18 Gold column) eluting with 100:0 to 0:100 $H_2O$:MeCN+0.1% HCOOH as a gradient over 30 min. The desired product was isolated and further dried under vacuum to afford the title product. MS (ESI+) 933 (M+1)$^⊕$ The following compound, example 30, was prepared in a similar manner as example 29 using 2,5,8,11,14,17,20,23,26,29,32,35,38,41,44,47,50,53,56,59,62,65,68,71-tetracosaoxatriheptacontan-73-amine in step 3.

| Example | Structure | MW | MS (ESI+) |
|---|---|---|---|
| 30 | 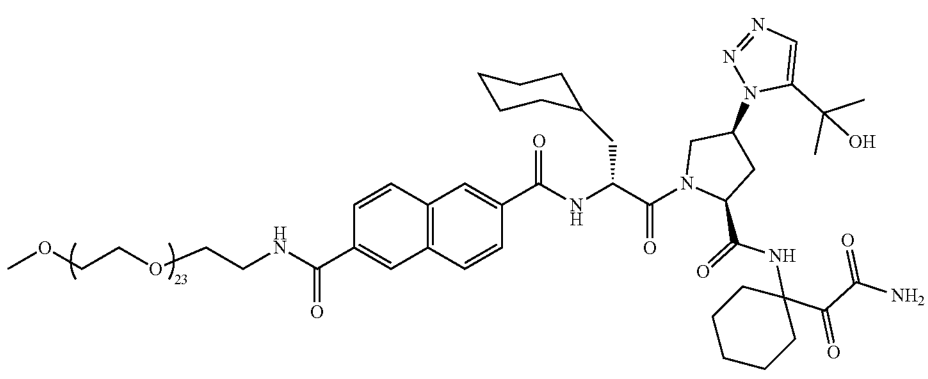 | 1813.0 | 908 [(M + 2)/2]$^⊕$ |

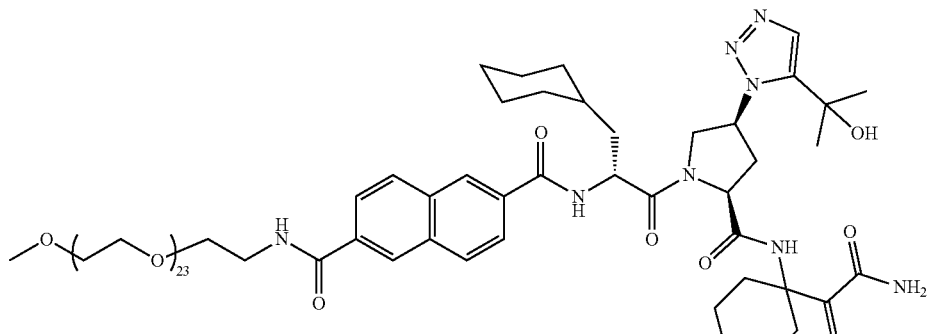

$N^2$-((R)-1-((2S,4S)-2-((1-(2-amino-2-oxoacetyl)cyclohexyl)carbamoyl)-4-(5-(2-hydroxypropan-2-yl)-1H-1,2,3-trizaol-1-yl)pyrrolidin-1-yl)-3-cyclohexyl-1-oxopropan-2-yl)-$N^6$-(tetracosaoxatriheptacontan-73-yl)naphthalene-2,6-dicarboxamide Example 31: (2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl)pyrrolidine-2-carboxamide
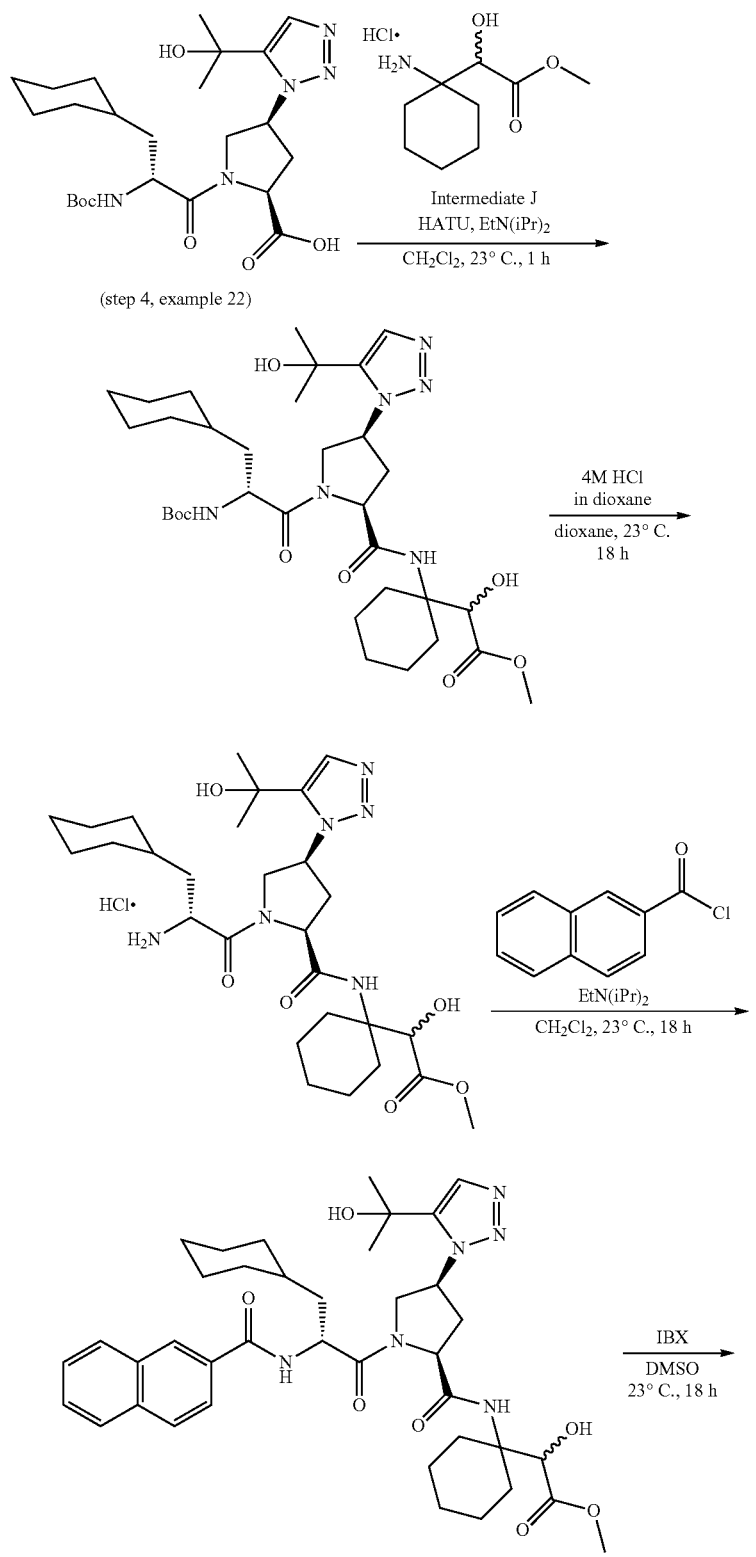

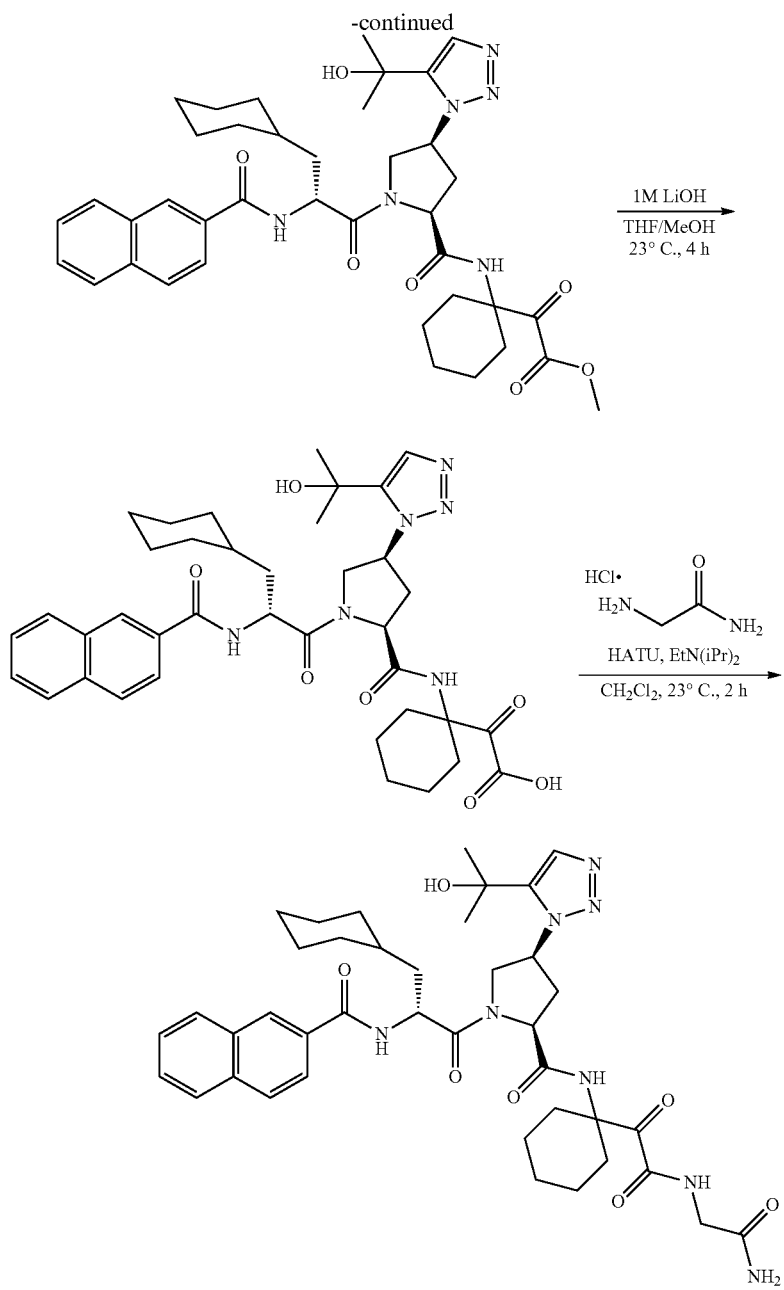

Example 31

Step 1: Preparation of methyl 2-(1-((2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxamido)cyclohexyl)-2-hydroxyacetate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate J to provide the title compound.

Step 2: Preparation of methyl 2-(1-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate hydrochloride Prepared in the same manner as 2-(1-aminocyclobutyl)-2-hydroxyacetamide hydrochloride (step 4, intermediate A) using methyl 2-(1-((2S,4S)-1-((R)-2-((tert-butoxycarbonyl)amino)-3-cyclohexyl propanoyl)-4-(5-(2-hydroxypropan-2-yl)-1H-1,2,3-triazol-1-yl)pyrrolidine-2-carboxamido)cyclohexyl)-2-hydroxyacetate.

Step 3: Preparation of methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate Prepared in a similar manner as methyl (2S,4S)-1-((R)-2-(2-naphthamido)-3-cyclohexylpropanoyl)-4-azidopyrrolidine-2-carboxylate (step 6, intermediate L) using methyl 2-(1-((2S,4S)-1-((R)-2-amino-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate hydrochloride and 2-naphthoyl chloride to provide the title compound.

Step 4: Preparation of methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetate Prepared in a similar manner as tert-butyl ((R)-1-((2S,3R,4R)-2-((1-(2-amino-2-oxoacetyl)cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-hydroxyacetate to provide the title compound.

Step 5: Preparation of 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetic acid Prepared in a similar manner as (2S,4S)-1-((R)-2-(2-naphthamido)-3-cyclohexylpropanoyl)-4-azido pyrrolidine-2-carboxylic acid (step 7, intermediate L) using methyl 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetate to provide the title compound.

Step 6: Preparation of (2S,4S)-1-((R)-2-(2-naphthamido)-3-cyclohexylpropanoyl)-N-(1-(2-((2-amino-2-oxoethyl)amino)-2-oxoacetyl)cyclohexyl)-4-(5-(2-hydroxypropan-2-yl)-1H-1,2,3-triazol-1-yl) pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using 2-(1-((2S,4S)-1-((R)-2-(2-naphthamido)-3-cyclohexylpropanoyl)-4-(5-(2-hydroxypropan-2-yl)-1H-1,2,3-triazol-1-yl)pyrrolidine-2-carboxamido)cyclohexyl)-2-oxoacetic acid and 2-aminoacetamide hydrochloride to provide the title compound. MS (ESI+) 758 (M+1)$^{\oplus}$ The following compounds, examples 32, 33 and 34, were prepared in a similar manner as example 31 using commercially available amines in step 6.

| Example | Structure | MW | MS (ESI+) |
|---|---|---|---|
| 32 | 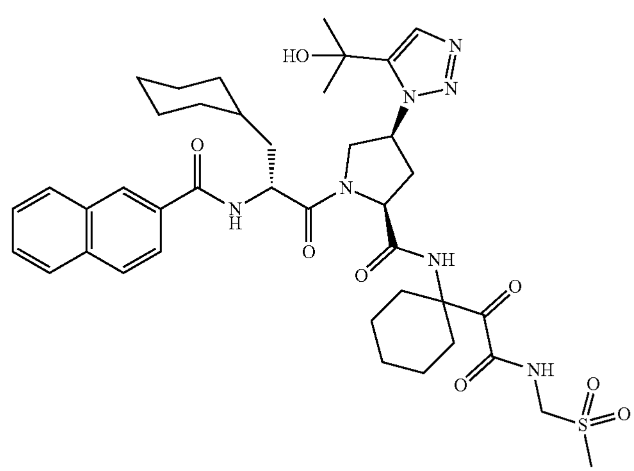 | 805.98 | 806 (M + 1)$^{\oplus}$ |

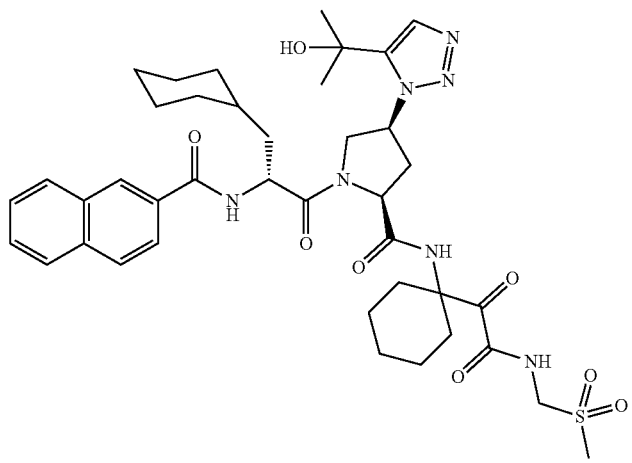

(2S,4S)-1-((R)-2-(2-naphthamido)-3-cyclohexylpropanoyl)-4-(5-(2-hydroxypropan-2-yl)-1H-1,2,3-trizaol-1-yl)-N-(1-(2-(((methylsulfonyl)methyl)amino)-2-oxacetyl)cyclohexyl)pyrrolidine-2-carboxamide

| Example | Structure | MW | MS (ESI+) |
|---|---|---|---|
| 33 | 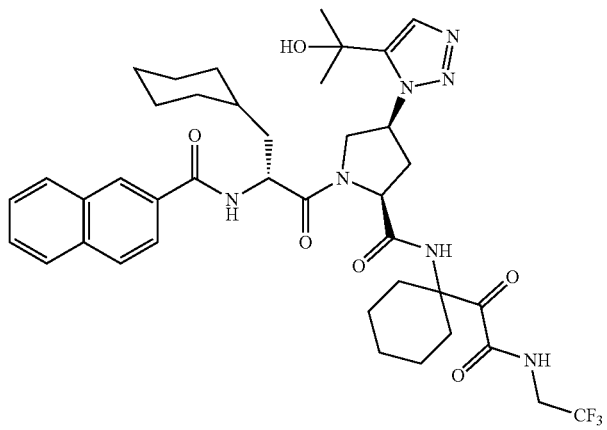<br>(2S,4S)-1-((R)-2-(2-naphthamido)-3-cyclohexylpropanoyl)-4-(5-(2-hydroxypropan-2-yl)-1H-1,2,3-trizaol-1-yl)-N-(1-(2-oxo-2-((2,2,2-trifluoroethyl)amino)acetyl)cyclohexyl)pyrrolidine-2-carboxamide | 781.86 | 783 (M + 1)$^\oplus$ |
| 34 | 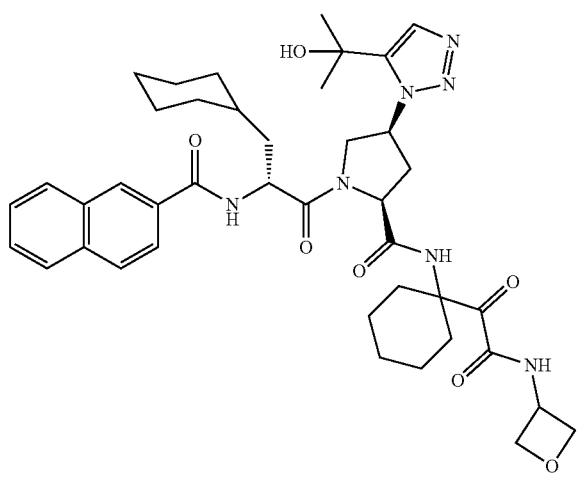<br>(2S,4S)-1-((R)-2-(2-naphthamido)-3-cyclohexylpropanoyl)-4-(5-(2-hydroxypropan-2-yl)-1H-1,2,3-trizaol-1-yl)-N-(1-(2-oxetan-3-ylamino)-2-oxoacetyl)cyclohexyl)pyrrolidine-2-carboxamide | 755.90 | 757 (M + 1)$^\oplus$ |

Example 35: (2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide
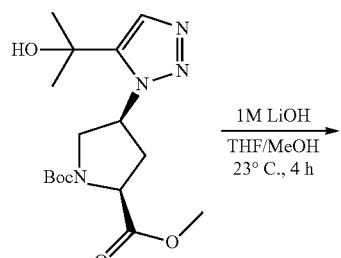
(step 1, example 22)
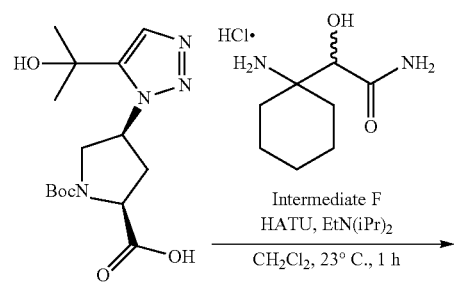
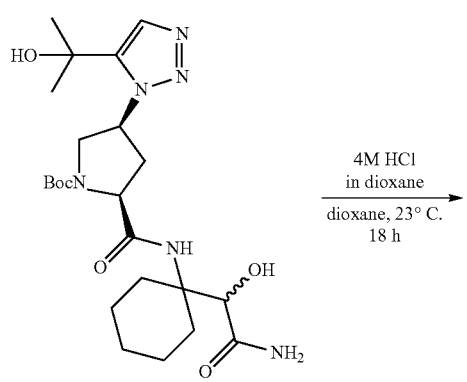
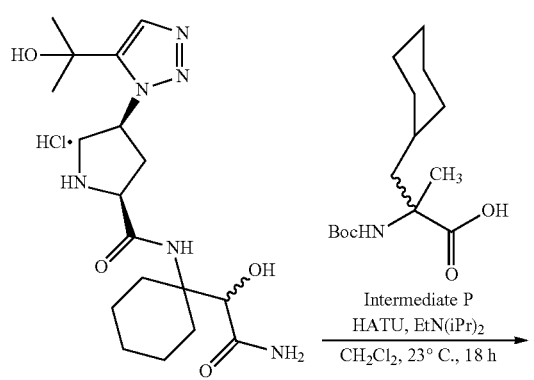
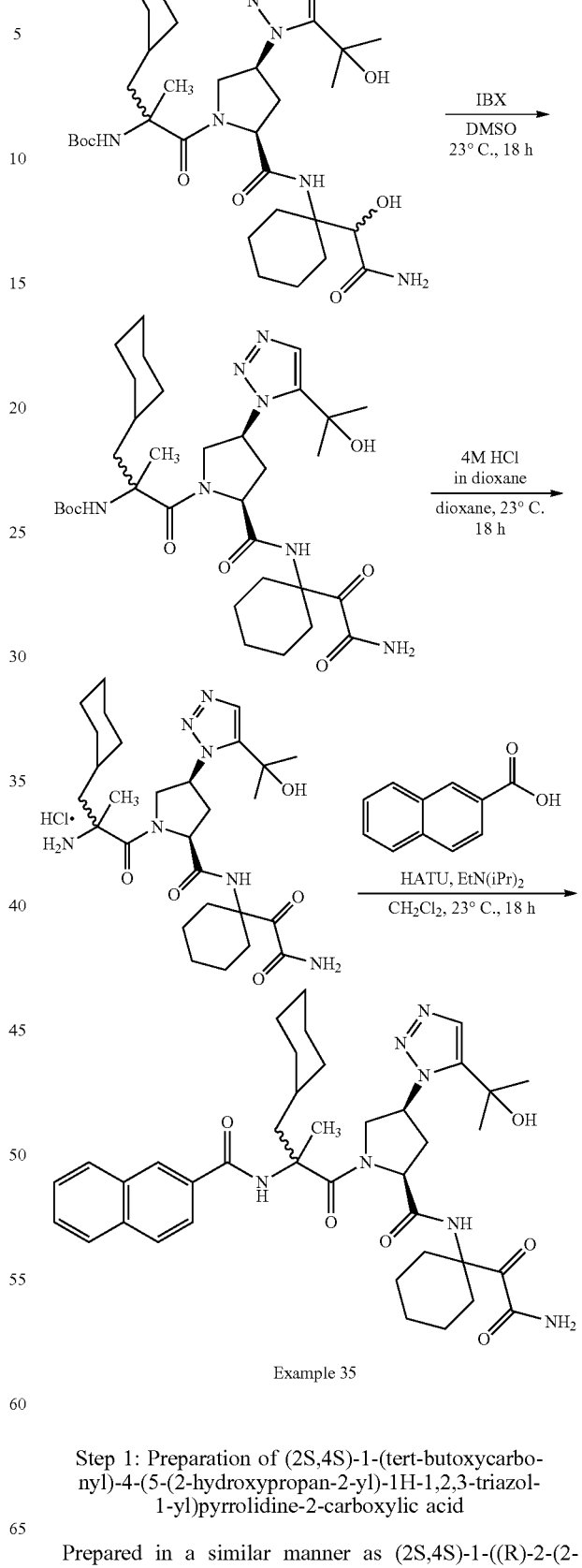
Example 35
Step 1: Preparation of (2S,4S)-1-(tert-butoxycarbonyl)-4-(5-(2-hydroxypropan-2-yl)-1H-1,2,3-triazol-1-yl)pyrrolidine-2-carboxylic acid
Prepared in a similar manner as (2S,4S)-1-((R)-2-(2-naphthamido)-3-cyclohexylpropanoyl)-4-azido pyrrolidine- 2-carboxylic acid (step 7, intermediate L) using (2S,4S)-1-tert-butyl 2-methyl 4-(5-(2-hydroxypropan-2-yl)-1H-1,2,3-triazol-1-yl)pyrrolidine-1,2-dicarboxylate to provide the title compound.

Step 2: Preparation of tert-butyl (2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidine-1-carboxylate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-(tert-butoxycarbonyl)-4-(5-(2-hydroxypropan-2-yl)-1H-1,2,3-triazol-1-yl)pyrrolidine-2-carboxylic acid and intermediate F to provide the title compound.

Step 3: Preparation of (2S,4S)—N-(1-(2-amino-1-hydroxy-2-oxoethyl)cyclohexyl)-4-(5-(2-hydroxy propan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl (2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidine-1-carboxylate to provide the title compound.

Step 4: Preparation of tert-butyl (1-((2S,4S)-2-((1-(2-amino-1-hydroxy-2-oxoethyl) cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-1-hydroxy-2-oxoethyl)cyclohexyl)-4-(5-(2-hydroxy propan-2-yl)-1H-1,2,3-triazol-1-yl)pyrrolidine-2-carboxamide hydrochloride and intermediate P to provide the title compound.

Step 5: Preparation of tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl (1-((2S,4S)-2-((1-(2-amino-1-hydroxy-2-oxoethyl) cyclohexyl) carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate to provide the title compound.

Step 6: Preparation of (2S,4S)—N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-2-methyl-1-oxopropan-2-yl)carbamate to provide the title product.

Step 7: Preparation of (2S,4S)-1-(2-(2-naphthamido)-3-cyclohexyl-2-methylpropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+) 736 (M+23)$^{\oplus}$ Example 36: (2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide

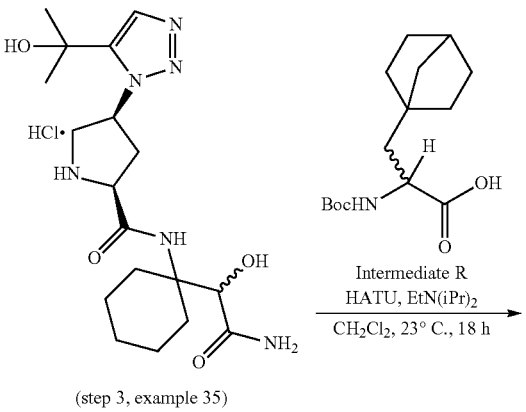

(step 3, example 35)

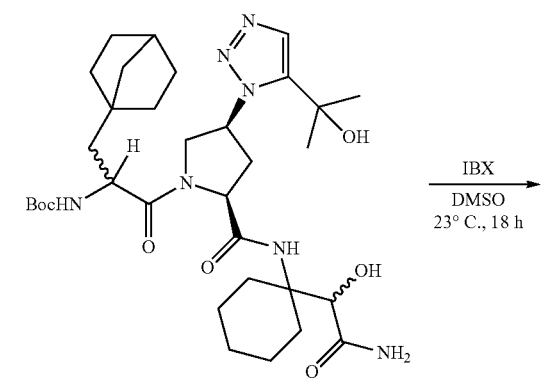

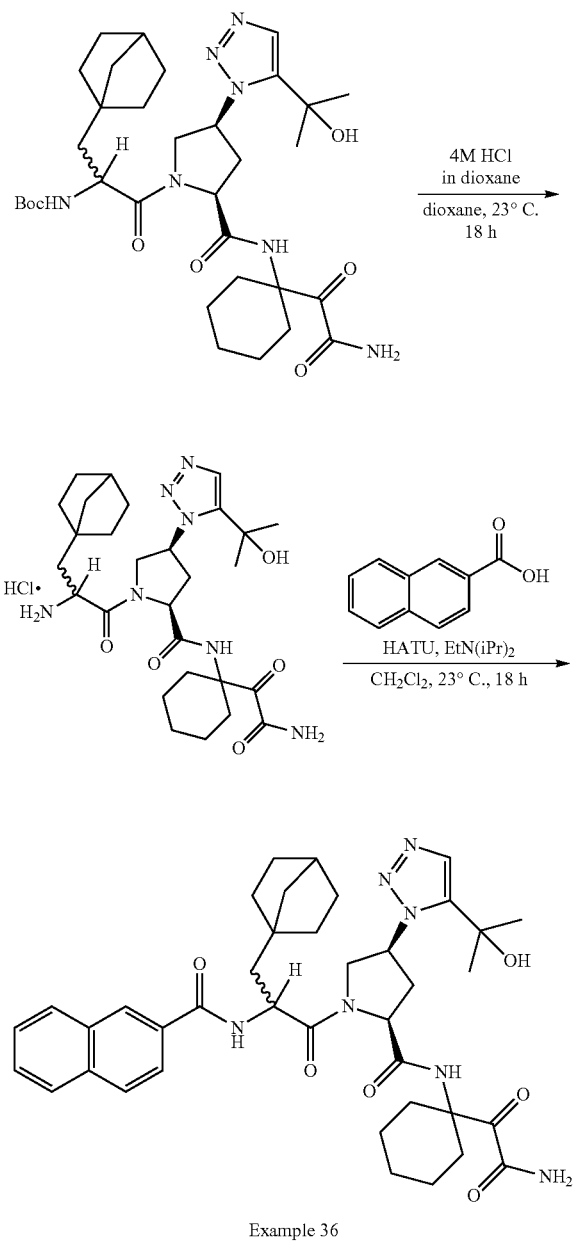

Example 36

Step 1: Preparation of tert-butyl (1-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-1-hydroxy-2-oxoethyl)cyclohexyl)-4-(5-(2-hydroxy propan-2-yl)-1H-1,2,3-triazol-1-yl)pyrrolidine-2-carboxamide hydrochloride (step 4, example 35) and intermediate R to provide the title compound.

Step 2: Preparation of tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl (1-((2S,4S)-2-((1-(2-amino-1-hydroxy-2-oxoethyl)cyclohexyl) carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate to provide the title compound.

Step 3: Preparation of (2S,4S)—N-(1-(2-amino-2-oxoacetyl)cyclohexyl)-1-(2-amino-3-(bicyclo[2.2.1]heptan-1-yl)propanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl (1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-(bicyclo[2.2.1]heptan-1-yl)-1-oxopropan-2-yl)carbamate to provide the title product.

Step 4: Preparation of (2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-2-oxoacetyl)cyclohexyl)-1-(2-amino-3-(bicyclo[2.2.1]heptan-1-yl)propanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+) 728 (M+1)⊕; $^1$H NMR (300 MHz, CDCl$_3$) δ 8.50-8.25 (m, 1H), 8.23-7.77 (m, 5H), 7.77-7.47 (m, 3H), 7.43-7.30 (m, 1H), 7.25-6.95 (m, 1H), 6.90-6.30 (m, 1H), 6.06 (br s, 1H), 5.80-5.50 (m, 1H), 5.25-4.75 (m, 2H), 4.75-4.15 (m, 2H), 2.72-2.25 (m, 7H), 2.25-1.94 (m, 3H), 1.94-1.02 (m, 19H), 1.02-0.65 (m, 2H).

The following compound, example 37, was prepared in a similar manner as example 36, from intermediate Q in step 1.

| Example | Structure | MW | MS (ESI+) |
|---|---|---|---|
| 37 | 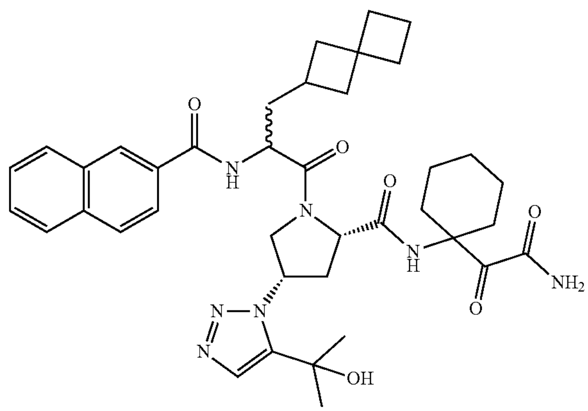 | 711.85 | 712 (M + 1)⊕ |

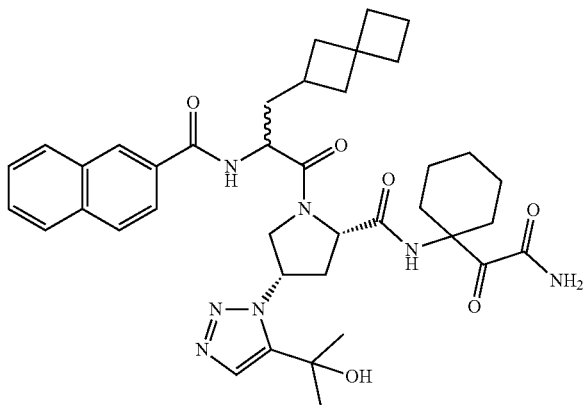

(2S,4S)-1-(2-(2-naphthamido)-3-(spiro[3.3]heptan-2-yl)propanoyl)-N-(1-(2-amino-2-oxoacetyl)cyclohexyl)-4-(5-(2-hydroxpropan-2-yl)-1H-1,2,3-trizaol-1-yl)pyrrolidine-2-carboxamide Example 38: (2S,4S)—N-(1-(2-amino-2-oxoacetyl)cyclohexyl)-1-(3-cyclohexyl-2-methyl-2-(4-(methylsulfonyl)benzamido)propanoyl)-4-(5-(2-hydroxypropan-2-yl)-1H-1,2,3-triazol-1-yl)pyrrolidine-2-carboxamide

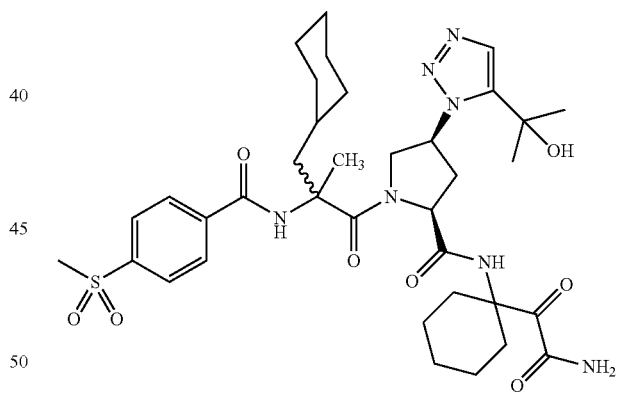

Example 38

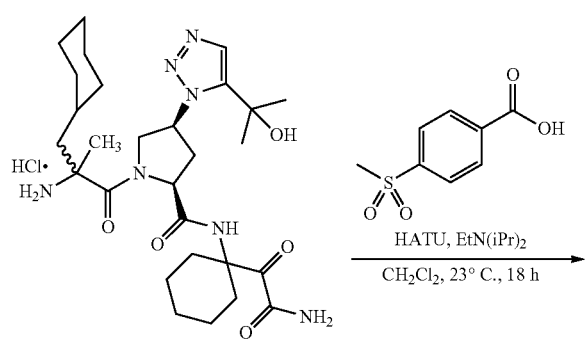

Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-2-oxoacetyl)cyclohexyl)-1-(2-amino-3-cyclohexyl-2-methylpropanoyl)-4-(5-(2-hydroxypropan-2-yl)-1H-1,2,3-triazol-1-yl)pyrrolidine-2-carboxamide hydrochloride and 4-(methylsulfonyl)benzoic acid to provide the title compound. MS (ESI+) 742 (M+1)⊕

The following compounds, examples 39 and 40, were prepared in a similar manner as example 38 using intermediate Q and intermediate R, respectively.

| Example | Structure | MW | MS (ESI+) |
|---|---|---|---|
| 39 | (2S,4S)-N-(1-(2-amino-2-oxoacetyl)cyclohexyl)-4-(5-(2-hydroxypropan-2-yl)-1H-1,2,3-triazol-1-yl)-1-(2-(4-(methylsulfonyl)benzamido)-3-(spiro[3.3]heptan-2-yl)propanoyl)pyrrolidine-2-carboxamide | 739.88 | 740 (M + 1)⊕ |
| 40 | (2S,4S)-N-(1-(2-amino-2-oxoacetyl)cyclohexyl)-1-(3-(bicyclo[2.2.1]heptan-1-yl)-2-(4-(methylsulfonyl)benzamido)propanoyl)-4-(5-(2-hydroxypropan-2-yl)-1H-1,2,3-trizaol-1-yl)pyrrolidine-2-carboxamide | 739.88 | 740 (M + 1)⊕ |

Example 41: benzyl ((R)-2-(2-naphthamido)-3-((2S,4S)-2-((1-(2-amino-2-oxoacetyl)cyclohexyl) carbamoyl)-4-(5-(2-hydroxypropan-2-yl)-1H-1,2,3-triazol-1-yl)pyrrolidin-1-yl)-3-oxopropyl)carbamate -continued

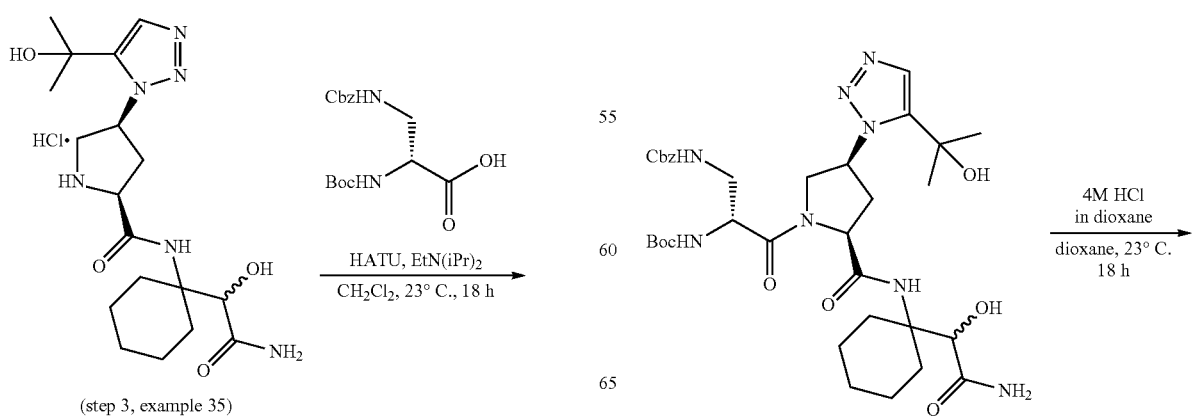

125
-continued

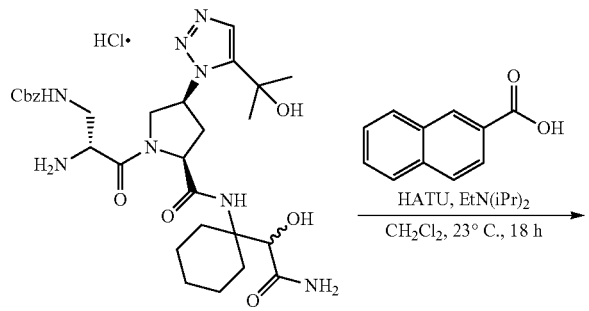

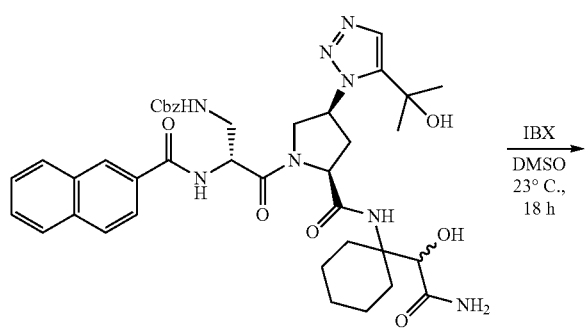

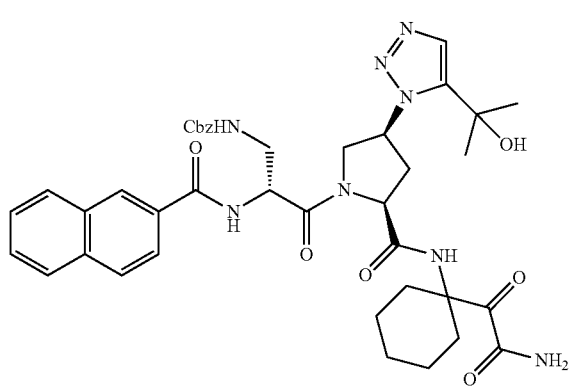

Example 41

Step 1: Preparation of benzyl tert-butyl ((2R)-3-((2S,4S)-2-((1-(2-amino-1-hydroxy-2-oxoethyl) cyclohexyl)carbamoyl)-4-(5-(2-hydroxypropan-2-yl)-1H-1,2,3-triazol-1-yl)pyrrolidin-1-yl)-3-oxopropane-1,2-diyl)dicarbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride and and (R)-3-(((benzyloxy)carbonyl)amino)-2-((tert-butoxycarbonyl)amino)propanoic acid to provide the title compound.

Step 2: Preparation of benzyl ((2R)-2-amino-3-((2S,4S)-2-((1-(2-amino-1-hydroxy-2-oxoethyl) cyclohexyl)carbamoyl)-4-(5-(2-hydroxypropan-2-yl)-1H-1,2,3-triazol-1-yl)pyrrolidin-1-yl)-3-oxopropyl) carbamate hydrochloride Prepared in the same manner as 2-(1-aminocyclobutyl)-2-hydroxyacetamide hydrochloride (step 4, intermediate A) using benzyl tert-butyl ((2R)-3-((2S,4S)-2-((1-(2-amino-1-hydroxy-2-oxoethyl) cyclohexyl)carbamoyl)-4-(5-(2-hydroxypropan-2-yl)-1H-1,2,3-triazol-1-yl)pyrrolidin-1-yl)-3-oxopropane-1,2-diyl)dicarbamate to provide the title compound.

Step 3: Preparation of benzyl ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using benzyl ((2R)-2-amino-3-((2S,4S)-2-((1-(2-amino-1-hydroxy-2-oxoethyl) cyclohexyl)carbamoyl)-4-(5-(2-hydroxypropan-2-yl)-1H-1,2,3-triazol-1-yl)pyrrolidin-1-yl)-3-oxopropyl) carbamate hydrochloride and 2-naphthoic acid to provide the title compound.

Step 4: Preparation of benzyl ((R)-2-(2-naphthamido)-3-((2S,4S)-2-((1-(2-amino-2-oxoacetyl) cyclohexyl)carbamoyl)-4-(5-(2-hydroxypropan-2-yl)-1H-1,2,3-triazol-1-yl)pyrrolidin-1-yl)-3-oxopropyl) carbamate Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using benzyl ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl) carbamate to provide the title compound. MS (ESI+) 767 (M+1)⊕

Example 42: (2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide
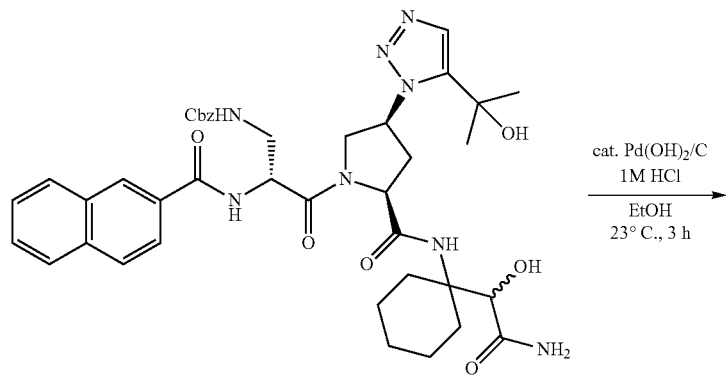
(step 3, example 41)
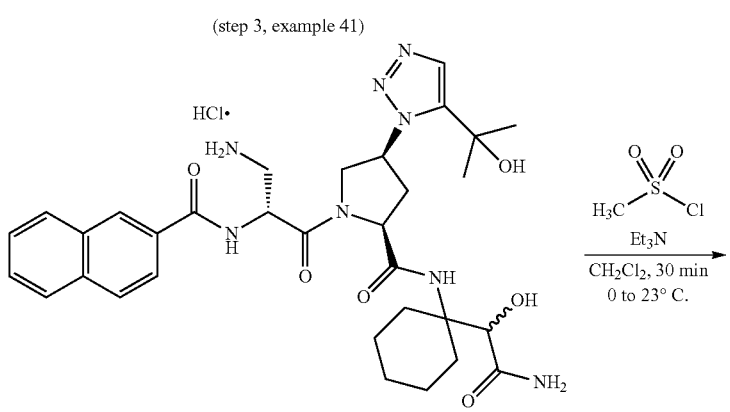
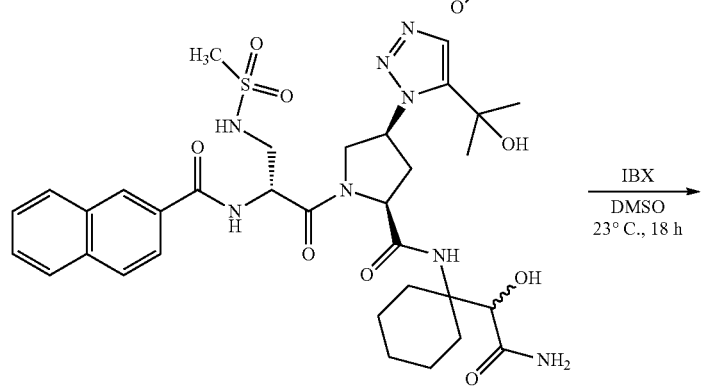
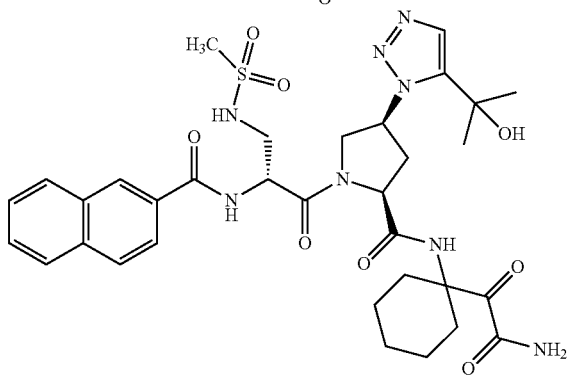
Example 42

Step 1: Preparation of (2S,4S)-1-((R)-2-(2-naph-thamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride Into a 25 mL round bottom flask equipped with a magnetic stir bar and under nitrogen was added ((2R)-2-(2-naphthamido)-3-((2S,4S)-2-((1-(2-amino-1-hydroxy-2-oxoethyl)cyclohexyl)carbamoyl)-4-(5-(2-hydroxypropan-2-yl)-1H-1,2,3-triazol-1-yl)pyrrolidin-1-yl)-3-oxopropyl) carbamate (114 mg, 0.15 mmol, 1.0 equiv), EtOH (2.5 mL) and aq. HCl (1 M, 190 µL, 0.19 mmol, 1.3 equiv). The solution was sparged with nitrogen for 30 min. Pd(OH)$_2$/C (20% wt., 20 mg) was added and the nitrogen source was then replaced with a hydrogen balloon. The reaction mixture was sparged with 1 balloon of hydrogen, followed by removing the bubbler. The reaction mixture was stirred at room temperature for 3 h under an atmosphere of hydrogen. LCMS analysis revealed completion of reaction. The reaction mixture was filtered through a pad of celite on a plastic sintered funnel and washed with DCM (3×5 mL). The clear filtrate was concentrated under reduced pressure and used directly in the next step without further purification.

Step 2: Preparation of (2S,4S)-1-((R)-2-(2-naph-thamido)-3-(methylsulfonamido)propanoyl)-N-(1-(2-amino-1-hydroxy-2-oxoethyl)cyclohexyl)-4-(5-(2-hydroxypropan-2-yl)-1H-1,2,3-triazol-1-yl) pyrrolidine-2-carboxamide Into a 4 mL sample vial equipped with magnetic stir bar and under nitrogen was added (2S,4S)-1-((R)-2-(2-naph-thamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride (24.2 mg, 0.036 mmol, 1.0 equiv), methylsulfonyl chloride (2.8 µL, 0.036 mmol, 1.0 equiv) and DCM (360 µL). The suspension was cooled to 0° C. in an ice bath and then treated with Et$_3$N (16.5 µL, 0.120 mmol, 3.3 equiv). The mixture was warmed up to room temperature and stirred for 30 min. LCMS analysis revealed the formation of product. The reaction mixture was loaded onto a C18 5 g pre-cartridge and dried. Purification was conducted by reverse phase column chromatography on the ISCO Rf (15.5 g C18 Gold column) eluting with 100:0 to 30:70 H$_2$O:MeCN+ 0.1% HCOOH as a gradient over 14 min. The desired product was isolated and further dried under vacuum to afford the title product.

Step 3: Preparation of (2S,4S)-1-((R)-2-(2-naph-thamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-1-((R)-2-(2-naphthamido)-3-(methylsulfonamido)propanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide to provide the title compound. MS (ESI+) 711 (M+1)$^⊕$ Example 43: (2S,4S)-1-((R)-2-(2-naphthamido)-3-acetamidopropanoyl)-N-(1-(2-amino-2-oxoacetyl) cyclohexyl)-4-(5-(2-hydroxypropan-2-yl)-1H-1,2,3-triazol-1-yl)pyrrolidine-2-carboxamide

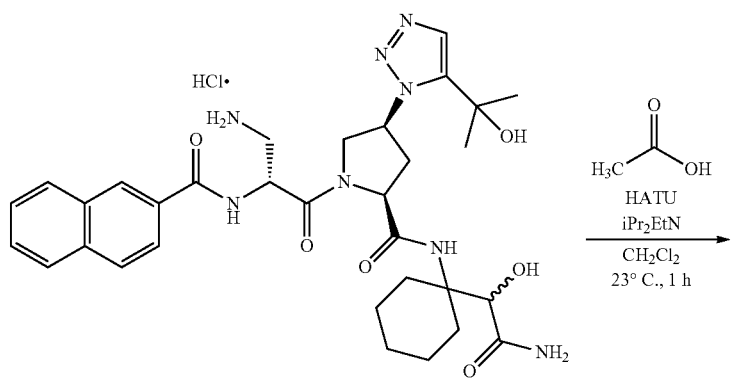

(step 1, example 42)

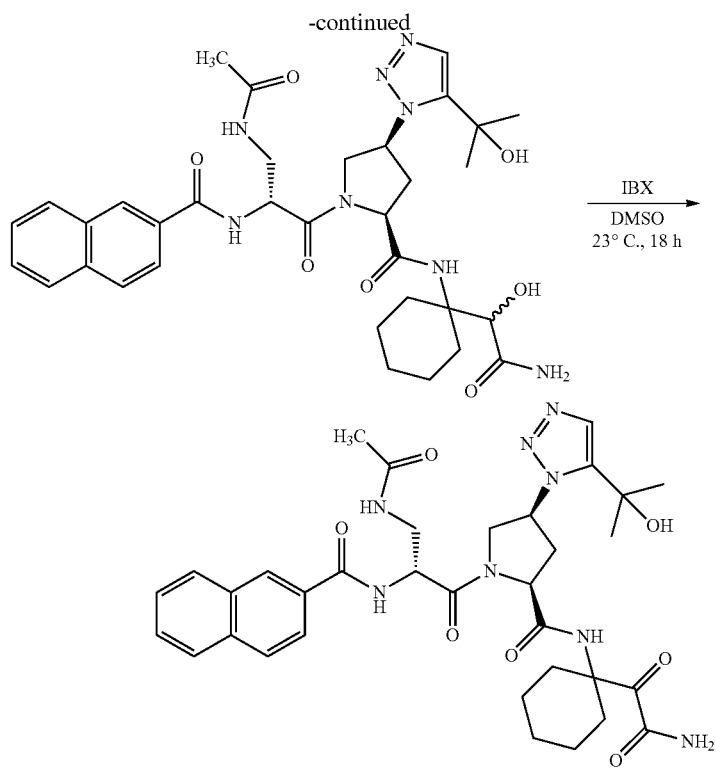

Example 43

Step 1: Preparation of (2S,4S)-1-((R)-2-(2-naphthamido)-3-acetamidopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-(2-naphthamido)-3-aminopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide hydrochloride and acetic acid to provide the title compound.

Step 2: Preparation of (2S,4S)-1-((R)-2-(2-naphthamido)-3-acetamidopropanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-1-((R)-2-(2-naphthamido)-3-acetamidopropanoyl)-N-(1-(2-amino-1-hydroxy-2-oxoethyl)cyclohexyl)-4-(5-(2-hydroxypropan-2-yl)-1H-1,2,3-triazol-1-yl)pyrrolidine-2-carboxamide to provide the title compound. MS (ESI+) 675 (M+1)$^{\oplus}$

Example 44: (2S,4S)-1-((R)-2-(2-naphthamido)-3-cyclohexylpropanoyl)-N-(2-(2-amino-2-oxoacetyl)spiro[3.3]heptan-2-yl)-4-(5-(2-hydroxypropan-2-yl)-1H-1,2,3-triazol-1-yl)pyrrolidine-2-carboxamide

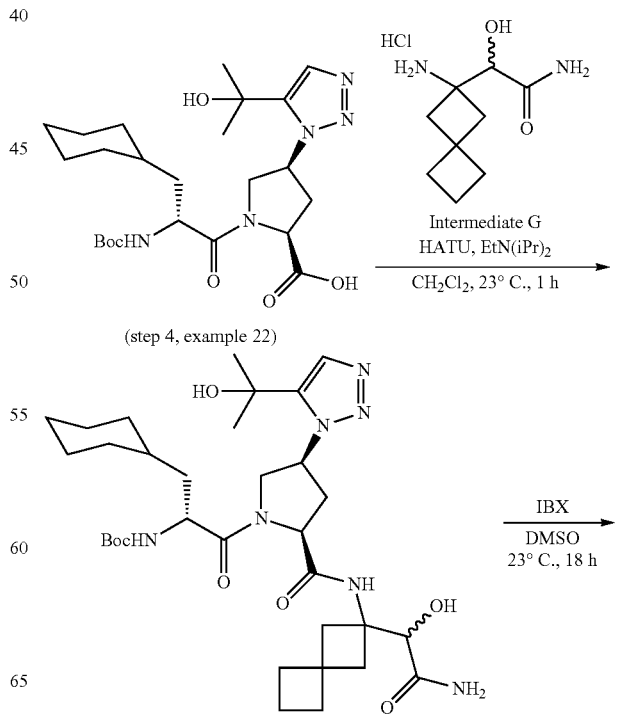

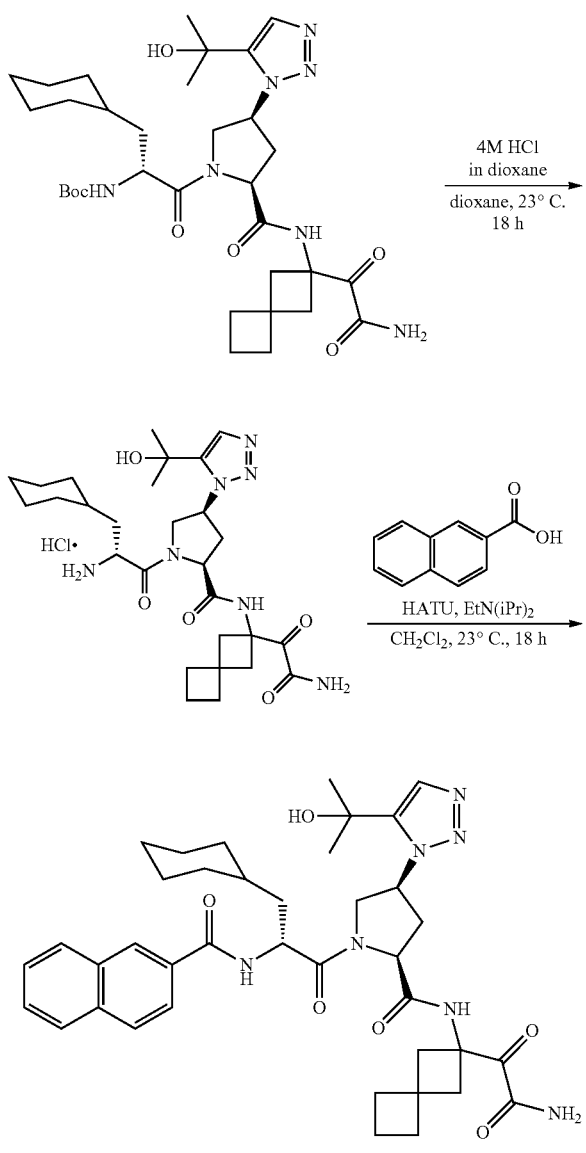

Example 44

Step 1: Preparation of tert-butyl ((2R)-1-((2S,4S)-2-((2-(2-amino-1-hydroxy-2-oxoethyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)-1-((R)-2-((tert-butoxycarbonyl)amino)-3-cyclohexylpropanoyl)-4-(5-(2-hydroxypropan-2-yl)-1H-1,2,3-triazol-1-yl)pyrrolidine-2-carboxylic acid and intermediate G to provide the title compound.

Step 2: Preparation of tert-butyl ((R)-1-((2S,4S)-2-((2-(2-amino-2-oxoacetyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using tert-butyl ((2R)-1-((2S,4S)-2-((2-(2-amino-1-hydroxy-2-oxoethyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 3: Preparation of (2S,4S)—N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride Prepared in the same manner as 2-(1-aminocyclobutyl)-2-hydroxyacetamide hydrochloride (step 4, intermediate A) using tert-butyl ((R)-1-((2S,4S)-2-((2-(2-amino-2-oxoacetyl)spiro[3.3]heptan-2-yl)carbamoyl)-4-(5-(2-hydroxypropan-2-yl)-1H-1,2,3-triazol-1-yl)pyrrolidin-1-yl)-3-cyclohexyl-1-oxopropan-2-yl)carbamate to provide the title compound.

Step 4: Preparation of (2S,4S)-1-((R)-2-(2-naphthamido)-3-cyclohexylpropanoyl)-N-(2-(2-amino-2-oxoacetyl)spiro[3.3]heptan-2-yl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 2-naphthoic acid to provide the title compound. MS (ESI+): 712 (M+1); $^1$H NMR (300 MHz, CD$_3$OD) δ 8.45 (s, 1H), 8.04-7.85 (m, 4H), 7.65-7.55 (m, 2H), 7.53 (s, 1H), 5.90-5.71 (m, 1H), 5.08-4.94 (m, 1H), 4.65-4.45 (m, 1H), 4.45-4.25 (m, 1H), 4.25-4.10 (m, 1H), 2.98-2.48 (m, 4H), 2.50-2.20 (m, 2H), 2.19-2.03 (m, 1H), 2.03-1.82 (m, 4H), 1.82-1.53 (m, 15H), 1.54-1.37 (m, 1H), 1.36-1.15 (m, 3H), 1.15-0.85 (s, 1H) ppm.

The following compound, example 45, was prepared in a similar manner as example 44 using intermediate H in step 1.

| Example | Structure | MW | MS (ESI+) |
|---|---|---|---|
| 45 | 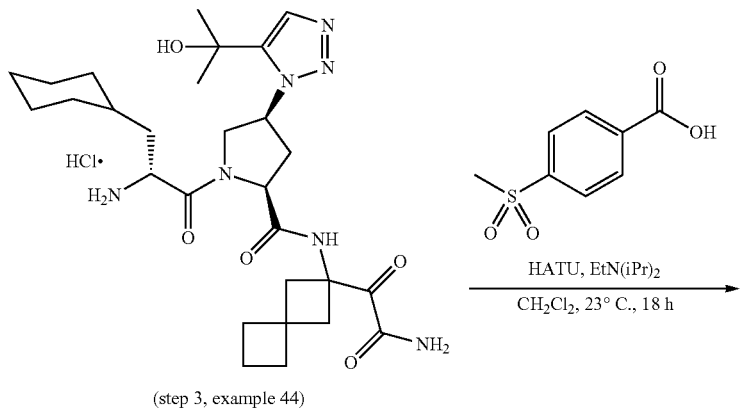 (2S,4S)-1-((R)-2-(2-naphthamido)-3-cyclohexylpropanoyl)-N-(1-(2-amino-2-oxoacetyl)-4,4-dimethylcyclohexyl)-4-(5-(2-hydroxypropan-2-yl)-1H-1,2,3-trizaol-1-yl)pyrrolidine-2-carboxamide | 727.89 | 728 (M + 1)⊕ |
Example 46: (2S,4S)—N-(2-(2-amino-2-oxoacetyl)spiro[3.3]heptan-2-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide
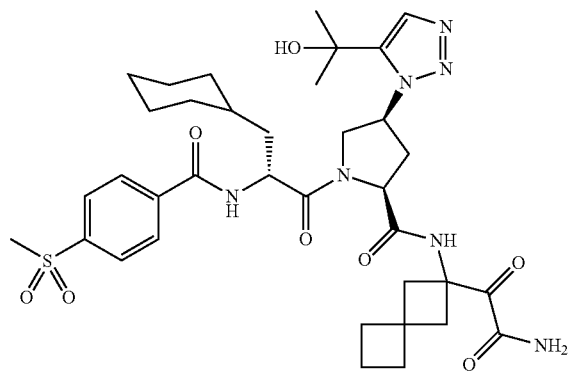
Example 46

Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using (2S,4S)—N-(2-(2-amino-2-oxoacetyl)spiro[3.3]heptan-2-yl)-1-((R)-2-amino-3-cyclohexylpropanoyl)-4-(5-(2-hydroxypropan-2-yl)-1H-1,2,3-triazol-1-yl)pyrrolidine-2-carboxamide hydrochloride and 4-(methylsulfonyl)benzoic acid to provide the title compound. MS (ESI+) 740 (M+1)⊕

The following compound, example 47, was prepared in a similar manner as example 46 using intermediate H.

| Example | Structure | MW | MS (ESI+) |
|---|---|---|---|
| 47 | (2S,4S)-N-(1-(2-amino-2-oxoacetyl)-4,4-dimethylcyclohexyl)-1-((R)-3-cyclohexyl-2-(4-(methylsulfonyl)benzamido)propanoyl)-4-(5-(2-hydroxypropan-2-yl)-1H-1,2,3-trizaol-1-yl)pyrrolidine-2-carboxamide | 755.92 | 756 (M + 1)⊕ |

Example 48: (2S,4S)-1-((R)-2-(2-naphthamido)-3-cyclohexylpropanoyl)-N-(6-(2-amino-2-oxoacetyl)spiro[2.5]octan-6-yl)-4-(5-(2-hydroxypropan-2-yl)-1H-1,2,3-triazol-1-yl)pyrrolidine-2-carboxamide

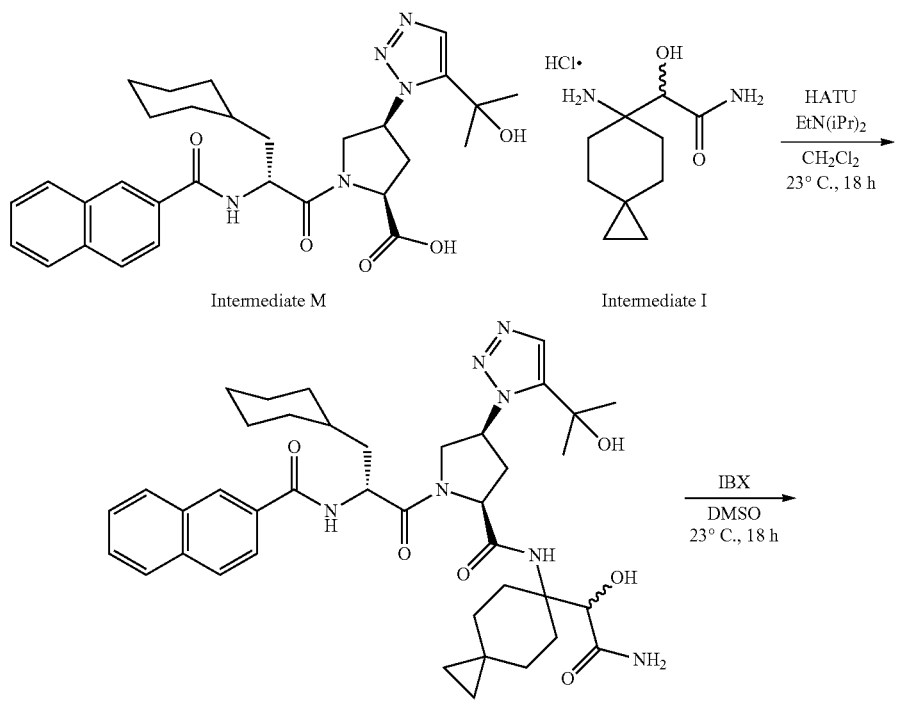

-continued

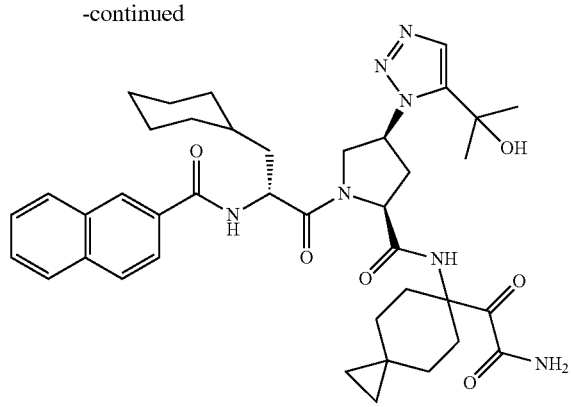

Example 48

Step 1: Preparation of (2S,4S)-1-((R)-2-(2-naphthamido)-3-cyclohexylpropanoyl)-N-(6-(2-amino-1-hydroxy-2-oxoethyl)spiro[2.5]octan-6-yl)-4-(5-(2-hydroxypropan-2-yl)-1H-1,2,3-triazol-1-yl)pyrrolidine-2-carboxamide Prepared in a similar manner as (2S,4S)-1-((R)-2-(2-naphthamido)-3-cyclohexylpropanoyl)-N-(1-(2-amino-1-hydroxy-2-oxoethyl)cyclobutyl)-4-azidopyrrolidine-2-carboxamide (step 1, example 1) using intermediate M and intermediate I to provide the title compound.

Step 2: Preparation of (2S,4S)-1-((R)-2-(2-naphthamido)-3-cyclohexylpropanoyl)-N-(6-(2-amino-2-oxoacetyl)spiro[2.5]octan-6-yl)-4-(5-(2-hydroxypropan-2-yl)-1H-1,2,3-triazol-1-yl)pyrrolidine-2-carboxamide Prepared in a similar manner as tert-butyl ((R)-1-((2S,3R,4R)-2-((1-(2-amino-2-oxoacetyl) cyclohexyl) carbamoyl)-4-(5-(2-hydroxypropan-2-yl)-1H-1,2,3-triazol-1-yl)-3-methoxypyrrolidin-1-yl)-3-cyclohexyl-1-oxopropan-2-yl) carbamate (step 4, example 9) using (2S,4S)-1-((R)-2-(2-naphthamido)-3-cyclohexylpropanoyl)-N-(6-(2-amino-1-hydroxy-2-oxoethyl)spiro[2.5]octan-6-yl)-4-(5-(2-hydroxypropan-2-yl)-1H-1,2,3-triazol-1-yl)pyrrolidine-2-carboxamide to provide the title compound. MS (ESI+) 726 (M+1)⁰

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein may be employed in practicing the present disclosure. It is intended that the following claims define the scope of the present disclosure and that methods and structures within the scope of these claims and their equivalents be covered thereby.

What is claimed is:
1. A compound of Formula I:

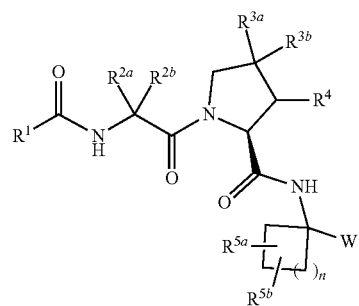

or a pharmaceutically acceptable salt, solvate, solvate of the salt or prodrug thereof wherein:
W is selected from the group consisting of: $B(OH)_2$ and $C(O)C(O)NR^7R^8$;
$R^1$ is selected from the group consisting of:
  (a) —$(CH_2)_{0-6}$-aryl, and
  (b) —$(CH_2)_{0-6}$-heteroaryl,
wherein the aryl and heteroaryl of choices (a) and (b) are each optionally substituted with 1 to 3 substituents independently selected from the group consisting of:
  (i) -halogen,
  (ii) —CN,
  (iii) —$C_{1-6}$alkyl,
  (iv) —$C_{0-6}$ alkyl-$R^6$,
  (v) —$C_{2-6}$ alkenyl,
  (vi) —$C_{2-6}$alkynyl,
  (vii) —$C(O)R^7$,
  (viii) —$CO_2R^7$,
  (ix) —$CONR^7R^8$,
  (x) —OH,
  (xi) —O—$C_{1-6}$alkyl,
  (xii) —O—$C_{0-6}$alkyl-$R^6$,
  (xiii) —SH,
  (xiv) —$S(O)_p$—$C_{1-6}$alkyl,
  (xv) —$S(O)_p$—$C_{0-6}$alkyl-$R^6$,
  (xvi) —$S(O)_2NR^7R^8$,
  (xvii) —$NO_2$,
  (xviii) —$NR^7R^8$,
  (xix) —$NHC(O)R^7$,
  (xx) —$NHC(O)OR^7$, (xxi) —NHC(O)NR$^7$R$^8$,
(xxii) —NHSO$_2$C$_{1-6}$alkyl, and
(xxiii) —NHSO$_2$C$_{0-6}$alkyl-R$^6$,
(xxiv) —CONH(CH$_2$)$_{2-4}$—[O(CH$_2$)$_{2-4}$]$_m$OC$_{1-4}$alkyl,
wherein each of the alkyl group of choices (iii), (iv), (xi), (xii), (xiv), (xv), (xxii), (xxiii) and (xxiv) is optionally substituted with 1 to 5 substituents independently selected from -halogen, -haloC$_{1-4}$alkyl, —COR$^7$, —CO$_2$R$^7$, —CONR$^7$R$^8$, —NR$^7$R$^8$, —OH, —O—C$_{1-4}$alkyl, —SH and —S—C$_{1-4}$alkyl;
R$^{2a}$ and R$^{2b}$ are independently selected from the group consisting of:
(a) —H,
(b) —C$_{1-8}$alkyl, and
(c) —C$_{0-6}$alkyl-R$^6$,
wherein each of the alkyl group of choices (b) and (c) is optionally substituted with 1 to 5 substituents independently selected from:
(i) -halogen,
(ii) -haloC$_{1-4}$alkyl,
(iii) —NR$^7$R$^8$,
(iv) —OH,
(v) —O—C$_{1-4}$alkyl,
(vi) —SH,
(vii) —S—C$_{1-4}$alkyl,
(viii) —NR$^7$SO$_2$C$_{1-4}$alkyl,
(ix) —NR$^7$C(O)R$^7$, and
(x) —NR$^7$C(O)OR$^7$,
with the proviso that R$^{2a}$ and R$^{2b}$ are not both H;
R$^{3a}$ is H, and R$^{3b}$ is selected from the group consisting of:
(a) —H,
(b) —OH,
(c) -heteroaryl,
(d) —O-heteroaryl,
(e) -heterocycle,
(f) -aryl, and
(g) —O-aryl;
wherein each of the heteroaryl of choices (c) and (d), the heterocycle of choice (e) and the aryl of choices (f) and (g) is optionally substituted with 1 to 3 groups independently selected from the group consisting of:
(i) -halogen,
(ii) —OH,
(iii) —CR$^{10}$R$^{11}$R$^{12}$,
(iv) —(CH$_2$)$_{0-3}$—NHSO$_2$—C$_{1-4}$alkyl,
(v) —(CH$_2$)$_{0-3}$—NHSO$_2$—C$_{3-12}$ cycloalkyl,
(vi) —(CH$_2$)$_{0-3}$—SO$_2$—C$_{1-4}$alkyl,
(vii) —(CH$_2$)$_{0-3}$—C(O)O—R$^7$, and
(viii) —CN; and
wherein the heterocycle of choice (e) is additionally optionally substituted with 1 to 2 oxo groups; or
R$^{3a}$ and R$^{3b}$ together represent oxo;
R$^4$ is selected from a group consisting of
(a) —H,
(b) —C$_{1-4}$alkyl,
(c) -haloC$_{1-4}$alkyl,
(d) —O—C$_{1-4}$alkyl, and
(e) —O-haloC$_{1-4}$alkyl;
R$^{5a}$ and R$^{5b}$ are independently selected from a group consisting of
(a) —H,
(b) —C$_{1-4}$alkyl,
(c) -halogen,
(d) —OH,
(e) —O—C$_{1-4}$alkyl,
(f) —SH, and
(g) —S—C$_{1-4}$alkyl, or R$^{5a}$, R$^{5b}$ and the atom(s) to which they are attached together form a 3- to 6-membered cycloalkyl or a 4- to 6-membered heterocycle having a heteroatom selected from O and S(O)$_p$, and wherein said cycloalkyl or heterocycle is optionally substituted with 1 to 2 groups independently selected from halogen, —C$_{1-4}$alkyl, —OH, —O—C$_{1-4}$alkyl, —SH, —S—C$_{1-4}$alkyl;
R$^6$ is selected from the group consisting of:
(a) —C$_{3-12}$cycloalkyl,
(b) -aryl,
(c) -heteroaryl, and
(d) -heterocyclyl,
wherein each of choices (a) to (d) is optionally substituted with 1 to 3 substituents independently selected from the group consisting of:
(i) —C$_{1-4}$alkyl,
(ii) -halogen,
(iii) —NR$^7$R$^8$,
(iv) —OH,
(v) —O—C$_{1-4}$alkyl,
(vi) —SH, and
(vii) —S—C$_{1-4}$alkyl;
wherein each of the alkyl group of choices (i), (v) and (vii) is optionally substituted with 1 to 5 substituents independently selected from -halogen, -haloC$_{1-4}$alkyl, —OH, —O—C$_{1-4}$alkyl, —SH and —S—C$_{1-4}$alkyl;
each R$^7$ and each R$^8$ are independently selected from the group consisting of:
(a) —H,
(b) —C$_{1-6}$alkyl,
(c) —C$_{0-6}$alkyl-C$_{3-12}$cycloalkyl,
(d) —C$_{0-6}$alkyl-heterocyclyl,
(e) —C$_{0-6}$alkyl-heteroaryl,
(f) C$_{0-6}$alkyl-aryl,
(g) —C$_{2-6}$ alkenyl, and
(h) —C$_{2-6}$ alkynyl,
wherein the alkyl group of choices (b)-(f), the alkenyl group of choice (g) and the alkynyl group of (h) are each optionally substituted with 1 to 3 groups independently selected from:
(i) -halogen,
(ii) —C(O)C$_{1-4}$alkyl,
(iii) —C(O)NH$_2$,
(iv) —C(O)NH(C$_{1-4}$alkyl),
(v) —C(O)N(C$_{1-4}$alkyl)(C$_{1-4}$alkyl)
(vi) —OH,
(vii) —OC$_{1-4}$alkyl
(viii) —SH,
(ix) —S(O)$_p$C$_{1-4}$alkyl,
(x) —NH$_2$,
(xi) —NH(C$_{1-4}$alkyl), and
(xii) —N(C$_{1-4}$alkyl)(C$_{1-4}$alkyl); or
R$^7$, R$^8$ and the nitrogen atom to which they are attached together form a 3- to 7-membered monocyclic or 6- to 11-membered bicyclic heterocycle optionally having an additional heteroatom selected from O, S(O)$_p$, and NR$^9$, and wherein said heterocycle is optionally substituted with 1 to 2 halogen;
R$^9$ is selected from the group consisting of:
(a) —H,
(b) —C$_{1-4}$alkyl,
(c) —C(O)—C$_{1-4}$alkyl,
(d) —C(O)NH$_2$,
(e) —C(O)—NH(C$_{1-4}$alkyl),
(f) —C(O)—N(C$_{1-4}$alkyl)$_2$,
(g) —C(O)O—C$_{1-4}$alkyl; and
(h) —C(O)O—C$_{1-4}$alkyl-aryl;

$R^{10}$, $R^{11}$, and $R^{12}$ are independently selected from the group consisting of: H, halogen, —OH and —$C_{1-6}$alkyl; or $R^{10}$, $R^{11}$ and the atom to which they are attached together form a $C_{3-12}$cycloalkyl or a heterocyclyl group;

n is 0, 1, 2, 3, 4 or 5;

m is 1-25; and p is 0, 1 or 2.

2. A compound of claim 1 wherein $R^1$ is selected from the group consisting of:
(a) —aryl, and
(b) -heteroaryl,
wherein aryl and heteroaryl of choices (a) and (b) are each optionally substituted with 1 to 3 substituents independently selected from the group consisting of:
(i) -halogen,
(ii) —CN,
(iii) —$C_{1-6}$alkyl,
(iv) —$C_{0-6}$alkyl-$R^6$,
(v) —$C_{2-6}$alkenyl,
(vi) —$C_{2-6}$alkynyl,
(vii) —C(O)$R^7$,
(viii) —CO$_2R^7$,
(ix) —CONR$^7R^8$,
(x) —OH,
(xi) —O—$C_{1-6}$alkyl,
(xii) —O—$C_{0-6}$alkyl-$R^6$,
(xiii) —SH,
(xiv) —S(O)$_p$—$C_{1-6}$ alkyl,
(xv) —S(O)$_p$—$C_{0-6}$alkyl-$R^5$,
(xvi) —S(O)$_2$NR$^7R^8$,
(xvii) —NO$_2$,
(xviii) —NR$^7R^8$,
(xix) —NHC(O)$R^7$,
(xx) —NHC(O)O$R^7$,
(xxi) —NHC(O)NR$^7R^8$,
(xxii) —NHSO$_2C_{1-6}$alkyl, and
(xxiii) —NHSO$_2C_{0-6}$alkyl-$R^6$,
(xxiv) —CONHC$_{2-4}$alkyl-(OC$_{2-4}$alkylene)$_m$OC$_{1-4}$alkyl,
wherein each of the alkyl group of choices (iii), (iv), (xi), (xii), (xiv), (xv), (xxii) and (xxiii) is optionally substituted with 1 to 5 substituents independently selected from -halogen, -haloC$_{1-4}$alkyl, —CO$^7$, —CO$_2R^7$, —CONR$^7R^8$, —NR$^7R^8$, —OH, —O—$C_{1-4}$alkyl, —SH and —S—$C_{1-4}$alkyl.

3. A compound of claim 1 wherein $R^1$ is selected from the group consisting of:
(a) -aryl, and
(b) -heteroaryl,
wherein the aryl and heteroaryl of choices (a) and (b) are each optionally substituted with 1 to 3 substituents independently selected from the group consisting of:
(i) -halogen,
(ii) —CN,
(iii) —C(O)$R^7$,
(iv) —CONR$^7R^8$,
(v) —OH,
(vi) —O—$C_{1-6}$alkyl,
(vii) —S(O)$_p$—$C_{1-6}$alkyl,
(viii) —S(O)$_p$—$C_{0-6}$alkyl-$R^6$,
(ix) —S(O)$_2$NR$^7R^8$,
(x) —NHSO$_2C_{1-6}$ alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2R^7$, —CONR$^7R^8$, —NR$^7R^8$, —OH, —O—$C_{1-4}$alkyl, —SH and —S—$C_{1-4}$alkyl.

4. A compound of claim 1 wherein $R^{2a}$ is H, and $R^{2b}$ is —$C_{1-6}$alkyl-$R^6$, where the alkyl portion of $R^{2b}$ is optionally substituted with 1 to 5 substituents independently selected from:
(i) -halogen,
(ii) -haloC$_{1-4}$alkyl,
(iii) —NR$^7R^8$,
(iv) —OH,
(v) —OH
(vi) —SH, and
(vii) —S—$C_{1-4}$alkyl.

5. A compound of claim 1 wherein $R^{2a}$ is H, and $R^{2b}$ is —$C_{1-6}$alkyl-$R^6$, and $R^6$ is —$C_{3-12}$cycloalkyl, optionally substituted with 1 to 3 substituents independently selected from the group consisting of:
(i) —$C_{1-4}$alkyl,
(ii) -halogen,
(iii) —NR$^7R^8$,
(iv) —OH,
(v) —O—$C_{1-4}$alkyl,
(vi) —SH, and
(vii) —S—$C_{1-4}$alkyl.

6. A compound of claim 1 wherein $R^{3a}$ is H, and $R^{3b}$ is selected from the group consisting of:

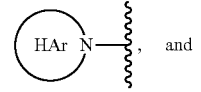, and

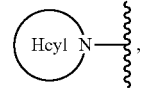, wherein HAr is heteroaryl and Hcyl is heterocycle, wherein HAr and Hcyl are optionally substituted with 1 to 3 groups independently selected from the group consisting of:
(i) -halogen,
(ii) —OH,
(iii) —CR$^{10}R^{11}R^{12}$,
(iv) —(CH$_2$)$_{0-3}$—NHSO$_2$—$C_{1-4}$alkyl,
(v) —(CH$_2$)$_{0-3}$—NHSO$_2$—$C_{3-12}$ cycloalkyl,
(vi) —(CH$_2$)$_{0-3}$—SO$_2$—$C_{1-4}$alkyl,
(vii) —(CH$_2$)$_{0-3}$—C(O)O—$R^7$, and
(viii) —CN; and
wherein Hcyl is additionally optionally substituted with 1 to 2 oxo groups.

7. A compound of claim 1 having the formula Ia:

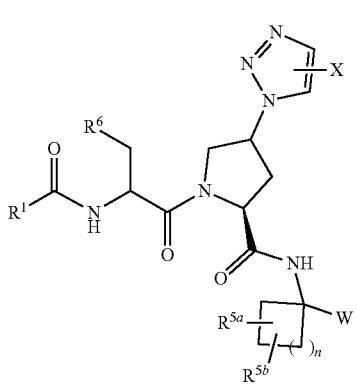

or a pharmaceutically acceptable salt, solvate, solvate of the salt or prodrug thereof wherein:
W is —C(O)C(O)NR$^7$R$^8$,
X is selected from the group consisting of:
  (a) —CR$^{10}$R$^{11}$R$^{12}$,
  (b) —(CH$_2$)$_{0-3}$—SO$_2$—C$_{1-4}$alkyl,
  (c) —(CH$_2$)$_{0-3}$—C(O)O—R$^7$,
  (d) —(CH$_2$)$_{0-3}$—NHSO$_2$—C$_{1-4}$alkyl, and
  (e) —(CH$_2$)$_{0-3}$—NHSO$_2$—C$_{3-12}$ cycloalkyl;
R$^1$ is selected from the group consisting of:
  (a) -aryl and
  (b) -heteroaryl,
wherein the aryl and heteroaryl of choices (a) and (b) are each optionally substituted with 1 to 3 substituents independently selected from the group consisting of:
  (i) -halogen,
  (ii) —CN,
  (iii) —C(O)R$^7$,
  (iv) —CONR$^7$R$^8$,
  (v) —OH,
  (vi) —O—C$_{1-6}$ alkyl,
  (vii) —S(O)$_p$—C$_{1-6}$alkyl,
  (viii) —S(O)$_p$—C$_{0-6}$alkyl-R$^6$,
  (ix) —S(O)$_2$NR$^7$R$^8$,
  (x) —NHSO$_2$C$_{1-6}$ alkyl, and
wherein each of the alkyl group of choices (vi), (vii), (viii) and (x) is optionally substituted with 1 to 5 substituents independently selected from -halogen, -haloC$_{1-4}$alkyl, —COR$^7$, —CO$_2$R$^7$, —CONR$^7$R$^8$, NR$^7$R$^8$, —OH, —O—C$_{1-4}$alkyl, —SH and —S—C$_{1-4}$alkyl;
R$^{5a}$ and R$^{5b}$ are independently selected from a group consisting of
  (a) —H,
  (b) —C$_{1-4}$alkyl,
  (c) -halogen,
  (d) —OH,
  (e) —O—C$_{1-4}$alkyl,
  (f) —SH, and
  (g) —S—C$_{1-4}$alkyl, or
R$^{5a}$, R$^{5b}$ and the atom(s) to which they are attached together form a 3- to 6-membered cycloalkyl or a 4- to 6-membered heterocycle having a heteroatom selected from O and S(O)$_p$, and wherein said cycloalkyl or heterocycle is optionally substituted with 1 to 2 groups independently selected from halogen, —C$_{1-4}$alkyl, —OH, —O—C$_{1-4}$alkyl, —SH, —S—C$_{1-4}$alkyl;

R$^6$ is —C$_{3-12}$cycloalkyl, optionally substituted with 1 to 3 substituents independently selected from the group consisting of:
  (i) —C$_{1-4}$alkyl,
  (ii) -halogen,
  (iii) —NR$^7$R$^8$,
  (iv) —OH,
  (v) —O—C$_{1-4}$alkyl,
  (vi) —SH, and
  (vii) —S—C$_{1-4}$alkyl;
each R$^7$ and each R$^8$ are independently selected from the group consisting of:
  (a) —H,
  (b) —C$_{1-6}$alkyl,
  (c) —C$_{0-6}$ alkyl-C$_{3-12}$cycloalkyl, and
  (d) —C$_{0-6}$ alkyl-heterocyclyl,
wherein the alkyl group of choices (b)-(d) are each optionally substituted with 1 to 3 groups independently selected from:
  (i) -halogen,
  (ii) —C(O)C$_{1-4}$alkyl,
  (iii) —C(O)NH$_2$,
  (iv) —C(O)NH(C$_{1-4}$alkyl),
  (v) —C(O)N(C$_{1-4}$alkyl)(C$_{1-4}$alkyl)
  (vi) —S(O)$_p$C$_{1-4}$alkyl, or
R$^7$, R$^8$ and the nitrogen atom to which they are attached together form a 3- to 7-membered monocyclic or 6- to 11-membered bicyclic heterocycle optionally having an additional heteroatom selected from O, S(O)$_p$, and NR$^9$, and wherein said heterocycle is optionally substituted with 1 to 2 halogen;
R$^9$ is selected from the group consisting of:
  (a) —H,
  (b) —C$_{1-4}$alkyl,
  (c) —C(O)—C$_{1-4}$alkyl,
  (d) —C(O)NH$_2$,
  (e) —C(O)—NH(C$_{1-4}$alkyl),
  (f) —C(O)—N(C$_{1-4}$alkyl)$_2$,
  (g) —C(O)O—C$_{1-4}$alkyl; and
  (h) —C(O)O—C$_{1-4}$alkyl-aryl;
R$^{10}$, R$^{11}$, and R$^{12}$ are independently selected from the group consisting of: H, halogen, —OH and —C$_{1-6}$ alkyl; or
R$^{10}$, R$^{11}$ and the atom to which they are attached together form a C$_{3-12}$cycloalkyl or a heterocyclyl group;
n is 0, 1, 2, 3, 4 or 5;
m is 1-25; and
p is 0, 1 or 2.

8. A compound of claim 1 wherein
W is —C(O)C(O)NH$_2$.

9. A compound of claim 8 wherein
X is —CR$^{10}$R$^{11}$R$^{12}$,
R$^{10}$ and R$^{11}$ are each —C$_{1-4}$alkyl, or
R$^{10}$, R$^{11}$ and the atom to which they are attached together form a C$_{3-6}$cycloalkyl or a 4- to 6-membered heterocycle, and
R$^{12}$ is —OH.

10. A compound of claim 9 wherein
R$^{5a}$ and R$^{5b}$ are independently selected from a group consisting of
  (a) —H, and
  (b) —C$_{1-4}$alkyl, or
R$^{5a}$, R$^{5b}$ and the atom(s) to which they are attached together form a 3- to 6-membered cycloalkyl.

11. A compound of claim 1 selected from the group consisting of:

(2S,4S)-1-((R)-2-(2-naphthamido)-3-cyclohexylpropanoyl)-N-(1-(2-amino-2-oxoacetyl)-cyclobutyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclopropyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclopentyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cycloheptyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclooctyl)-4-(5-(2-hydroxypropan-2-yl)-1H-1,2,3-triazol-1-yl)pyrrolidine-2-carboxamide;
(1-((2S,4S)-1-((R)-2-(2-naphthamido)-3-cyclohexylpropanoyl)-4-(5-(2-hydroxypropan-2-yl)-1H-1,2,3-triazol-1-ylpyrrolidine-2-carboxamido)cyclohexyl)boronic acid;
(2S,4R)-1-((R)-2-(2-naphthamido)-3-cyclohexylpropanoyl)-N-(1-(2-amino-2-oxoacetyl)-cyclohexyl)-4-(piperidin-1-yl)pyrrolidine-2-carboxamide;
(2S,3R,4R)-1-((R)-2-(2-naphthamido)-3-cyclohexylpropanoyl)-N-(1-(2-amino-2-oxoacetyl)-cyclohexyl)-4-(5-(2-hydroxypropan-2-yl)-1H-1,2,3-triazol-1-yl)-3-methoxypyrrolidine-2-carboxamide;
(2S,4S)-1-((R)-2-(2-naphthamido)-3-cyclohexylpropanoyl)-N-(1-(2-amino-2-oxoacetyl)-cyclohexyl)-4-(5-((methylsulfonyl)methyl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclohexyl)-4-(5-(3-hydroxyoxetan-3-yl)-1H-1,2,3-triazol-1-yl)pyrrolidine-2-carboxamide;
2-(1-((3S,5S)-1-((R)-2-(2-naphthamido)-3-cyclohexylpropanoyl)-5-((1-(2-amino-2-oxoacetyl)-cyclohexyl)carbamoyl)pyrrolidin-3-yl)-1H-1,2,3-triazol-5-yl)acetic acid;
(2S,4S)-1-((R)-2-(2-naphthamido)-3-cyclohexylpropanoyl)-N-(1-(2-amino-2-oxoacetyl)-cyclohexyl)-4-(5-(cyclopropanesulfonamidomethyl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(5-((methylsulfonyl)methyl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(5-(3-hydroxyoxetan-3-yl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclohexyl)-4-(4-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-N-(1-(2-amino-2-oxoacetyl)-cyclohexyl)-4-(4-(3-hydroxyoxetan-3-yl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(4-(2-hydroxypropan-2-yl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(4-(3-hydroxyoxetan-3-yl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-(methylsulfonyl)-benzamido)propanoyl)-4-(4-((methylsulfonyl)methyl)-1H-1,2,3-triazol-1-yl)pyrrolidine-2-carboxamide;
N—(R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)imidazo[1,2-a]pyridine-6-carboxamide;
(2S,4S)—N-(1-(2-amino-2-oxoacetyl)cyclohexyl)-1-((R)-2-(4-cyanobenzamido)-3-cyclohexylpropanoyl)-4-(5-(2-hydroxypropan-2-yl)-1H-1,2,3-triazol-1-yl)pyrrolidine-2-carboxamide;
N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)quinoline-3-carboxamide;
N—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-1H-indazole-7-carboxamide;
(2S,4S)—N-(1-(2-amino-2-oxoacetyl)cyclohexyl)-1-((R)-3-cyclohexyl-2-(4-((2-methoxyethyl)-sulfonyl)benzamido)propanoyl)-4-(5-(2-hydroxypropan-2-yl)-1H-1,2,3-triazol-1-yl)pyrrolidine-2-carboxamide;
(2S,4S)—N-(1-(2-amino-2-oxoacetyl)cyclohexyl)-1-((R)-3-cyclohexyl-2-(4-((difluoromethyl)-sulfonyl)benzamido)propanoyl)-4-(5-(2-hydroxypropan-2-yl)-1H-1,2,3-triazol-1-yl)pyrrolidine-2-carboxamide;
(2S,4S)—N-(1-(2-amino-2-oxoacetyl)cyclohexyl)-1-((R)-2-(4-((2-amino-2-oxoethyl)sulfonyl)-benzamido)-3-cyclohexylpropanoyl)-4-(5-(2-hydroxypropan-2-yl)-1H-1,2,3-triazol-1-yl)pyrrolidine-2-carboxamide;
$N^2$—((R)-1-(2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(2,5,8,11-tetraoxatridecan-13-yl)naphthalene-2,6-dicarboxamide;
$N^2$—((R)-1-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-cyclohexyl-1-oxopropan-2-yl)-$N^6$-(tetracosaoxatriheptacontan-73-yl)naphthalene-2,6-dicarboxamide;
(2S,4S)-1-((R)-2-(2-naphthamido)-3-cyclohexylpropanoyl)-N-(1-(2-((2-amino-2-oxoethyl)-amino)-2-oxoacetyl)cyclohexyl)-4-(5-(2-hydroxypropan-2-yl)-1H-1,2,3-triazol-1-yl)pyrrolidine-2-carboxamide;
(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(((methylsulfonyl)methyl)amino)-2-oxoacetyl)cyclohexyl)pyrrolidine-2-carboxamide;
(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-oxo-2-((2,2,2-trifluoroethyl)amino)acetyl)cyclohexyl)pyrrolidine-2-carboxamide;

(2S,4S)-1-((R)-2-(2-naphthamido)-3-cyclohexylpropanoyl)-4-(5-(2-hydroxypropan-2-yl)-1H-1,2,3-triazol-1-yl)-N-(1-(2-(oxetan-3-ylamino)-2-oxoacetyl)cyclohexyl)pyrrolidine-2-carboxamide;

(2S,4S)-1-(2-(2-naphthamido)-3-cyclohexyl-2-methylpropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(spiro[3.3]heptan-2-yl)propanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-(2-(2-naphthamido)-3-(bicyclo[2.2.1]heptan-1-yl)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-1-(3-cyclohexyl-2-methyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)cyclohexyl)-4-(5-(2-hydroxypropan-2-yl)-1H-1,2,3-triazol-1-yl)-1-(2-(4-(methylsulfonyl)benzamido)-3-(spiro[3.3]heptan-2-yl)propanoyl)pyrrolidine-2-carboxamide;

(2S,4S)—N-(1-(2-amino-2-oxoacetyl)cyclohexyl)-1-(3-(bicyclo[2.2.1]heptan-1-yl)-2-(4-(methylsulfonyl)benzamido)propanoyl)-4-(5-(2-hydroxypropan-2-yl)-1H-1,2,3-triazol-1-yl)pyrrolidine-2-carboxamide;

benzyl ((R)-2-(2-naphthamido)-3-((2S,4S)-2-((1-(2-amino-2-oxoacetyl)cyclohexyl)carbamoyl)-4-(5-(2-hydroxypropan-2-yl)-1H-1,2,3-triazol-1-yl)pyrrolidin-1-yl)-3-oxopropyl)carbamate;

(2S,4S)-1-((R)-2-(2-naphthamido)-3-(methylsulfonamido)propanoyl)-N-(1-(2-amino-2-oxoacetyl)cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-acetamidopropanoyl)-N-(1-(2-amino-2-oxoacetyl)-cyclohexyl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(2-(2-amino-2-oxoacetyl)-spiro[3.3]heptan-2-yl)-4-(5-(2-hydroxypropan-2-yl)-1H-1,2,3-triazol-1-yl)pyrrolidine-2-carboxamide;

(2S,4S)-1-((R)-2-(2-naphthamido)-3-cyclohexylpropanoyl)-N-(1-(2-amino-2-oxoacetyl)-4,4-dimethylcyclohexyl)-4-(5-(2-hydroxypropan-2-yl)-1H-1,2,3-triazol-1-yl)pyrrolidine-2-carboxamide;

(2S,4S)—N-(2-(2-amino-2-oxoacetyl)spiro[3.3]heptan-2-yl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide;

(2S,4S)—N-(1-(2-amino-2-oxoacetyl)-4,4-dimethylcyclohexyl)-1-((R)-3-cyclohexyl-2-(4-(methylsulfonyl)benzamido)propanoyl)-4-(5-(2-hydroxypropan-2-yl)-1H-1,2,3-triazol-1-yl)pyrrolidine-2-carboxamide; and (2S,4S)-1-((R)-2-(2-naphthamido)-3-cyclohexylpropanoyl)-N-(6-(2-amino-2-oxoacetyl)-spiro [2.5]octan-6-yl)-4-(5-(2-hydroxypropan-2-yl)-1H-1,2,3-triazol-1-yl)pyrrolidine-2-carboxamide; or a pharmaceutically acceptable salt, solvate, salt of the solvate, or prodrug thereof.

12. A pharmaceutical composition comprising a compound of claim 1 and a pharmaceutically acceptable carrier.

* * * * *